US012773451B1

(12) United States Patent
Byrne et al.

(10) Patent No.: US 12,773,451 B1
(45) Date of Patent: Oct. 27, 2026

(54) METHODS OF TOLERIZING A SUBJECT TO A VIRAL VECTOR

(71) Applicant: University of Florida Research Foundation, Incorporated, Gainesville, FL (US)

(72) Inventors: Barry John Byrne, Gainesville, FL (US); Manuela Corti, Alachua, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 601 days.

(21) Appl. No.: 18/332,431

(22) Filed: Jun. 9, 2023

Related U.S. Application Data

(60) Provisional application No. 63/351,079, filed on Jun. 10, 2022.

(51) Int. Cl.

| | |
|---|---|
| ***A61K 39/215*** | (2006.01) |
| ***A61K 38/17*** | (2006.01) |
| ***A61K 38/47*** | (2006.01) |
| ***A61K 39/00*** | (2006.01) |
| ***A61K 48/00*** | (2006.01) |
| ***A61P 31/14*** | (2006.01) |
| ***C12N 15/86*** | (2006.01) |

(52) U.S. Cl.
CPC ........ *A61K 39/215* (2013.01); *A61K 38/1709* (2013.01); *A61K 38/47* (2013.01); *A61K 48/0058* (2013.01); *A61K 48/0066* (2013.01); *A61P 31/14* (2018.01); *C12N 15/86* (2013.01); *A61K 2039/5256* (2013.01); *A61K 2039/575* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | | |
|---|---|---|---|---|
| 6,759,237 | B1 * | 7/2004 | Wilson ............... | C07K 14/8125 435/456 |
| 2020/0138978 | A1 | 5/2020 | Hoffman | |
| 2021/0346493 | A1 * | 11/2021 | Zhou .................... | C07K 14/165 |
| 2025/0352626 | A1 | 11/2025 | Byrne et al. | |

FOREIGN PATENT DOCUMENTS

| | | | | |
|---|---|---|---|---|
| WO | WO 2020229695 | A | 11/2020 | |
| WO | WO-2020229695 | A1 * | 11/2020 | ............ C12N 15/86 |
| WO | WO 2023/240222 | A2 | 12/2023 | |

OTHER PUBLICATIONS

Keeler et al., Liver induced transgene tolerance with AAV vectors, 2019, Cellular Immunology, vol. 342 (Year: 2019).*
Doerfler et al., Copackaged AAV9 Vectors Promote Simultaneous Immune Tolerance and Phenotypic Correction of Pompe Disease, 2016, Hum Gene Ther. Vol. 27, pp. 43-59 (Year: 2016).*
NCI Dictionary, Antigen definition, 2025, https://www.cancer.gov/publications/dictionaries/cancer-terms/def/antigen (Year: 2025).*
Gurda et al., Capsid Antibodies to Different Adeno-Associated Virus Serotypes Bind Common Regions, Aug. 2013, Journal of Virology, vol. 87, No. 16, p. 9111-9124 (Year: 2013).*

* cited by examiner

*Primary Examiner* — Allison M Fox
*Assistant Examiner* — Marisol Ann O'Neill
(74) *Attorney, Agent, or Firm* — Alston & Bird LLP

(57) ABSTRACT

Described are viral vectors, compositions, kits, and methods or using the vectors, compositions, kits to modulate immune response in a subject. The viral vectors include therapeutic recombinant adeno-associated viruses (rAAVs) and tolerance inducing rAAVs. The therapeutic rAAVs and tolerance inducing AAVs can be used to deliver one or more therapeutic nucleic acids to the subject. The tolerance inducing rAAVs induce immune-specific tolerance to the therapeutic rAAVs to improve efficacy of the therapeutic rAAVs and allow for multiple administrations of the therapeutic rAAVs with little or no associated immune response to the therapeutic rAAVs. The therapeutic rAAVs can be used to administer a therapeutic effect to the subject.

20 Claims, 3 Drawing Sheets

Specification includes a Sequence Listing.

SEQUENCE LISTING

```
Sequence total quantity: 10
SEQ ID NO: 1            moltype = AA  length = 534
FEATURE                 Location/Qualifiers
REGION                  1..534
                        note = MISC_FEATURE - VP3 Capsid Protein of AAV1
source                  1..534
                        mol_type = protein
                        organism = adeno-associated virus
SEQUENCE: 1
MASGGGAPMA DNNEGADGVG NASGNWHCDS TWLGDRVITT STRTWALPTY NNHLYKQISS  60
ASTGASNDNH YFGYSTPWGY FDFNRFHCHF SPRDWQRLIN NNWGFRPKRL NFKLFNIQVK  120
EVTTNDGVTT IANNLTSTVQ VFSDSEYQLP YVLGSAHQGC LPPFPADVFM IPQYGYLTLN  180
NGSQAVGRSS FYCLEYFPSQ MLRTGNNFTF SYTFEEVPFH SSYAHSQSLD RLMNPLIDQY  240
LYYLNRTQNQ SGSAQNKDLL FSRGSPAGMS VQPKNWLPGP CYRQQRVSKT KTDNNNSNFT  300
WTGASKYNLN GRESIINPGT AMASHKDDED KFFPMSGVMI FGKESAGASN TALDNVMITD  360
EEEIKATNPV ATERFGTVAV NFQSSSTDPA TGDVHAMGAL PGMVWQDRDV YLQGPIWAKI  420
PHTDGHFHPS PLMGGFGLKN PPPQILIKNT PVPANPPAEF SATKFASFIT QYSTGQVSVE  480
IEWELQKENS KRWNPEVQYT SNYAKSANVD FTVDNNGLYT EPRPIGTRYL TRPL        534

SEQ ID NO: 2            moltype = DNA  length = 1605
FEATURE                 Location/Qualifiers
misc_feature            1..1605
                        note = AAV VP3 Capsid DNA
source                  1..1605
                        mol_type = genomic DNA
                        organism = adeno-associated virus
SEQUENCE: 2
atggcttcag gcggtggcgc accaatggca gacaataacg aaggcgccga cggagtgggt  60
aatgcctcag gaaattggca ttgcgattcc acatggctgg gcgacagagt catcaccacc  120
agcacccgca cctgggcctt gcccacctac aataaccacc tctacaagca aatctccagt  180
gcttcaacgg gggccagcaa cgacaaccac tacttcggct acagcacccc ctgggggtat  240
tttgatttca acagattcca ctgccacttt tcaccacgtg actggcagcg actcatcaac  300
aacaattggg gattccggcc caagagactc aacttcaaac tcttcaacat ccaagtcaag  360
gaggtcacga cgaatgatgg cgtcacaacc atcgctaata accttaccag cacggttcaa  420
gtcttctcgg actcggagta ccagcttccg tacgtcctcg gctctgcgca ccagggctgc  480
ctccctccgt tcccggcgga cgtgttcatg attccgcaat acggctacct gacgctcaac  540
```

```
aatggcagcc aagccgtggg acgttcatcc ttttactgcc tggaatattt cccttctcag  600
atgctgagaa cgggcaacaa ctttaccttc agctacacct ttgaggaagt gcctttccac  660
agcagctacg cgcacagcca gagcctggac cggctgatga atcctctcat cgaccaatac  720
ctgtattacc tgaacagaac tcaaaatcag tccggaagtg cccaaaacaa ggacttgctg  780
tttagccgtg ggtctccagc tggcatgtct gttcagccca aaaactggct acctggaccc  840
tgttatcggc agcagcgcgt ttctaaaaca aaaacagaca acaacaacag caattttacc  900
tggactggtg cttcaaaata taacctcaat gggcgtgaat ccatcatcaa ccctggcact  960
gctatggcct cacacaaaga cgacgaagac aagttctttc ccatgagcgg tgtcatgatt  1020
tttggaaaag agagcgccgg agcttcaaac actgcattgg acaatgtcat gattacagac  1080
gaagaggaaa ttaaagccac taaccctgtg gccaccgaaa gatttgggac cgtggcagtc  1140
aatttccaga gcagcagcac agaccctgcg accggagatg tgcatgctat gggagcatta  1200
cctggcatgg tgtggcaaga tagagacgtg tacctgcagg gtcccatttg ggccaaaatt  1260
cctcacacag atggacactt tcacccgtct cctcttatgg gcggctttgg actcaagaac  1320
ccgcctcctc agatcctcat caaaaacacg cctgttcctg cgaatcctcc ggcggagttt  1380
tcagctacaa agtttgcttc attcatcacc caatactcca caggacaagt gagtgtggaa  1440
attgaatggg agctgcagaa agaaaacagc aagcgctgga atcccgaagt gcagtacaca  1500
tccaattatg caaaatctgc caacgttgat tttactgtgg acaacaatgg actttatact  1560
gagcctcgcc ccattggcac ccgttacctt acccgtcccc tgtaa                   1605

SEQ ID NO: 3           moltype = DNA  length = 410
FEATURE                Location/Qualifiers
misc_feature           1..410
                       note = Liver Specific Promoter
misc_feature           1..410
                       note = Liver specific GAA Promoter
source                 1..410
                       mol_type = other DNA
                       organism = synthetic construct
SEQUENCE: 3
ccctaaaatg ggcaaacatt gcaagcagca aacagcaaac acacagccct ccctgcctgc  60
tgaccttgga gctggggcag aggtcagaga cctctctggg gactgtccca ggtcagtggt  120
ggtgcctgaa gctgaggaga cagggccctg tcctcgtccg tatttaagca gtggatccag  180
aggggcaacg ggggaggctg ctggtgaata ttaaccaagg tcaccccagt tatcggagga  240
gcaaacaggg gctaagtcca ctggctggga tctgagtcgc ccgcctacgc tgcccggacg  300
ctttgcctgg gcagtgtaca gcttccactg cacttaccga aaggagtcat tgtagggccc  360
tgtctcctca gcttcaggca ccaccactga cctgggacag tgaatccgga             410

SEQ ID NO: 4           moltype = DNA  length = 5603
FEATURE                Location/Qualifiers
misc_feature           1..5603
                       note = pTR-LSP-AAV1-VP3
source                 1..5603
                       mol_type = other DNA
                       organism = synthetic construct
SEQUENCE: 4
ctgcaggggg gggggggggg gggttggcca ctccctctct gcgcgctcgc tcgctcactg  60
aggccgggcg accaaaggtc gcccgacgcc cgggctttgc ccgggcggcc tcagtgagcg  120
agcgagcgcg cagagaggga gtggccaact ccatcactag gggttcctag atctccctaa  180
aatgggcaaa cattgcaagc agcaaacagc aaacacacag ccctccctgc ctgctgacct  240
tggagctggg gcagaggtca gagacctctc tggggactgt cccaggtcag tggtggtgcc  300
tgaagctgag gagacagggc cctgtcctcg tccgtattta agcagtggat ccagaggggc  360
aacgggggag gctgctggtg aatattaacc aaggtcaccc cagttatcgg aggagcaaac  420
aggggctaag tccactggct gggatctgag tcgcccgcct acgctgcccg gacgctttgc  480
ctgggcagtg tacagcttcc actgcactta ccgaaaggag tcattgtagg gccctgtctc  540
ctcagcttca ggcaccacca ctgacctggg acagtgaatc cggaaagtat caaggttaca  600
agacaggttt aaggagacca atagaaactg ggcttgtcga gacagagaag actcttgcgt  660
ttctgatagg cacctattgg tcttactgac atccactttg cctttctctc cacagacgcg  720
tggtaccgtc gacccgccac catggcttca ggcggtggcg caccaatggc agacaataac  780
gaaggcgccg acggagtggg taatgcctca ggaaattggc attgcgattc cacatggctg  840
ggcgacagag tcatcaccac cagcacccgc acctgggcct tgcccaccta caataaccac  900
ctctacaagc aaatctccag tgcttcaacg ggggccagca acgacaacca ctacttcggc  960
tacagcaccc cctgggggta ttttgatttc aacagattcc actgccactt ttcaccacgt  1020
gactggcagc gactcatcaa caacaattgg ggattccggc ccaagagact caacttcaaa  1080
ctcttcaaca tccaagtcaa ggaggtcacg acgaatgatg gcgtcacaac catcgctaat  1140
aaccttacca gcacggttca agtcttctcg gactcggagt accagcttcc gtacgtcctc  1200
ggctctgcgc accagggctg cctccctccg ttcccggcgg acgtgttcat gattccgcaa  1260
tacggctacc tgacgctcaa caatggcagc caagccgtgg gacgttcatc cttttactgc  1320
ctggaatatt tcccttctca gatgctgaga acgggcaaca actttacctt cagctacacc  1380
tttgaggaag tgcctttcca cagcagctac gcgcacagcc agagcctgga ccggctgatg  1440
aatcctctca tcgaccaata cctgtattac ctgaacagaa ctcaaaatca gtccggaagt  1500
gcccaaaaca aggacttgct gtttagccgt gggtctccag ctggcatgtc tgttcagccc  1560
aaaaactggc tacctggacc ctgttatcgg cagcagcgcg tttctaaaac aaaaacagac  1620
aacaacaaca gcaattttac ctggactggt gcttcaaaat ataacctcaa tgggcgtgaa  1680
tccatcatca accctggcac tgctatggcc tcacacaaag acgacgaaga caagttcttt  1740
cccatgagcg gtgtcatgat ttttggaaaa gagagcgccg gagcttcaaa cactgcattg  1800
gacaatgtca tgattacaga cgaagaggaa attaaagcca ctaaccctgt ggccaccgaa  1860
agatttggga ccgtggcagt caatttccag agcagcagca cagaccctgc gaccggagat  1920
gtgcatgcta tgggagcatt acctggcatg gtgtggcaag atagagacgt gtacctgcag  1980
ggtcccattt gggccaaaat tcctcacaca gatggacact ttcacccgtc tcctcttatg  2040
```

```
ggcggctttg gactcaagaa cccgcctcct cagatcctca tcaaaaacac gcctgttcct  2100
gcgaatcctc cggcggagtt ttcagctaca aagtttgctt cattcatcac ccaatactcc  2160
acaggacaag tgagtgtgga aattgaatgg gagctgcaga aagaaaacag caagcgctgg  2220
aatcccgaag tgcagtacac atccaattat gcaaaatctg ccaacgttga ttttactgtg  2280
gacaacaatg gactttatac tgagcctcgc cccattggca cccgttacct tacccgtccc  2340
ctgtaatcta gagatatcgc ggccgcttcg agcagacatg ataagataca ttgatgagtt  2400
tggacaaacc acaactagaa tgcagtgaaa aaaatgcttt atttgtgaaa tttgtgatgc  2460
tattgcttta tttgtaacca ttataagctg caataaacaa gttaacaaca acaattgcat  2520
tcattttatg tttcaggttc agggggagat gtgggaggtt ttttaaagca agtaaaacct  2580
ctacaaatgt ggtaaaatcg ataaggatct aggaacccct agtgatggag ttggccactc  2640
cctctctgcg cgctcgctcg ctcactgagg ccgcccgggc aaagcccggg cgtcgggcga  2700
cctttggtcg cccggcctca gtgagcgagc gagcgcgcag agagggagtg gccaaccccc  2760
ccccccccc  ccctgcagcc tggcgtaata gcgaagaggc ccgcaccgat cgcccttccc  2820
aacagttgcg tagcctgaat ggcgaatggc gcgacgcgcc ctgtagcggc gcattaagcg  2880
cggcgggtgt ggtggttacg cgcagcgtga ccgctacact tgccagcgcc ctagcgcccg  2940
ctcctttcgc tttcttccct tcctttctcg ccacgttcgc cggctttccc cgtcaagctc  3000
taaatcgggg gctcccttta gggttccgat ttagtgcttt acggcacctc gaccccaaaa  3060
aacttgatta gggtgatggt tcacgtagtg ggccatcgcc ctgatagacg gtttttcgcc  3120
ctttgacgtt ggagtccacg ttctttaata gtggactctt gttccaaact ggaacaacac  3180
tcaaccctat ctcggtctat tcttttgatt tataagggat tttgccgatt tcggcctatt  3240
ggttaaaaaa tgagctgatt taacaaaaat ttaacgcgaa ttttaacaaa atattaacgt  3300
ttacaatttc ctgatgcggt attttctcct tacgcatctg tgcggtattt cacaccgcat  3360
atggtgcact ctcagtacaa tctgctctga tgccgcatag ttaagccagc cccgacaccc  3420
gccaacaccc gctgacgcgc cctgacgggc ttgtctgctc ccggcatccg cttacagaca  3480
agctgtgacc gtctccggga gctgcatgtg tcagaggttt tcaccgtcat caccgaaacg  3540
cgcgagacga aagggcctcg tgatacgcct atttttatag gttaatgtca tgataataat  3600
ggtttcttag acgtcaggtg gcacttttcg gggaaatgtg cgcggaaccc ctatttgttt  3660
atttttctaa atacattcaa atatgtatcc gctcatgaga caataaccct gataaatgct  3720
tcaataatat tgaaaaagga agagtatgag tattcaacat ttccgtgtcg cccttattcc  3780
cttttttgcg gcattttgcc ttcctgtttt tgctcaccca gaaacgctgg tgaaagtaaa  3840
agatgctgaa gatcagttgg gtgcacgagt gggttacatc gaactggatc tcaacagcgg  3900
taagatcctt gagagttttc gccccgaaga acgttttcca atgatgagca cttttaaagt  3960
tctgctatgt ggcgcggtat tatcccgtat tgacgccggg caagagcaac tcggtcgccg  4020
catacactat tctcagaatg acttggttga gtactcacca gtcacagaaa agcatcttac  4080
ggatggcatg acagtaagag aattatgcag tgctgccata accatgagtg ataacactgc  4140
ggccaactta cttctgacaa cgatcggagg accgaaggag ctaaccgctt ttttgcacaa  4200
catgggggat catgtaactc gccttgatcg ttgggaaccg gagctgaatg aagccatacc  4260
aaacgacgag cgtgacacca cgatgcctgt agcaatggca acaacgttgc gcaaactatt  4320
aactggcgaa ctacttactc tagcttcccg gcaacaatta atagactgga tggaggcgga  4380
taaagttgca ggaccacttc tgcgctcggc ccttccggct ggctggttta ttgctgataa  4440
atctggagcc ggtgagcgtg ggtctcgcgg tatcattgca gcactggggc cagatggtaa  4500
gccctcccgt atcgtagtta tctacacgac ggggagtcag gcaactatgg atgaacgaaa  4560
tagacagatc gctgagatag gtgcctcact gattaagcat tggtaactgt cagaccaagt  4620
ttactcatat atactttaga ttgatttaaa acttcatttt taatttaaaa ggatctaggt  4680
gaagatcctt tttgataatc tcatgaccaa aatcccttaa cgtgagtttt cgttccactg  4740
agcgtcagac cccgtagaaa agatcaaagg atcttcttga gatccttttt ttctgcgcgt  4800
aatctgctgc ttgcaaacaa aaaaaccacc gctaccagcg gtggtttgtt tgccggatca  4860
agagctacca actctttttc cgaaggtaac tggcttcagc agagcgcaga taccaaatac  4920
tgtccttcta gtgtagccgt agttaggcca ccacttcaag aactctgtag caccgcctac  4980
atacctcgct ctgctaatcc tgttaccagt ggctgctgcc agtggcgata agtcgtgtct  5040
taccgggttg gactcaagac gatagttacc ggataaggcg cagcggtcgg gctgaacggg  5100
gggttcgtgc acacagccca gcttggagcg aacgacctac accgaactga gatacctaca  5160
gcgtgagcat tgagaaagcg ccacgcttcc cgaagggaga aaggcggaca ggtatccggt  5220
aagcggcagg gtcggaacag gagagcgcac gagggagctt ccagggggaa acgcctggta  5280
tctttatagt cctgtcgggt ttcgccacct ctgacttgag cgtcgatttt tgtgatgctc  5340
gtcagggggg cggagcctat ggaaaaacgc cagcaacgcg gcctttttac ggttcctggc  5400
cttttgctgg ccttttgctc acatgttctt tcctgcgtta tcccctgatt ctgtggataa  5460
ccgtattacc gcctttgagt gagctgatac cgctcgccgc agccgaacga ccgagcgcag  5520
cgagtcagtg agcgaggaag cggaagagcg cccaatacgc aaaccgcctc tccccgcgcg  5580
ttggccgatt cattaatgca ggg                                          5603
```

```
SEQ ID NO: 5            moltype = DNA  length = 3841
FEATURE                 Location/Qualifiers
misc_feature            1..3841
                        note = SARS-CoV-2 Spike Protein
source                  1..3841
                        mol_type = other DNA
                        organism = synthetic construct
SEQUENCE: 5
agcttgaatt cgccaccatg ttcgtgtttc tggtgctgct gcctctggtg tccagccagt  60
gtgtgaacct gaccaccaga acacagctgc ctccagccta caccaacagc tttaccagag  120
gcgtgtacta ccccgacaag gtgttcagat ccagcgtgct gcactctacc caggacctgt  180
tcctgccttt cttcagcaac gtgacctggt tccacgccat ccacgtgtcc ggcaccaatg  240
gcaccaagag attcgacaac cccgtgctgc ccttcaacga cggggtgtac tttgccagca  300
ccgagaagtc caacatcatc agaggctgga tcttcggcac cacactggac agcaagaccc  360
agagcctgct gatcgtgaac aacgccacca acgtggtcat caaagtgtgc gagttccagt  420
tctgcaacga ccccttcctg ggcgtctact accacaagaa caacaagagc tggatggaaa  480
gcgagttccg ggtgtacagc agcgccaaca actgcacctt cgagtacgtg tcccagcctt  540
tcctgatgga cctggaaggc aagcagggca acttcaagaa cctgcgcgag ttcgtgttca  600
```

-continued

```
agaacatcga cggctacttc aagatctaca gcaagcacac ccctatcaac ctcgtgcggg  660
atctgcctca gggcttctct gctctggaac ccctggtgga tctgcccatc ggcatcaaca  720
tcacccggtt tcagacactg ctggccctgc acagaagcta cctgacacct ggcgatagca  780
gcagcggatg gacagctggt gccgccgctt actatgtggg ctacctgcag cctagaacct  840
tcctgctgaa gtacaacgag aacggcacca tcaccgacgc cgtggattgt gctctggatc  900
ctctgagcga gacaaagtgc accctgaagt ccttcaccgt ggaaaagggc atctaccaga  960
ccagcaactt ccgggtgcag cccaccgaat ccatcgtgcg gttccccaat atcaccaatc  1020
tgtgcccctt cggcgaggtg ttcaatgcca ccagattcgc ctctgtgtac gcctggaacc  1080
ggaagcggat cagcaattgc gtggccgact actccgtgct gtacaactcc gccagcttca  1140
gcaccttcaa gtgctacggc gtgtccccta ccaagctgaa cgacctgtgc ttcacaaacg  1200
tgtacgccga cagcttcgtg atccggggag atgaagtgcg gcagattgcc cctggacaga  1260
caggcaagat cgccgactac aactacaagc tgcccgacga cttcaccggc tgtgtgattg  1320
cctggaacag caacaacctg gactccaaag tcggcggcaa ctacaattac ctgtaccggc  1380
tgttccggaa gtccaatctg aagcccttcg agcgggacat ctccaccgag atctatcagg  1440
ccggcagcac cccttgtaac ggcgtggaag gcttcaactg ctacttccca ctgcagtcct  1500
acggctttca gcccacaaat ggcgtgggct atcagccccta cagagtggtg gtgctgagct  1560
tcgaactgct gcatgcccct gccacagtgt gcggccctaa gaaaagcacc aatctcgtga  1620
agaacaaatg cgtgaacttc aacttcaacg gcctgaccgg caccggcgtg ctgacagaga  1680
gcaacaagaa gttcctgcca ttccagcagt ttggccggga tatcgccgat accacagacg  1740
ccgttagaga tccccagaca ctggaaatcc tggacatcac cccttgcagc ttcggcggag  1800
tgtctgtgat cacccctggc accaacacca gcaatcaggt ggcagtgctg taccaggacg  1860
tgaactgtac cgaagtgccc gtggccattc acgccgatca gctgacacct acatggcggg  1920
tgtactccac cggcagcaat gtgtttcaga ccagagccgg ctgtctgatc ggagccgagc  1980
acgtgaacaa tagctacgag tgcgacatcc ccatcggcgc tggcatctgt gccagctacc  2040
agacacagac aaacagcccc agacgggcca gatctgtggc cagccagagc atcattgcct  2100
acacaatgtc tctgggcgcc gagaacagcg tggcctactc caacaactct atcgctatcc  2160
ccaccaactt caccatcagc gtgaccacag agatcctgcc tgtgtccatg accaagacca  2220
gcgtggactg caccatgtac atctgcggcg attccaccga gtgctccaac ctgctgctgc  2280
agtacggcag cttctgcacc cagctgaata gagccctgac aggatcgcc gtggaacagg  2340
acaagaacac ccaagaggtg ttcgcccaag tgaagcagat ctacaagacc cctcctatca  2400
aggacttcgg cggcttcaat ttcagccaga ttctgcccga tcctagcaag cccagcaagc  2460
ggagcttcat cgaggacctg ctgttcaaca aagtgacact ggccgacgcc ggcttcatca  2520
agcagtatgg cgattgtctg ggcgacattg ccgccaggga tctgatttgc gcccagaagt  2580
ttaacggact gacagtgctg cctcctctgc tgaccgatga gatgatcgcc cagtacacat  2640
ctgccctgct ggccggcaca atcacaagcg gctggacatt tggagctggc gccgctctgc  2700
agatcccctt tgctatgcag atggcctacc ggttcaacgg catcggagtg acccagaatg  2760
tgctgtacga gaaccagaag ctgatcgcca accagttcaa cagcgccatc ggcaagatcc  2820
aggacagcct gagcagcaca gcaagcgccc tgggaaagct gcaggacgtg gtcaaccaga  2880
atgcccaggc actgaacacc ctggtcaagc agctgtcctc caacttcggc gccatcagct  2940
ctgtgctgaa cgatatcctg agcagactgg accctcctga ggccgaggtg cagatcgaca  3000
gactgatcac aggcagactg cagagcctcc agacatacgt gacccagcag ctgatcagag  3060
ccgccgagat tagagcctct gccaatctgg ccgccaccaa gatgtctgag tgtgtgctgg  3120
gccagagcaa gagagtggac ttttgcggca agggctacca cctgatgagc ttccctcagt  3180
ctgcccctca cggcgtggtg tttctgcacg tgacatatgt gcccgctcaa gagaagaatt  3240
tcaccaccgc tccagccatc tgccacgacg gcaaagccca ctttcctaga gaaggcgtgt  3300
tcgtgtccaa cggcacccat tggttcgtga cacagcggaa cttctacgag ccccagatca  3360
tcaccaccga caacaccttc gtgtctggca actgcgacgt cgtgatcggc attgtgaaca  3420
ataccgtgta cgaccctctg cagcccgagc tggacagctt caaagaggaa ctggacaagt  3480
actttaagaa ccacacaagc cccgacgtgg acctgggcga tatcagcgga atcaatgcca  3540
gcgtcgtgaa catccagaaa gagatcgacc ggctgaacga ggtggccaag aatctgaacg  3600
agagcctgat cgacctgcaa gaactgggga agtacgagca gtacatcaag tggccctggt  3660
acatctggct gggctttatc gccggactga ttgccatcgt gatggtcaca atcatgctgt  3720
gttgcatgac cagctgctgt agctgcctga agggctgttg tagctgtggc agctgctgca  3780
agttcgacga ggacgattct gagcccgtgc tgaagggcgt gaaactgcac tacacctgag  3840
c                                                                  3841
```

```
SEQ ID NO: 6           moltype = DNA  length = 8006
FEATURE                Location/Qualifiers
misc_feature           1..8006
                       note = pTR-SARS2S-2P
source                 1..8006
                       mol_type = other DNA
                       organism = synthetic construct
SEQUENCE: 6
gggggggggg ggggggttg gccactccct ctctgcgcgc tcgctcgctc actgaggccg  60
ggcgaccaaa ggtcgcccga cgcccgggct ttgcccgggc ggcctcagtg agcgagcgag  120
cgcgcagaga gggagtggcc aactccatca ctaggggttc ctagatcttc aatattggcc  180
attagccata ttattcattg gttatatagc ataaatcaat attggctatt ggccattgca  240
tacgttgtat ctatatcata atatgtacat ttatattggc tcatgtccaa tatgaccgcc  300
atgttggcat tgattattga ctagttatta atagtaatca attacggggt cattagttca  360
tagcccatat atggagttcc gcgttacata acttacggta aatggcccgc ctggctgacc  420
gcccaacgac ccccgcccat tgacgtcaat aatgacgtat gttcccatag taacgccaat  480
agggactttc cattgacgtc aatgggtgga gtatttacgg taaactgccc acttggcagt  540
acatcaagtg tatcatatgc caagtccgcc ccctattgac gtcaatgacg gtaaatggcc  600
cgcctggcat tatgcccagt acatgacctt acgggacttt cctacttggc agtacatcta  660
cgtattagtc atcgctatta ccatggtgat gcggttttgg cagtacacca atgggcgtgg  720
atagcggttt gactcacggg gatttccaag tctccacccc attgacgtca atgggagttt  780
gttttggcac caaaatcaac gggactttcc aaaatgtcgt aataaccccg ccccgttgac  840
gcaaatgggc ggtaggcgtg tacggtggga ggtctatata agcagagctc gtttagtgaa  900
```

-continued

```
ccgtcagatc actagaagct tgaattcgcc accatgttcg tgtttctggt gctgctgcct  960
ctggtgtcca gccagtgtgt gaacctgacc accagaacac agctgcctcc agcctacacc  1020
aacagcttta ccagaggcgt gtactacccc gacaaggtgt tcagatccag cgtgctgcac  1080
tctacccagg acctgttcct gcctttcttc agcaacgtga cctggttcca cgccatccac  1140
gtgtccggca ccaatggcac caagagattc gacaaccccg tgctgccctt caacgacggg  1200
gtgtactttg ccagcaccga gaagtccaac atcatcagag gctggatctt cggcaccaca  1260
ctggacagca agacccagag cctgctgatc gtgaacaacg ccaccaacgt ggtcatcaaa  1320
gtgtgcgagt tccagttctg caacgacccc ttcctgggcg tctactacca caagaacaac  1380
aagagctgga tggaaagcga gttccgggtg tacagcagcg ccaacaactg caccttcgag  1440
tacgtgtccc agcctttcct gatggacctg gaaggcaagc agggcaactt caagaacctg  1500
cgcgagttcg tgttcaagaa catcgacggc tacttcaaga tctacagcaa gcacacccct  1560
atcaacctcg tgcgggatct gcctcagggc ttctctgctc tggaaccccct ggtggatctg  1620
cccatcggca tcaacatcac ccggtttcag acactgctgg ccctgcacag aagctacctg  1680
acacctggcg atagcagcag cggatggaca gctggtgccg ccgcttacta tgtgggctac  1740
ctgcagccta gaaccttcct gctgaagtac aacgagaacg gcaccatcac cgacgccgtg  1800
gattgtgctc tggatcctct gagcgagaca aagtgcaccc tgaagtcctt caccgtggaa  1860
aagggcatct accagaccag caacttccgg gtgcagccca ccgaatccat cgtgcggttc  1920
cccaatatca ccaatctgtg ccccttcggc gaggtgttca atgccaccag attcgcctct  1980
gtgtacgcct ggaaccggaa gcggatcagc aattgcgtgg ccgactactc cgtgctgtac  2040
aactccgcca gcttcagcac cttcaagtgc tacggcgtgt cccctaccaa gctgaacgac  2100
ctgtgcttca caaacgtgta cgccgacagc ttcgtgatcc ggggagatga agtgcggcag  2160
attgcccctg gacagacagg caagatcgcc gactacaact acaagctgcc cgacgacttc  2220
accggctgtg tgattgcctg gaacagcaac aacctggact ccaaagtcgg cggcaactac  2280
aattacctgt accggctgtt ccggaagtcc aatctgaagc ccttcgagcg ggacatctcc  2340
accgagatct atcaggccgg cagcacccct tgtaacggcg tggaaggctt caactgctac  2400
ttcccactgc agtcctacgg ctttcagccc acaaatggcg tgggctatca gccctacaga  2460
gtggtggtgc tgagcttcga actgctgcat gcccctgcca cagtgtgcgg ccctaagaaa  2520
agcaccaatc tcgtgaagaa caaatgcgtg aacttcaact tcaacggcct gaccggcacc  2580
ggcgtgctga cagagagcaa caagaagttc ctgccattcc agcagtttgg ccgggatatc  2640
gccgatacca cagacgccgt tagagatccc cagacactgg aaatcctgga catcacccct  2700
tgcagcttcg gcggagtgtc tgtgatcacc cctggcacca acaccagcaa tcaggtggca  2760
gtgctgtacc aggacgtgaa ctgtaccgaa gtgcccgtgg ccattcacgc cgatcagctg  2820
acacctacat ggcgggtgta ctccaccggc agcaatgtgt ttcagaccag agccggctgt  2880
ctgatcggag ccgagcacgt gaacaatagc tacgagtgcg acatccccat cggcgctggc  2940
atctgtgcca gctaccagac acagacaaac agccccagac gggccagatc tgtggccagc  3000
cagagcatca ttgcctacac aatgtctctg ggcgccgaga acagcgtggc ctactccaac  3060
aactctatcg ctatccccac caacttcacc atcagcgtga ccacagagat cctgcctgtg  3120
tccatgacca agaccagcgt ggactgcacc atgtacatct gcggcgattc caccgagtgc  3180
tccaacctgc tgctgcagta cggcagcttc tgcacccagc tgaatagagc cctgacaggg  3240
atcgccgtgg aacaggacaa gaacacccaa gaggtgttcg cccaagtgaa gcagatctac  3300
aagacccctc ctatcaagga cttcggcggc ttcaatttca gccagattct gcccgatcct  3360
agcaagccca gcaagcggag cttcatcgag gacctgctgt tcaacaaagt gacactggcc  3420
gacgccggct tcatcaagca gtatggcgat tgtctgggcg acattgccgc cagggatctg  3480
atttgcgccc agaagtttaa cggactgaca gtgctgcctc ctctgctgac cgatgagatg  3540
atcgcccagt acacatctgc cctgctggcc ggcacaatca caagcggctg gacatttgga  3600
gctggcgccg ctctgcagat cccctttgct atgcagatgg cctaccggtt caacggcatc  3660
ggagtgaccc agaatgtgct gtacgagaac cagaagctga tcgccaacca gttcaacagc  3720
gccatcggca agatccagga cagcctgagc agcacagcaa gcgccctggg aaagctgcag  3780
gacgtggtca accagaatgc ccaggcactg aacaccctgg tcaagcagct gtcctccaac  3840
ttcggcgcca tcagctctgt gctgaacgat atcctgagca gactggaccc tcctgaggcc  3900
gaggtgcaga tcgacagact gatcacaggc agactgcaga gcctccagac atacgtgacc  3960
cagcagctga tcagagccgc cgagattaga gcctctgcca atctggccgc caccaagatg  4020
tctgagtgtg tgctgggcca gagcaagaga gtggactttt gcggcaaggg ctaccacctg  4080
atgagcttcc ctcagtctgc ccctcacggc gtggtgtttc tgcacgtgac atatgtgccc  4140
gctcaagaga agaatttcac caccgctcca gccatctgcc acgacggcaa agcccacttt  4200
cctagagaag gcgtgttcgt gtccaacggc acccattggt tcgtgacaca gcggaacttc  4260
tacgagcccc agatcatcac caccgacaac accttcgtgt ctggcaactg cgacgtcgtg  4320
atcggcattg tgaacaatac cgtgtacgac cctctgcagc ccgagctgga cagcttcaaa  4380
gaggaactgg acaagtactt taagaaccac acaagccccg acgtggacct gggcgatatc  4440
agcggaatca atgccagcgt cgtgaacatc cagaaagaga tcgaccggct gaacgaggtg  4500
gccaagaatc tgaacgagag cctgatcgac ctgcaagaac tggggaagta cgagcagtac  4560
atcaagtggc cctggtacat ctggctgggc tttatcgccg gactgattgc catcgtgatg  4620
gtcacaatca tgctgtgttg catgaccagc tgctgtagct gcctgaaggg ctgttgtagc  4680
tgtggcagct gctgcaagtt cgacgaggac gattctgagc ccgtgctgaa gggcgtgaaa  4740
ctgcactaca cctgagcggc cgcttcgagc agacatgata agatacattg atgagtttgg  4800
acaaaccaca actagaatgc agtgaaaaaa atgctttatt tgtgaaattt gtgatgctat  4860
tgctttattt gtaaccatta taagctgcaa taaacaagtt aacaacaaca attgcattca  4920
ttttatgttt caggttcagg gggagatgtg ggaggttttt taaagcaagt aaaacctcta  4980
caaatgtggt aaaatcgata aggatctagg aaccccctagt gatggagttg gccactccct  5040
ctctgcgcgc tcgctcgctc actgaggccg cccgggcaaa gcccgggcgt cgggcgacct  5100
ttggtcgccc ggcctcagtg agcgagcgag cgcgcagaga gggagtggcc aacccccccc  5160
cccccccccc tgcagcctgg cgtaatagcg aagaggcccg caccgatcgc ccttcccaac  5220
agttgcgtag cctgaatggc gaatggcgcg acgcgccctg tagcggcgca ttaagcgcgg  5280
cgggtgtggt ggttacgcgc agcgtgaccg ctacacttgc cagcgcccta gcgcccgctc  5340
ctttcgcttt cttcccttcc tttctcgcca cgttcgccgg ctttccccgt caagctctaa  5400
atcgggggct ccctttaggg ttccgattta gtgctttacg gcacctcgac cccaaaaaac  5460
ttgattaggg tgatggttca cgtagtgggc catcgccctg atagacggtt tttcgccctt  5520
tgacgttgga gtccacgttc tttaatagtg gactcttgtt ccaaactgga acaacactca  5580
accctatctc ggtctattct tttgatttat aagggatttt gccgatttcg gcctattggt  5640
```

```
taaaaaatga gctgatttaa caaaaattta acgcgaattt taacaaaata ttaacgttta  5700
caatttcctg atgcggtatt ttctccttac gcatctgtgc ggtatttcac accgcatatg  5760
gtgcactctc agtacaatct gctctgatgc cgcatagtta agccagcccc gacacccgcc  5820
aacacccgct gacgcgccct gacgggcttg tctgctcccg gcatccgctt acagacaagc  5880
tgtgaccgtc tccgggagct gcatgtgtca gaggttttca ccgtcatcac cgaaacgcgc  5940
gagacgaaag ggcctcgtga tacgcctatt tttataggtt aatgtcatga taataatggt  6000
ttcttagacg tcaggtggca cttttcgggg aaatgtgcgc ggaaccccta tttgtttatt  6060
tttctaaata cattcaaata tgtatccgct catgagacaa taaccctgat aaatgcttca  6120
ataatattga aaaaggaaga gtatgagtat tcaacatttc cgtgtcgccc ttattccctt  6180
ttttgcggca ttttgccttc ctgtttttgc tcacccagaa acgctggtga aagtaaaaga  6240
tgctgaagat cagttgggtg cacgagtggg ttacatcgaa ctggatctca acagcggtaa  6300
gatccttgag agttttcgcc ccgaagaacg ttttccaatg atgagcactt ttaaagttct  6360
gctatgtggc gcggtattat cccgtattga cgccgggcaa gagcaactcg gtcgccgcat  6420
acactattct cagaatgact tggttgagta ctcaccagtc acagaaaagc atcttacgga  6480
tggcatgaca gtaagagaat tatgcagtgc tgccataacc atgagtgata acactgcggc  6540
caacttactt ctgacaacga tcggaggacc gaaggagcta accgcttttt tgcacaacat  6600
gggggatcat gtaactcgcc ttgatcgttg ggaaccggag ctgaatgaag ccataccaaa  6660
cgacgagcgt gacaccacga tgcctgtagc aatggcaaca acgttgcgca aactattaac  6720
tggcgaacta cttactctag cttcccggca acaattaata gactggatgg aggcggataa  6780
agttgcagga ccacttctgc gctcggccct tccggctggc tggtttattg ctgataaatc  6840
tggagccggt gagcgtgggt ctcgcggtat cattgcagca ctggggccag atggtaagcc  6900
ctcccgtatc gtagttatct acacgacggg gagtcaggca actatggatg aacgaaatag  6960
acagatcgct gagataggtg cctcactgat taagcattgg taactgtcag accaagttta  7020
ctcatatata ctttagattg atttaaaact tcatttttaa tttaaaagga tctaggtgaa  7080
gatccttttt gataatctca tgaccaaaat cccttaacgt gagttttcgt tccactgagc  7140
gtcagacccc gtagaaaaga tcaaaggatc ttcttgagat cctttttttc tgcgcgtaat  7200
ctgctgcttg caaacaaaaa aaccaccgct accagcggtg gtttgtttgc cggatcaaga  7260
gctaccaact ctttttccga aggtaactgg cttcagcaga gcgcagatac caaatactgt  7320
ccttctagtg tagccgtagt taggccacca cttcaagaac tctgtagcac cgcctacata  7380
cctcgctctg ctaatcctgt taccagtggc tgctgccagt ggcgataagt cgtgtcttac  7440
cgggttggac tcaagacgat agttaccgga taaggcgcag cggtcgggct gaacgggggg  7500
ttcgtgcaca cagcccagct tggagcgaac gacctacacc gaactgagat acctacagcg  7560
tgagcattga gaaagcgcca cgcttcccga agggagaaag gcggacaggt atccggtaag  7620
cggcagggtc ggaacaggag agcgcacgag ggagcttcca gggggaaacg cctggtatct  7680
ttatagtcct gtcgggtttc gccacctctg acttgagcgt cgatttttgt gatgctcgtc  7740
aggggggcgg agcctatgga aaaacgccag caacgcggcc tttttacggt tcctggcctt  7800
ttgctggcct tttgctcaca tgttctttcc tgcgttatcc cctgattctg tggataaccg  7860
tattaccgcc tttgagtgag ctgataccgc tcgccgcagc cgaacgaccg agcgcagcga  7920
gtcagtgagc gaggaagcgg aagagcgccc aatacgcaaa ccgcctctcc ccgcgcgttg  7980
gccgattcat taatgcaggg ctgcag                                       8006

SEQ ID NO: 7            moltype = DNA  length = 3730
FEATURE                 Location/Qualifiers
misc_feature            1..3730
                        note = SARS-CoV-2 Spike Protein deleted TM domain
source                  1..3730
                        mol_type = other DNA
                        organism = synthetic construct
SEQUENCE: 7
agcttgaatt cgccaccatg ttcgtgtttc tggtgctgct gcctctggtg tccagccagt  60
gtgtgaacct gaccaccaga acacagctgc ctccagccta caccaacagc tttaccagag  120
gcgtgtacta ccccgacaag gtgttcagat ccagcgtgct gcactctacc caggacctgt  180
tcctgccttt cttcagcaac gtgacctggt tccacgccat ccacgtgtcc ggcaccaatg  240
gcaccaagag attcgacaac cccgtgctgc ccttcaacga cggggtgtac tttgccagca  300
ccgagaagtc caacatcatc agaggctgga tcttcggcac cacactggac agcaagaccc  360
agagcctgct gatcgtgaac aacgccacca acgtggtcat caaagtgtgc gagttccagt  420
tctgcaacga ccccttcctg ggcgtctact accacaagaa caacaagagc tggatggaaa  480
gcgagttccg ggtgtacagc agcgccaaca actgcacctt cgagtacgtg tcccagcctt  540
tcctgatgga cctggaaggc aagcagggca acttcaagaa cctgcgcgag ttcgtgttca  600
agaacatcga cggctacttc aagatctaca gcaagcacac ccctatcaac ctcgtgcggg  660
atctgcctca gggcttctct gctctggaac ccctggtgga tctgcccatc ggcatcaaca  720
tcacccggtt tcagacactg ctggccctgc acagaagcta cctgacacct ggcgatagca  780
gcagcggatg gacagctggt gccgccgctt actatgtggg ctacctgcag cctagaacct  840
tcctgctgaa gtacaacgag aacggcacca tcaccgacgc cgtggattgt gctctggatc  900
ctctgagcga gacaaagtgc accctgaagt ccttcaccgt ggaaaagggc atctaccaga  960
ccagcaactt ccgggtgcag cccaccgaat ccatcgtgcg gttccccaat atcaccaatc  1020
tgtgcccctt cggcgaggtg ttcaatgcca ccagattcgc ctctgtgtac gcctggaacc  1080
ggaagcggat cagcaattgc gtggccgact actccgtgct gtacaactcc gccagcttca  1140
gcaccttcaa gtgctacggc gtgtccccta ccaagctgaa cgacctgtgc ttcacaaacg  1200
tgtacgccga cagcttcgtg atccggggag atgaagtgcg gcagattgcc cctggacaga  1260
caggcaagat cgccgactac aactacaagc tgcccgacga cttcaccggc tgtgtgattg  1320
cctggaacag caacaacctg gactccaaag tcggcggcaa ctacaattac ctgtaccggc  1380
tgttccggaa gtccaatctg aagcccttcg agcgggacat ctccaccgag atctatcagg  1440
ccggcagcac cccttgtaac ggcgtggaag gcttcaactg ctacttccca ctgcagtcct  1500
acggctttca gcccacaaat ggcgtgggct atcagcccta cagagtggtg gtgctgagct  1560
tcgaactgct gcatgcccct gccacagtgt gcggccctaa gaaaagcacc aatctcgtga  1620
agaacaaatg cgtgaacttc aacttcaacg gcctgaccgg caccggcgtg ctgacagaga  1680
gcaacaagaa gttcctgcca ttccagcagt ttggccggga tatcgccgat accacagacg  1740
ccgttagaga tccccagaca ctggaaatcc tggacatcac cccttgcagc ttcggcggag  1800
```

```
tgtctgtgat caccccctggc accaacacca gcaatcaggt ggcagtgctg taccaggacg  1860
tgaactgtac cgaagtgccc gtggccattc acgccgatca gctgacacct acatggcggg  1920
tgtactccac cggcagcaat gtgtttcaga ccagagccgg ctgtctgatc ggagccgagc  1980
acgtgaacaa tagctacgag tgcgacatcc ccatcggcgc tggcatctgt gccagctacc  2040
agacacagac aaacagcccc agacgggcca gatctgtggc cagccagagc atcattgcct  2100
acacaatgtc tctgggcgcc gagaacagcg tggcctactc caacaactct atcgctatcc  2160
ccaccaactt caccatcagc gtgaccacag agatcctgcc tgtgtccatg accaagacca  2220
gcgtggactg caccatgtac atctgcggcg attccaccga gtgctccaac ctgctgctgc  2280
agtacggcag cttctgcacc cagctgaata gagccctgac agggatcgcc gtggaacagg  2340
acaagaacac ccaagaggtg ttcgcccaag tgaagcagat ctacaagacc cctcctatca  2400
aggacttcgg cggcttcaat ttcagccaga ttctgcccga tcctagcaag cccagcaagc  2460
ggagcttcat cgaggacctg ctgttcaaca aagtgacact ggccgacgcc ggcttcatca  2520
agcagtatgg cgattgtctg ggcgacattg ccgccaggga tctgatttgc gcccagaagt  2580
ttaacggact gacagtgctg cctcctctgc tgaccgatga gatgatcgcc cagtacacat  2640
ctgccctgct ggccggcaca atcacaagcg gctggacatt tggagctggc gccgctctgc  2700
agatcccctt tgctatgcag atggcctacc ggttcaacgg catcggagtg acccagaatg  2760
tgctgtacga gaaccagaag ctgatcgcca accagttcaa cagcgccatc ggcaagatcc  2820
aggacagcct gagcagcaca gcaagcgccc tgggaaagct gcaggacgtg gtcaaccaga  2880
atgcccaggc actgaacacc ctggtcaagc agctgtcctc caacttcggc gccatcagct  2940
ctgtgctgaa cgatatcctg agcagactgg accctcctga ggccgaggtg cagatcgaca  3000
gactgatcac aggcagactg cagagcctcc agacatacgt gacccagcag ctgatcagag  3060
ccgccgagat tagagcctct gccaatctgg ccgccaccaa gatgtctgag tgtgtgctgg  3120
gccagagcaa gagagtggac ttttgcggca agggctacca cctgatgagc ttccctcagt  3180
ctgcccctca cggcgtggtg tttctgcacg tgacatatgt gcccgctcaa gagaagaatt  3240
tcaccaccgc tccagccatc tgccacgacg gcaaagccca ctttcctaga gaaggcgtgt  3300
tcgtgtccaa cggcacccat tggttcgtga cacagcggaa cttctacgag ccccagatca  3360
tcaccaccga caacaccttc gtgtctggca actgcgacgt cgtgatcggc attgtgaaca  3420
ataccgtgta cgaccctctg cagcccgagc tggacagctt caaagaggaa ctggacaagt  3480
actttaagaa ccacacaagc cccgacgtgg acctgggcga tatcagcgga atcaatgcca  3540
gcgtcgtgaa catccagaaa gagatcgacc ggctgaacga ggtggccaag aatctgaacg  3600
agagcctgat cgacctgcaa gaactgggga agtacgaggg ctacatccct gaggctccta  3660
gagatggcca ggcctacgtc agaaaggatg gcgagtgggt cctgctgagc accttcctgt  3720
aatctagagc                                                        3730
```

```
SEQ ID NO: 8            moltype = DNA  length = 7895
FEATURE                 Location/Qualifiers
misc_feature            1..7895
                        note = p-TR-SARS2-2P-dTM
source                  1..7895
                        mol_type = other DNA
                        organism = synthetic construct
SEQUENCE: 8
gggggggggg gggggggttg gccactccct ctctgcgcgc tcgctcgctc actgaggccg  60
ggcgaccaaa ggtcgcccga cgcccgggct ttgcccgggc ggcctcagtg agcgagcgag  120
cgcgcagaga gggagtggcc aactccatca ctaggggttc ctagatcttc aatattggcc  180
attagccata ttattcattg gttatatagc ataaatcaat attggctatt ggccattgca  240
tacgttgtat ctatatcata atatgtacat ttatattggc tcatgtccaa tatgaccgcc  300
atgttggcat tgattattga ctagttatta atagtaatca attacggggt cattagttca  360
tagcccatat atggagttcc gcgttacata acttacggta aatggcccgc ctggctgacc  420
gcccaacgac ccccgcccat tgacgtcaat aatgacgtat gttcccatag taacgccaat  480
agggactttc cattgacgtc aatgggtgga gtatttacgg taaactgccc acttggcagt  540
acatcaagtg tatcatatgc caagtccgcc ccctattgac gtcaatgacg gtaaatggcc  600
cgcctggcat tatgcccagt acatgacctt acgggacttt cctacttggc agtacatcta  660
cgtattagtc atcgctatta ccatggtgat gcggttttgg cagtacacca atgggcgtgg  720
atagcggttt gactcacggg gatttccaag tctccacccc attgacgtca atgggagttt  780
gttttggcac caaaatcaac gggactttcc aaaatgtcgt aataaccccg ccccgttgac  840
gcaaatgggc ggtaggcgtg tacggtggga ggtctatata agcagagctc gtttagtgaa  900
ccgtcagatc actagaagct tgaattcgcc accatgttcg tgtttctggt gctgctgcct  960
ctggtgtcca gccagtgtgt gaacctgacc accagaacac agctgcctcc agcctacacc  1020
aacagcttta ccagaggcgt gtactacccc gacaaggtgt tcagatccag cgtgctgcac  1080
tctacccagg acctgttcct gcctttcttc agcaacgtga cctggttcca cgccatccac  1140
gtgtccggca ccaatggcac caagagattc gacaaccccg tgctgccctt caacgacggg  1200
gtgtactttg ccagcaccga gaagtccaac atcatcagag gctggatctt cggcaccaca  1260
ctggacagca agacccagag cctgctgatc gtgaacaacg ccaccaacgt ggtcatcaaa  1320
gtgtgcgagt tccagttctg caacgacccc ttcctgggcg tctactacca caagaacaac  1380
aagagctgga tggaaagcga gttccgggtg tacagcagcg ccaacaactg caccttcgag  1440
tacgtgtccc agcctttcct gatggacctg gaaggcaagc agggcaactt caagaacctg  1500
cgcgagttcg tgttcaagaa catcgacggc tacttcaaga tctacagcaa gcacacccct  1560
atcaacctcg tgcgggatct gcctcagggc ttctctgctc tggaacccct ggtggatctg  1620
cccatcggca tcaacatcac ccggtttcag acactgctgg ccctgcacag aagctacctg  1680
acacctggcg atagcagcag cggatggaca gctggtgccg ccgcttacta tgtgggctac  1740
ctgcagccta gaaccttcct gctgaagtac aacgagaacg gcaccatcac cgacgccgtg  1800
gattgtgctc tggatcctct gagcgagaca aagtgcaccc tgaagtcctt caccgtggaa  1860
aagggcatct accagaccag caacttccgg gtgcagccca ccgaatccat cgtgcggttc  1920
cccaatatca ccaatctgtg ccccttcggc gaggtgttca atgccaccag attcgcctct  1980
gtgtacgcct ggaaccggaa gcggatcagc aattgcgtgg ccgactactc cgtgctgtac  2040
aactccgcca gcttcagcac cttcaagtgc tacggcgtgt cccctaccaa gctgaacgac  2100
ctgtgcttca caaacgtgta cgccgacagc ttcgtgatcc ggggagatga agtgcggcag  2160
attgcccctg gacagacagg caagatcgcc gactacaact acaagctgcc cgacgacttc  2220
```

-continued

```
accggctgtg tgattgcctg gaacagcaac aacctggact ccaaagtcgg cggcaactac  2280
aattacctgt accggctgtt ccggaagtcc aatctgaagc ccttcgagcg ggacatctcc  2340
accgagatct atcaggccgg cagcacccct tgtaacggcg tggaaggctt caactgctac  2400
ttcccactgc agtcctacgg ctttcagccc acaaatggcg tgggctatca gccctacaga  2460
gtggtggtgc tgagcttcga actgctgcat gcccctgcca cagtgtgcgg ccctaagaaa  2520
agcaccaatc tcgtgaagaa caaatgcgtg aacttcaact tcaacggcct gaccggcacc  2580
ggcgtgctga cagagagcaa caagaagttc ctgccattcc agcagtttgg ccgggatatc  2640
gccgatacca cagacgccgt tagagatccc cagacactgg aaatcctgga catcacccct  2700
tgcagcttcg gcggagtgtc tgtgatcacc cctggcacca acaccagcaa tcaggtggca  2760
gtgctgtacc aggacgtgaa ctgtaccgaa gtgcccgtgg ccattcacgc cgatcagctg  2820
acacctacat ggcgggtgta ctccaccggc agcaatgtgt ttcagaccag agccggctgt  2880
ctgatcggag ccgagcacgt gaacaatagc tacgagtgcg acatccccat cggcgctggc  2940
atctgtgcca gctaccagac acagacaaac agccccagac gggccagatc tgtggccagc  3000
cagagcatca ttgcctacac aatgtctctg ggcgccgaga acagcgtggc ctactccaac  3060
aactctatcg ctatccccac caacttcacc atcagcgtga ccacagagat cctgcctgtg  3120
tccatgacca agaccagcgt ggactgcacc atgtacatct gcggcgattc caccgagtgc  3180
tccaacctgc tgctgcagta cggcagcttc tgcacccagc tgaatagagc cctgacaggg  3240
atcgccgtgg aacaggacaa gaacacccaa gaggtgttcg cccaagtgaa gcagatctac  3300
aagacccctc ctatcaagga cttcggcggc ttcaatttca gccagattct gcccgatcct  3360
agcaagccca gcaagcggag cttcatcgag gacctgctgt tcaacaaagt gacactggcc  3420
gacgccggct tcatcaagca gtatggcgat tgtctgggcg acattgccgc cagggatctg  3480
atttgcgccc agaagtttaa cggactgaca gtgctgcctc ctctgctgac cgatgagatg  3540
atcgcccagt acacatctgc cctgctggcc ggcacaatca caagcggctg gacatttgga  3600
gctggcgccg ctctgcagat ccccttttgct atgcagatgg cctaccggtt caacggcatc  3660
ggagtgaccc agaatgtgct gtacgagaac cagaagctga tcgccaacca gttcaacagc  3720
gccatcggca agatccagga cagcctgagc agcacagcaa gcgccctggg aaagctgcag  3780
gacgtggtca accagaatgc ccaggcactg aacaccctgg tcaagcagct gtcctccaac  3840
ttcggcgcca tcagctctgt gctgaacgat atcctgagca gactggaccc tcctgaggcc  3900
gaggtgcaga tcgacagact gatcacaggc agactgcaga gcctccagac atacgtgacc  3960
cagcagctga tcagagccgc cgagattaga gcctctgcca atctggccgc caccaagatg  4020
tctgagtgtg tgctgggcca gagcaagaga gtggactttt gcggcaaggg ctaccacctg  4080
atgagcttcc ctcagtctgc ccctcacggc gtggtgtttc tgcacgtgac atatgtgccc  4140
gctcaagaga agaatttcac caccgctcca gccatctgcc acgacggcaa agcccacttt  4200
cctagagaag gcgtgttcgt gtccaacggc acccattggt tcgtgacaca gcggaacttc  4260
tacgagcccc agatcatcac caccgacaac accttcgtgt ctggcaactg cgacgtcgtg  4320
atcggcattg tgaacaatac cgtgtacgac cctctgcagc ccgagctgga cagcttcaaa  4380
gaggaactgg acaagtactt taagaaccac acaagccccg acgtggacct gggcgatatc  4440
agcggaatca atgccagcgt cgtgaacatc cagaaagaga tcgaccggct gaacgaggtg  4500
gccaagaatc tgaacgagag cctgatcgac ctgcaagaac tggggaagta cgagggctac  4560
atccctgagg ctcctagaga tggccaggcc tacgtcagaa aggatggcga gtgggtcctg  4620
ctgagcacct tcctgtaatc tagagcggcc gcttcgagca gacatgataa gatacattga  4680
tgagtttgga caaaccacaa ctagaatgca gtgaaaaaaa tgctttattt gtgaaatttg  4740
tgatgctatt gctttatttg taaccattat aagctgcaat aaacaagtta acaacaacaa  4800
ttgcattcat tttatgtttc aggttcaggg ggagatgtgg gaggtttttt aaagcaagta  4860
aaacctctac aaatgtggta aaatcgataa ggatctagga acccctagtg atggagttgg  4920
ccactccctc tctgcgcgct cgctcgctca ctgaggccgc ccgggcaaag cccgggcgtc  4980
gggcgacctt tggtcgcccg gcctcagtga gcgagcgagc gcgcagagag ggagtggcca  5040
accccccccc cccccccccct gcagcctggc gtaatagcga agaggcccgc accgatcgcc  5100
cttcccaaca gttgcgtagc ctgaatggcg aatggcgcga cgcgccctgt agcggcgcat  5160
taagcgcggc gggtgtggtg gttacgcgca gcgtgaccgc tacacttgcc agcgccctag  5220
cgcccgctcc tttcgctttc ttcccttcct ttctcgccac gttcgccggc tttccccgtc  5280
aagctctaaa tcgggggctc cctttagggt tccgatttag tgctttacgg cacctcgacc  5340
ccaaaaaact tgattagggt gatggttcac gtagtgggcc atcgccctga tagacggttt  5400
ttcgcccttt gacgttggag tccacgttct ttaatagtgg actcttgttc caaactggaa  5460
caacactcaa ccctatctcg gtctattctt ttgatttata agggattttg ccgatttcgg  5520
cctattggtt aaaaaatgag ctgatttaac aaaaatttaa cgcgaatttt aacaaaatat  5580
taacgtttac aatttcctga tgcggtattt tctccttacg catctgtgcg gtatttcaca  5640
ccgcatatgg tgcactctca gtacaatctg ctctgatgcc gcatagttaa gccagccccg  5700
acacccgcca acacccgctg acgcgccctg acgggcttgt ctgctcccgg catccgctta  5760
cagacaagct gtgaccgtct ccgggagctg catgtgtcag aggttttcac cgtcatcacc  5820
gaaacgcgcg agacgaaagg gcctcgtgat acgcctattt ttataggtta atgtcatgat  5880
aataatggtt tcttagacgt caggtggcac ttttcgggga aatgtgcgcg gaacccctat  5940
ttgtttattt ttctaaatac attcaaatat gtatccgctc atgagacaat aaccctgata  6000
aatgcttcaa taatattgaa aaaggaagag tatgagtatt caacatttcc gtgtcgccct  6060
tattcccttt tttgcggcat tttgccttcc tgtttttgct cacccagaaa cgctggtgaa  6120
agtaaaagat gctgaagatc agttgggtgc acgagtgggt tacatcgaac tggatctcaa  6180
cagcggtaag atccttgaga gttttcgccc cgaagaacgt tttccaatga tgagcacttt  6240
taaagttctg ctatgtggcg cggtattatc ccgtattgac gccgggcaag agcaactcgg  6300
tcgccgcata cactattctc agaatgactt ggttgagtac tcaccagtca cagaaaagca  6360
tcttacggat ggcatgacag taagagaatt atgcagtgct gccataacca tgagtgataa  6420
cactgcggcc aacttacttc tgacaacgat cggaggaccg aaggagctaa ccgctttttt  6480
gcacaacatg ggggatcatg taactcgcct tgatcgttgg gaaccggagc tgaatgaagc  6540
cataccaaac gacgagcgtg acaccacgat gcctgtagca atggcaacaa cgttgcgcaa  6600
actattaact ggcgaactac ttactctagc ttcccggcaa caattaatag actggatgga  6660
ggcggataaa gttgcaggac cacttctgcg ctcggccctt ccggctggct ggtttattgc  6720
tgataaatct ggagccggtg agcgtgggtc tcgcggtatc attgcagcac tggggccaga  6780
tggtaagccc tcccgtatcg tagttatcta cacgacgggg agtcaggcaa ctatggatga  6840
acgaaataga cagatcgctg agataggtgc ctcactgatt aagcattggt aactgtcaga  6900
ccaagtttac tcatatatac tttagattga tttaaaactt catttttaat ttaaaaggat  6960
```

```
ctaggtgaag atcctttttg ataatctcat gaccaaaatc ccttaacgtg agttttcgtt  7020
ccactgagcg tcagaccccg tagaaaagat caaaggatct tcttgagatc cttttttct  7080
gcgcgtaatc tgctgcttgc aaacaaaaaa accaccgcta ccagcggtgg tttgtttgcc  7140
ggatcaagag ctaccaactc tttttccgaa ggtaactggc ttcagcagag cgcagatacc  7200
aaatactgtc cttctagtgt agccgtagtt aggccaccac ttcaagaact ctgtagcacc  7260
gcctacatac ctcgctctgc taatcctgtt accagtggct gctgccagtg gcgataagtc  7320
gtgtcttacc gggttggact caagacgata gttaccggat aaggcgcagc ggtcgggctg  7380
aacggggggt tcgtgcacac agcccagctt ggagcgaacg acctacaccg aactgagata  7440
cctacagcgt gagcattgag aaagcgccac gcttcccgaa gggagaaagg cggacaggta  7500
tccggtaagc ggcagggtcg gaacaggaga gcgcacgagg gagcttccag ggggaaacgc  7560
ctggtatctt tatagtcctg tcgggtttcg ccacctctga cttgagcgtc gatttttgtg  7620
atgctcgtca ggggggcgga gcctatggaa aaacgccagc aacgcggcct ttttacggtt  7680
cctggccttt tgctggcctt ttgctcacat gttctttcct gcgttatccc ctgattctgt  7740
ggataaccgt attaccgcct ttgagtgagc tgataccgct cgccgcagcc gaacgaccga  7800
gcgcagcgag tcagtgagcg aggaagcgga agagcgccca atacgcaaac cgcctctccc  7860
cgcgcgttgg ccgattcatt aatgcagggc tgcag                             7895

SEQ ID NO: 9           moltype = DNA  length = 748
FEATURE                Location/Qualifiers
misc_feature           1..748
                       note = CMV Promoter
source                 1..748
                       mol_type = other DNA
                       organism = synthetic construct
SEQUENCE: 9
tcaatattgg ccattagcca tattattcat tggttatata gcataaatca atattggcta  60
ttggccattg catacgttgt atctatatca taatatgtac atttatattg gctcatgtcc  120
aatatgaccg ccatgttggc attgattatt gactagttat taatagtaat caattacggg  180
gtcattagtt catagcccat atatggagtt ccgcgttaca taacttacgg taaatggccc  240
gcctggctga ccgcccaacg acccccgccc attgacgtca ataatgacgt atgttcccat  300
agtaacgcca atagggactt tccattgacg tcaatgggtg gagtatttac ggtaaactgc  360
ccacttggca gtacatcaag tgtatcatat gccaagtccg ccccctattg acgtcaatga  420
cggtaaatgg cccgcctggc attatgccca gtacatgacc ttacgggact ttcctacttg  480
gcagtacatc tacgtattag tcatcgctat taccatggtg atgcggtttt ggcagtacac  540
caatgggcgt ggatagcggt ttgactcacg gggatttcca agtctccacc ccattgacgt  600
caatgggagt ttgttttggc accaaaatca acgggacttt ccaaaatgtc gtaataaccc  660
cgccccgttg acgcaaatgg gcggtaggcg tgtacggtgg gaggtctata taagcagagc  720
tcgtttagtg aaccgtcaga tcactaga                                    748

SEQ ID NO: 10          moltype = DNA  length = 7363
FEATURE                Location/Qualifiers
misc_feature           1..7363
                       note = AAV plasmid sequence
source                 1..7363
                       mol_type = other DNA
                       organism = synthetic construct
SEQUENCE: 10
ttaattaact gcagacgcca gctgttggcc actccctctc tgcgcgctcg ctcgctcact  60
gaggccgggc gaccaaaggt cgcccgacgc ccgggctttg cccgggcggc ctcagtgagc  120
gagcgagcgc gcagagaggg agtggccaac tccatcacta ggggttcctt ctagaggcgc  180
gccaagcttc cctaaaatgg gcaaacattg caagcagcaa acagcaaaca cacagccctc  240
cctgcctgct gaccttggag ctggggcaga ggtcagagac ctctctgggg actgtcccag  300
gtcagtggtg gtgcctgaag ctgaggagac agggccctgt cctcgtccgt atttaagcag  360
tggatccaga ggggcaacgg gggaggctgc tggtgaatat taaccaaggt caccccagtt  420
atcggaggag caaacagggg ctaagtccac tggctgggat ctgagtcgcc cgcctacgct  480
gcccggacgc tttgcctggg cagtgtacag cttccactgc acttaccgaa aggagtcatt  540
gtagggccct gtctcctcag cttcaggcac caccactgac ctgggacagt gaatccggaa  600
ctagtaagta tcaaggttac aagacaggtt taaggagacc aatagaaact gggcttgtcg  660
agacagagaa gactcttgcg tttctgatag gcacctattg gtcttactga catccacttt  720
gcctttctct ccacaggcta gcatttaaat caggtatggc tgccgatggt tatcttccag  780
attggctcga ggacaacctt agtgaaggaa ttcgcgagtg gtgggctttg aaacctggag  840
cccctcaacc caaggcaaat caacaacatc aagacaacgc tcgaggtctt gtgcttccgg  900
gttacaaata ccttggaccc ggcaacggac tcgacaaggg ggagccggtc aacgcagcag  960
acgcggcggc cctcgagcac gacaaggcct acgaccagca gctcaaggcc ggagacaacc  1020
cgtacctcaa gtacaaccac gccgacgccg agttccagga gcggctcaaa gaagatacgt  1080
cttttggggg caacctcggg cgagcagtct tccaggccaa aaagaggctt cttgaacctc  1140
ttggtctggt tgaggaagcg gctaagacgg ctcctggaaa gaagaggcct gtagagcagt  1200
ctcctcagga accggactcc tccgcgggta ttggcaaatc gggtgcacag cccgctaaaa  1260
agagactcaa tttcggtcag actggcgaca cagagtcagt cccagaccct caaccaatcg  1320
gagaacctcc cgcagccccc tcaggtgtgg gatctcttac aatggcttca ggtggtggcg  1380
caccagtggc agacaataac gaaggtgccg atggagtggg tagttcctcg ggaaattggc  1440
attgcgattc ccaatggctg gggacagag tcatcaccac cagcacccga acctgggccc  1500
tgcccaccta caacaatcac ctctacaagc aaatctccaa cagcacatct ggaggatctt  1560
caaatgacaa cgcctacttc ggctacagca ccccctgggg gtattttgac ttcaacagat  1620
tccactgcca cttctcacca cgtgactggc agcgactcat caacaacaac tggggattcc  1680
ggcctaagcg actcaacttc aagctcttca acattcaggt caaagaggtt acggacaaca  1740
atggagtcaa gaccatcgcc aataacctta ccagcacggt ccaggtcttc acggactcag  1800
actatcagct cccgtacgtg ctcgggtcgg ctcacgaggg ctgcctcccg ccgttcccag  1860
cggacgtttt catgattcct cagtacgggt atctgacgct taatgatgga agccaggccg  1920
```

-continued

```
tgggtcgttc gtccttttac tgcctggaat atttcccgtc gcaaatgcta agaacgggta  1980
acaacttcca gttcagctac gagtttgaga acgtaccttt ccatagcagc tacgctcaca  2040
gccaaagcct ggaccgacta atgaatccac tcatcgacca atacttgtac tatctctcaa  2100
agactattaa cggttctgga cagaatcaac aaacgctaaa attcagtgtg gccggaccca  2160
gcaacatggc tgtccaggga agaaactaca tacctggacc cagctaccga caacaacgtg  2220
tctcaaccac tgtgactcaa aacaacaaca gcgaatttgc ttggcctgga gcttcttctt  2280
gggctctcaa tggacgtaat agcttgatga atcctggacc tgctatggcc agccacaaag  2340
aaggagagga ccgtttcttt cctttgtctg gatctttaat ttttggcaaa caaggaactg  2400
gaagagacaa cgtggatgcg gacaaagtca tgataaccaa cgaagaagaa attaaaacta  2460
ctaacccggt agcaacggag tcctatggac aagtggccac aaaccaccag agtgcccaag  2520
cacaggcgca gaccggctgg gttcaaaacc aaggaatact tccgggtatg gtttggcagg  2580
acagagatgt gtacctgcaa ggacccattt gggccaaaat tcctcacacg gacggcaact  2640
ttcacccttc tccgctgatg ggagggtttg gaatgaagca cccgcctcct cagatcctca  2700
tcaaaaacac acctgtacct gcggatcctc caacggcctt caacaaggac aagctgaact  2760
ctttcatcac ccagtattct actggccaag tcagcgtgga gatcgagtgg gagctgcaga  2820
aggaaaacag caagcgctgg aacccggaga tccagtacac ttccaactat tacaagtcta  2880
ataatgttga atttgctgtt aatactgaag gtgtatatag tgaaccccgc cccattggca  2940
ccagatacct gactcgtaat ctgtaattgc ttgttaatca ataaaccgtt taattcgttt  3000
cagttgaact ttggtctctg cgtatttctt tcttatctag tttccatgct ctaggcggcc  3060
gcctcgagct gtgccttcta gttgccagcc atctgttgtt tgcccctccc ccgtgccttc  3120
cttgaccctg gaaggtgcca ctcccactgt cctttcctaa taaaatgagg aaattgcatc  3180
gcattgtctg agtaggtgtc attctattct ggggggtggg gtggggcagg acagcaaggg  3240
ggaggattgg gaagacaata gcaggcatgc tggggagtcg acgcgccggc gtctagaagg  3300
aacccctagt gatggagttg gccactccct ctctgcgcgc tcgctcgctc actgaggccg  3360
ggcgaccaaa ggtcgcccga cgcccgggct ttgcccgggc ggcctcagtg agcgagcgag  3420
cgcgcagaga gggagtggcc aacagctgca ttaatgaatc ctgcaggcgg ccaacgcgcg  3480
gggagaggcg gtttgcgtat tgggcgctct tccgcttcct cgctcactga ctcgctgcgc  3540
tcggtcgttc ggctgcggcg agcggtatca gctcactcaa aggcggtaat acggttatcc  3600
acagaatcag gggataacgc aggaaagaac atgtgagcaa aaggccagca aaaggccagg  3660
aaccgtaaaa aggccgcgtt gctggcgttt ttccataggc tccgcccccc tgacgagcat  3720
cacaaaaatc gacgctcaag tcagaggtgg cgaaacccga caggactata aagataccag  3780
gcgtttcccc ctggaagctc cctcgtgcgc tctcctgttc cgaccctgcc gcttaccgga  3840
tacctgtccg cctttctccc ttcgggaagc gtggcgcttt ctcatagctc acgctgtagg  3900
tatctcagtt cggtgtaggt cgttcgctcc aagctgggct gtgtgcacga accccccgtt  3960
cagcccgacc gctgcgcctt atccggtaac tatcgtcttg agtccaaccc ggtaagacac  4020
gacttatcgc cactggcagc agccactggt aacaggatta gcagagcgag gtatgtaggc  4080
ggtgctacag agttcttgaa gtggtggcct aactacggct acactagaag aacagtattt  4140
ggtatctgcg ctctgctgaa gccagttacc ttcggaaaaa gagttggtag ctcttgatcc  4200
ggcaaacaaa ccaccgctgg tagcggtggt ttttttgttt gcaagcagca gattacgcgc  4260
agaaaaaaag gatctcaaga agatcctttg atcttttcta cggggtctga cgctcagtgg  4320
aacgaaaact cacgttaagg gattttggtc atgacactac gtgttaccaa tgcttaatca  4380
gtgaggcacc tatctcagcg atctgtctat ttcgttcatc catagttgcc tgactccccg  4440
tcgtgtagat aactacgata cgggagggct taccatctgg ccccagtgct gcaatgatac  4500
cgcgagaccc acgctcaccg gctccagatt tatcagcaat aaaccagcca gccggaaggg  4560
ccgagcgcag aagtggtcct gcaactttat ccgcctccat ccagtctatt aattgttgcc  4620
gggaagctag agtaagtagt tcgccagtta atagtttgcg caacgttgtt gccattgcta  4680
caggcatcgt ggtgtcacgc tcgtcgtttg gtatggcttc attcagctcc ggttcccaac  4740
gatcaaggcg agttacatga tcccccatgt tgtgcaaaaa agcggttagc tccttcggtc  4800
ctccgatcgt tgtcagaagt aagttggccg cagtgttatc actcatggtt atggcagcac  4860
tgcataattc tcttactgtc atgccatccg taagatgctt ttctgtgact ggtgagtact  4920
caaccaagtc attctgagaa tagtgtatgc ggcgaccgag ttgctcttgc ccggcgtcaa  4980
tacgggataa taccgcgcca catagcagaa ctttaaaagt gctcatcatt ggaaaacgtt  5040
cttcggggcg aaaactctca aggatcttac cgctgttgag atccagttcg atgtaaccca  5100
ctcgtgcacc caactgatct tcagcatctt ttactttcac cagcgtttct gggtgagcaa  5160
aaacaggaag gcaaaatgcc gcaaaaaagg gaataagggc gacacggaaa tgttgaatac  5220
tcatactctt cctttttcaa tattattgaa gcatttatca gggttattgt ctctatgagc  5280
ggatacatat ttgaatgtat ttagaaaaat aaacaaatag gggttccgcg cactacgtgg  5340
gatcctcatg agattatcaa aaaggatctt cacctagatc cttttcacgt agaaagccag  5400
tccgcagaaa cggtgctgac cccctgaggc ggaaagaacc agctgtggaa tgtgtgtcag  5460
ttagggtgtg gaaagtcccc aggctcccca gcaggcagaa gtatgcaaag catgcatctc  5520
aattagtcag caaccaggtg tggaaagtcc ccaggctccc cagcaggcag aagtatgcaa  5580
agcatgcatc tcaattagtc agcaaccata gtcccgcccc taactccgcc catcccgccc  5640
ctaactccgc ccagttccgc ccattctccg ccccatggct gactaatttt ttttatttat  5700
gcagaggccg aggccgcctc ggcctctgag ctattccaga agtagtgagg aggctttttt  5760
ggaggcctag gcttttgcaa aggatgaatg tcagctactg ggctatctgg acaagggaaa  5820
acgcaagcgc aaagagaaag caggtagctt gcagtgggct tacatggcga tagctagact  5880
gggcggtttt atggacagca agcgaaccgg aattgccagc tggggcgccc tctggtaagg  5940
ttgggaagcc ctgcaaagta aactggatgg ctttcttgcc gccaaggatc tgatggcgca  6000
ggggatcaag ctctgatcaa gagacaggat gaggatcgtt tcgcatgatt gaacaagatg  6060
gattgcacgc aggttctccg gccgcttggg tggagaggct attcggctat gactgggcac  6120
aacagacaat cggctgctct gatgccgccg tgttccggct gtcagcgcag gggcgcccgg  6180
ttctttttgt caagaccgac ctgtccggtg ccctgaatga actgcaagac gaggcagcgc  6240
ggctatcgtg gctggccacg acgggcgttc cttgcgcagc tgtgctcgac gttgtcactg  6300
aagcgggaag ggactggctg ctattgggcg aagtgccggg gcaggatctc ctgtcatctc  6360
accttgctcc tgccgagaaa gtatccatca tggctgatgc aatgcggcgg ctgcatacgc  6420
ttgatccggc tacctgccca ttcgaccacc aagcgaaaca tcgcatcgag cgagcacgta  6480
ctcggatgga agccggtctt gtcgatcagg atgatctgga cgaagagcat caggggctcg  6540
cgccagccga actgttcgcc aggctcaagg cgagcatgcc cgacggcgag gatctcgtcg  6600
tgacccatgg cgatgcctgc ttgccgaata tcatggtgga aaatggccgc ttttctggat  6660
```

-continued

```
tcatcgactg tggccggctg ggtgtggcgg accgctatca ggacatagcg ttggctaccc  6720
gtgatattgc tgaagagctt ggcggcgaat gggctgaccg cttcctcgtg ctttacggta  6780
tcgccgctcc cgattcgcag cgcatcgcct tctatcgcct tcttgacgag ttcttctgaa  6840
ttttcacaca aaaaaccaac acacagatgt aatgaaaata aagatatttt attgttaaaa  6900
tttttgttaa atcagctcat tttttaacca ataggccgaa atcggcaaaa tcccttataa  6960
atcaaaagaa tagaccgaga tagggttgag tgttgttcca gtttggaaca agagtccact  7020
attaaagaac gtggactcca acgtcaaagg gcgaaaaacc gtctatcagg gcgatggccc  7080
ctcgaggaac catcacccta atcaagtttt ttggggtcga ggtgccgtaa agcactaaat  7140
cggaacccta aagggagccc ccgatttaga gcttgacggg gaaagccggc gaacgtggcg  7200
agaaaggaag ggaagaaagc gaaaggagcg ggcgctaggg cgctggcaag tgtagcggtc  7260
acgctgcgcg taaccaccac acccgccgcg cttaatgcgc cgctacaggg cgcgtcgcgt  7320
ccattcgcca ttcaggctgc gcaactgttg ggaagggctg cag                     7363
```

METHODS OF TOLERIZING A SUBJECT TO A VIRAL VECTOR

CROSS-REFERENCE TO RELATED APPLICATION

This application claims the benefit of U.S. Provisional Application No. 63/351,079, filed Jun. 10, 2022, which is incorporated herein by reference.

SEQUENCE LISTING

This application incorporates by reference the Sequence Listing contained in the following XML file being submitted concurrently herewith: File Name: T18455_SeqList.xml; was created May 31, 2023, and is 53 KB in size.

BACKGROUND

Gene therapy provides successful therapy for a number of diseases or conditions. However, immune responses to viral vectors can present potential limitations on repeated administration of a therapeutic viral vector.

SUMMARY

Described are methods for inducing immune tolerance to a viral vector such as a therapeutic recombinant adeno-associated virus (rAAV). The therapeutic (first) rAAV can encode a therapeutic nucleic acid. Viral gene therapy may require repeat administrations of a therapeutic rAAV. However, some patients may develop an immune reaction to subsequent administrations of the therapeutic rAAV, which can limit the use of the therapeutic rAAV to deliver a therapeutic nucleic acid. As further described herein, administering to the subject a second rAAV of a serotype different from that of the rAAV encoding the therapeutic transgene (first rAAV) and encoding at least a portion of a capsid protein of the first rAAV induces specific immune tolerance to the rAAV encoding the therapeutic transgene (first rAAV), thereby providing for effective repeat administration of the first rAAV. According to some embodiments, administering to the subject a rAAV that encodes at least a portion of a capsid of an additional rAAV that encodes a therapeutic transgene, wherein the encoded capsid, or portion thereof, is of the same serotype as the additional rAAV, irrespective of whether or not the rAAV and additional rAAV vectors are the same serotype, induces specific immune tolerance to the rAAV encoding the therapeutic transgene, thereby providing for effective repeat administration of the rAAV encoding the therapeutic transgene.

Described are methods of inducing immune tolerance to a first recombinant adeno-associated virus (rAAV) in a subject comprising: administering to a subject an effective amount of a second rAAV (tolerance inducting rAAV), wherein the second rAAV is optionally of a different serotype than the first rAAV (such as a therapeutic rAAV) and comprises a nucleic acid sequence encoding at least a portion of a capsid protein of the first rAAV, wherein the nucleic acid sequence is operably linked to a promoter; and wherein the second rAAV is capable of infecting a liver cell and expressing the at least a portion of the capsid protein of the first rAAV in the liver thereby inducing immune tolerance to the first rAAV. The promoter can be, but is not limited to a constitutive promoter, an inducible promoter, a liver-specific or hepatocyte-specific promoter, or a synthetic promoter. A liver-specific promoter can be, but is not limited to, an albumin promoter, an alpha-1-antitrypsin promoter, transthyretin (TTR) promoter, and apolipoprotein E (apoE) promoter, a hepatitis B virus core protein promoter, or a promoter comprising the nucleic acid sequence of SEQ ID NO: 3 or a nucleic acid sequence having at least 90% sequence identity to SEQ ID NO: 3. In several embodiments, the use of a liver-specific promoter results in all, or substantially all, of the expression of the protein encoded by the transgene in the liver. In some embodiments, the at least a portion of the capsid protein of the first rAAV comprises an immunogenic fragment of the capsid protein. The capsid protein can be, but is not limited to, a VP1 capsid protein, a VP2 capsid protein, and/or a VP3 capsid protein. Inducing immune tolerance to the first rAAV can comprise one or more of: inducing regulatory T cells (Tregs) specific to the first rAAV, reducing cytotoxic CD8+ T cell response to the first rAAV, reducing the level of pre-existing antibodies to the first rAAV, and reducing production of antibodies against the first rAAV. In some embodiments, the second rAAV is administered systemically. The second rAAV can be administered to a subject that has previously been administered the first rAAV or to a subject that has not been previously administered the first rAAV. The second rAAV can be administered to a subject simultaneously with administering the therapeutic rAAV.

The methods disclosed herein relate to methods of tolerizing a subject to AAV viral antigens thereby allowing for repeat administration of AAV as a therapy. In some embodiments, the methods comprise administering to the subject an effective amount of recombinant adeno-associated virus (rAAV) of one serotype and administering a second AAV comprising a nucleotide sequence encoding at least a portion of a capsid protein of the first AAV (thus matching the serotype of the first serotype) operably linked to a promoter suitable for expression in the liver, wherein the at least a portion of the capsid protein of the first rAAV is immunogenic, and wherein expression of the at least a portion of the capsid protein in the liver induces specific immune tolerance to the first rAAV in the subject. In several embodiments, the serotype of the first and second rAAV are the same. In some embodiments, the serotype of the therapeutic and tolerance-inducing rAAV are different. The promoter can be, but is not limited to constitutive promoter, an inducible promoter, a liver-specific or hepatocyte-specific promoter, or a synthetic promoter. A liver-specific promoter can be, but is not limited to, an albumin promoter, an alpha-1-antitrypsin promoter, a hepatitis B virus core protein promoter, or a promoter comprising the nucleic acid sequence of SEQ ID NO: 3 or a nucleic acid sequence having at least 90%, at least 95%, at least 96%, at least 97%, or at least 98% sequence identity to SEQ ID NO: 3. Optionally, combinations of promoters can be used to drive enhanced expression of the transgene. In some embodiments, administering the second rAAV reduces or eliminates a humoral immune response against a first rAAV or against the capsid protein or the first rAAV. In some embodiments, administration of the second rAAV induces one or more of rAAV-specific regulatory T cells (Tregs), reduced cytotoxic CD8+T cell response to the first rAAV, reduced level of pre-existing antibodies to the first rAAV, and reduction in the production of antibodies against the first rAAV. In some embodiments, the first AAV comprises a therapeutic nucleic acid sequence. The therapeutic nucleic acid sequence can be, but is not limited to, an expressible gene. The expressible gene can encode an RNA or a therapeutic polypeptide.

Described are methods of inducing in a subject an immune response against an antigen. The antigen can be a tumor antigen or an antigen from a pathogen. The methods comprise administering to the subject an effective dose of a first recombinant adeno-associated virus (rAAV) of a first serotype comprising a first nucleotide sequence encoding an antigenic peptide, wherein the first nucleotide sequence is operably linked to a first promoter; and administering an effective dose of a second rAAV having serotype different from the serotype of the first rAAV, wherein the second rAAV comprises a second nucleic acid sequence encoding at least a portion of a capsid protein of the first rAAV, wherein the second nucleic acid sequence is operably linked to a second promoter; and wherein the second rAAV is capable of infecting a liver cell and expressing the at least a portion of the capsid protein of the first rAAV in the liver thereby inducing immune tolerance to the first rAAV in the subject. In some embodiments, the at least a portion of the capsid protein of the first rAAV is immunogenic. The pathogen can be, but is not limited to, a virus, a bacteria, a fungus, or a parasite. The virus can be, but is not limited to, influenza, hepatitis, coronavirus, betacoronavirus, SARS-CoV-2, or a SARS-CoV-2-related coronavirus. The first and second promoters can be, but are not limited to, constitutive promoters, inducible promoters, tissue-specific promoters, and synthetic promoters. In some embodiments, the first promoter is a tissue-specific promoter. In some embodiments, the first promoter is a cell-type specific promoter. In some embodiments, the first promoter is a neuronal cell-specific or muscle-specific promoter. In some embodiments, the second promoter is a liver-specific or hepatocyte-specific promoter. In some embodiments, the at least a portion of the capsid protein of the first rAAV is immunogenic. The capsid protein can be, but is not limited to, a VP1 capsid protein, a VP2 capsid protein, and/or a VP3 capsid protein. The immune response can be, but is not limited to, a cellular immune response to the antigen, a humoral immune response to the antigen, enhancing proliferation of antigen-specific cytotoxic T lymphocytes, eliciting generation of anti-antigen antibodies, reducing the likelihood of infection by pathogen containing the antigen, vaccinating the subject a patient against the pathogen, treating cancer, and combinations thereof. The second rAAV can be administered to the subject prior to, concurrently with, or subsequent to administration of the first rAAV. In some embodiments, the second rAAV is administered by intravenous injection. In some embodiments, one or some subsequent effective doses of the first rAAV are administered to the subject after administration of the first effective dose.

Described are methods for modulating an immune response in a host comprising administering to the host an effective amount of a therapeutic (first) recombinant adeno-associated virus (rAAV) comprising a nucleotide sequence encoding all or a portion of a therapeutic protein; and administering to the host a tolerance-inducing (second) rAAV comprising a nucleotide sequence encoding at least a portion of a capsid protein of the therapeutic rAAV operatively linked to a liver-specific promoter, wherein the at least a portion of the capsid protein of the therapeutic rAAV is immunogenic, and wherein expression of the nucleotide sequence encoding the at least a portion of the capsid protein of the therapeutic rAAV in the liver induces specific immune tolerance to the therapeutic rAAV in a subject.

Described are methods of providing a therapeutic nucleic acid to a subject. The methods comprise administering to the subject an effective dose of a first recombinant adeno-associated virus (rAAV) of a first serotype comprising a first nucleotide sequence encoding at therapeutic nucleic acid, wherein the first nucleotide sequence is operably linked to a first promoter; and administering an effective dose of a second rAAV having serotype different from the serotype of the first rAAV, wherein the second rAAV comprises a second nucleic acid sequence encoding at least a portion of a capsid protein of the first rAAV, wherein the second nucleic acid sequence is operably linked to a second promoter; and wherein the second rAAV is capable of infecting a liver cell and expressing the at least a portion of the capsid protein of the first rAAV in the liver thereby inducing immune tolerance to the first rAAV in the subject. The therapeutic nucleic acid sequence can be, but is not limited to, an expressible gene. The expressible gene can encode an RNA or a therapeutic polypeptide. The first and second promoters can be, but are not limited to, constitutive promoters, inducible promoters, tissue-specific promoters, and synthetic promoters. In some embodiments, the first promoter is a neuronal cell-specific or muscle-specific promoter. In some embodiments, the second promoter is a liver-specific or hepatocyte-specific promoter. In some embodiments, the at least a portion of the capsid protein of the first rAAV is immunogenic. The capsid protein can be, but is not limited to, a VP1 capsid protein, a VP2 capsid protein, and/or a VP3 capsid protein. The second rAAV can be administered to the subject prior to, concurrently with, or subsequent to administration of the first rAAV. In some embodiments, the second rAAV is administered by intravenous injection. In some embodiments, one or some subsequent effective doses of the first rAAV are administered to the subject after administration of the first effective dose.

Described are tolerance-inducing rAAV vectors for inducing immune tolerance to a second rAAV having a difference serotype. The tolerance-inducing rAAV comprises a nucleic acid sequence encoding an immunogenic portion of a capsid protein of the second rAAV having a serotype different from the tolerance-inducing rAAV. The nucleic acid sequence is operably linked to a promoter capable of providing expression of the nucleic acid sequence in a lever cell. The tolerance-inducing rAAV is capable of infecting a liver cell and expressing the immunogenic portion of the capsid protein in the liver thereby inducing immune tolerance to the second rAAV. The promoter can be, but is not limited to constitutive promoter, an inducible promoter, a liver-specific or hepatocyte-specific promoter, or a synthetic promoter. A liver-specific promoter can be, but is not limited to, an albumin promoter, an alpha-1-antitrypsin promoter, a hepatitis B virus core protein promoter, or a promoter comprising the nucleic acid sequence of SEQ ID NO: 3 or a nucleic acid sequence having at least 90%, at least 95%, at least 96%, at least 97%, or at least 98% sequence identity to SEQ ID NO: 3. In some embodiments, the at least a portion of the capsid protein of the second rAAV comprises at least 10% at least 20%, at least 30%, at least 40%, at least 50%, at least 60%, at least 70%, at least 80%, at least 90%, or 100% of the capsid protein. The capsid protein can comprise one or more of: a VP1 capsid protein, a VP2 capsid protein, and/or a VP3 capsid protein. In some embodiment, the capsid protein comprises the VP3 capsid protein. In some embodiments, the immunogenic portion of the capsid protein has at least 90%, at least 95%, at least 96%, at least 97%, or at least 98% identity to the amino acid sequence of SEQ ID NO: 1. In some embodiments, the immunogenic portion of the capsid protein is encoded by a nucleic acid sequence having at least 90%, at least 95%, at least 96%, at least 97%, or at least 98% identity to SEQ ID NO: 2. The tolerance-inducing rAAV can be, but is not limited to, serotype 1, serotype 2, serotype 3, serotype 4, serotype 5, serotype 6, serotype 7, serotype 8, serotype 9, serotype 10, serotype 11, rh10, or rh74. Also described are nucleic acids encoding any of the described tolerance-inducing rAAVs and/or therapeutic rAAVs. In some embodiments, isolated nucleic acid that encode one or more of the tolerance-inducing rAAVs and/or therapeutic rAAVs are provided, including nucleic acids that can be used in the manufacture of the tolerance-inducing rAAVs and/or therapeutic rAAVs. Host cells containing these nucleic acids that can be used in the manufacture of the tolerance-inducing rAAVs and/or therapeutic rAAVs are also provided.

Also described are compositions comprising the tolerance-inducing rAAVs. The compositions comprise a tolerance-inducing rAAV and one or more carriers or excipients. In some embodiments, the compositions further contain a second rAAV, wherein the second rAAV has a serotype difference from the tolerance-inducing rAAV and comprises a therapeutic nucleic acid sequence. The therapeutic nucleic acid sequence can comprise a therapeutic RNA, a therapeutic peptide, or an antigenic polypeptide.

Described are methods for modulating an immune response in a host comprising administering to the host an effective amount of a first recombinant adeno-associated virus (rAAV) of a first serotype comprising a nucleotide sequence encoding all or a portion of a therapeutic protein; and administering a second rAAV of a second serotype comprising a liver-specific promoter and a nucleotide sequence encoding at least a portion of a capsid protein of the first rAAV, wherein the at least a portion of the capsid protein of the first rAAV is immunogenic, and wherein the second rAAV induces specific immune tolerance to the first rAAV in a subject being administered the second rAAV.

These and other features, aspects, and advantages of the present invention will become better understood with reference to the following description and appended claims.

DETAILED DESCRIPTION

Figure 1:
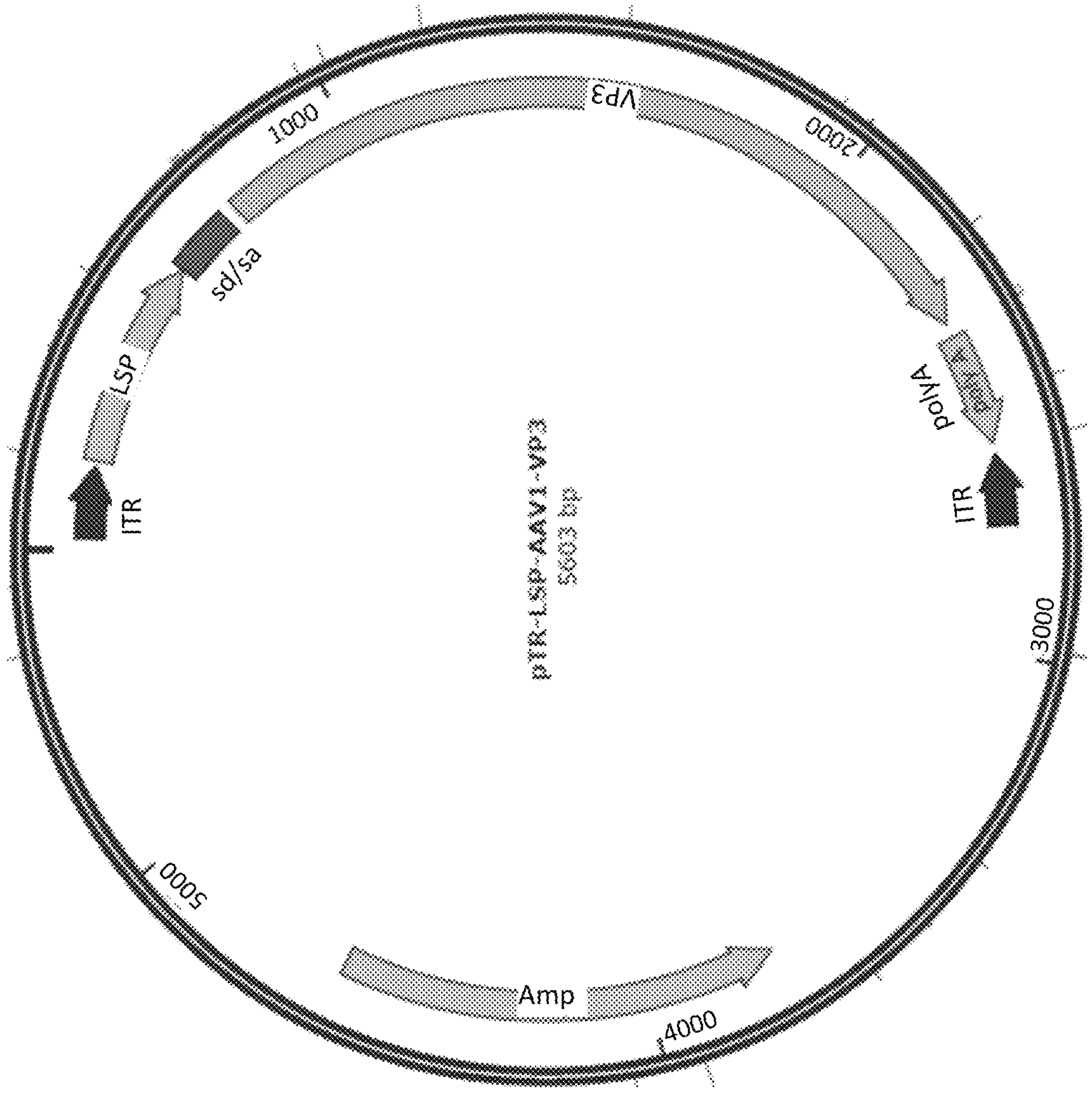
FIG. 1 shows a plasmid map of an exemplary viral construct used to tolerize a subject against a viral capsid protein, for example the VP3 capsid protein of AAV serotype 1, used as part of a therapeutic AAV vector to allow for repeat administration.
Figure 2:
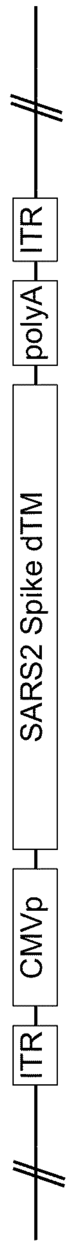
FIG. 2. Schematic of AAV-CMV-SARS2 with AAV2 ITRs and pseudotyped to AAV1.
Figure 3:
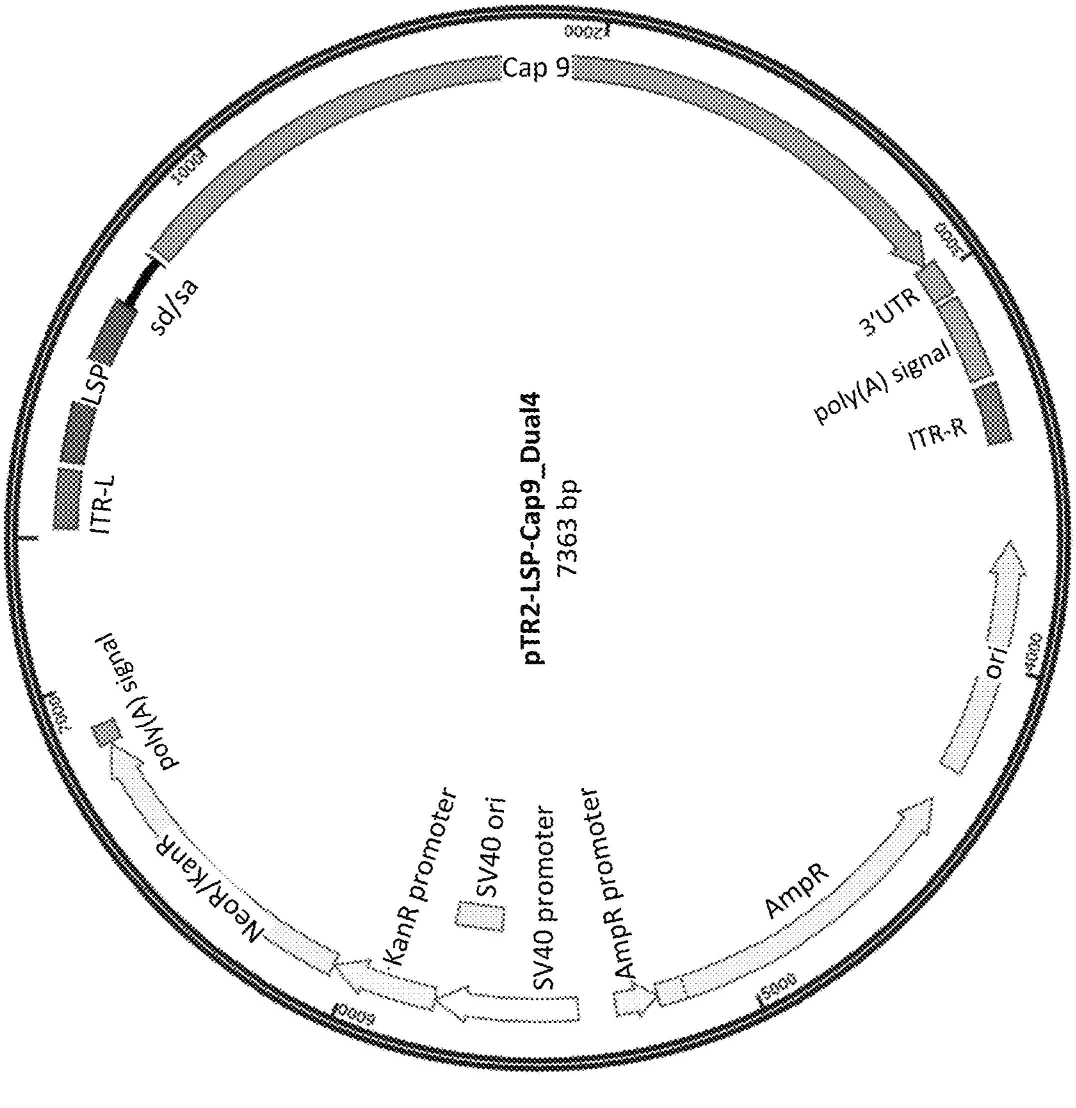
FIG. 3. shows a plasmid map of an exemplary viral construct used to tolerize a subject against a viral capsid protein, for example the VP1 (cap9) capsid protein of AAV (Sequence is provided in SEQ ID NO: 10).

Reference is made to particular features and/or non-limiting embodiments of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

I. Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

A "subject" refers to an animal that is the object of treatment, observation, or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and humans. In some embodiments, the subject is human.

The terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy.

A "vaccine" is a biological substance administered to a patient in order to induce development of acquired immunity to a particular infectious disease. Vaccines often contain an agent that resembles, or is derived from, a disease-causing microorganism and is often made from weakened or killed forms of the microbe, its toxins, or one of its surface proteins. The agent stimulates the body's immune system to recognize the agent as a threat, and to further recognize and destroy any of the microorganisms associated with that agent that it may encounter in the future. Vaccines can be prophylactic (to prevent or ameliorate a future infection) or therapeutic (e.g., vaccines against cancer). Tumor vaccines can be used to induce a subject's immune system to attack tumor or tumor cells.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter).

The term "effective amount," as used herein, refers to an amount that is capable of treating or ameliorating a disease or condition or otherwise capable of producing an intended therapeutic effect.

Sequence identity can be determined by aligning sequences using algorithms, such as BESTFIT, FASTA, and TFASTA in the Wisconsin Genetics Software Package Release 7.0, Genetics Computer Group, 575 Science Dr., Madison, Wis.), using default gap parameters, or by inspection, and the best alignment (i.e., resulting in the highest percentage of sequence similarity over a comparison window). Percentage of sequence identity is calculated by comparing two optimally aligned sequences over a window of comparison, determining the number of positions at which the identical residues occurs in both sequences to yield the number of matched positions, dividing the number of matched positions by the total number of matched and mismatched positions not counting gaps in the window of comparison (i.e., the window size), and multiplying the result by 100 to yield the percentage of sequence identity. Unless otherwise indicated the window of comparison between two sequences is defined by the entire length of the shorter of the two sequences.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition, or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% homologous or identical includes 96%, 97%, 98%, 99%, and 100% homologous or identical to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

The ranges disclosed herein encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% sequence identity or homology includes 96%, 97%, 98%, 99%, and 100% sequence identity or homology to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence. Any titles or subheadings used herein are for organization purposes and should not be used to limit the scope of embodiments disclosed herein.

II. Modulating Immune Response to Gene Therapy Vectors

Described are viral vectors, compositions, kits, and methods or using the vectors, compositions, kits to modulate immune response in a subject. The viral vectors include therapeutic recombinant adeno-associated viruses (rAAVs) and tolerance inducing rAAVs. The therapeutic rAAVs and tolerance inducing AAVs can be used to deliver one or more therapeutic nucleic acids to the subject. The tolerance inducing rAAVs induce immune-specific tolerance to the therapeutic rAAVs to improve efficacy of the therapeutic rAAVs and/or allow for multiple administrations of the therapeutic rAAVs with little or no associated immune response to the therapeutic rAAVs. The therapeutic rAAVs can be used to administer a therapeutic effect to the subject.

A. Wild Type Adeno-Associated Virus

Human adeno-associated virus (AAV) is a non-pathogenic parvovirus that only productively replicates in cells co-infected by a helper virus, usually adenovirus or herpes virus. The virus has a wide host range and can productively infect many cell types from a variety of animal species. Sero-epidemiologic studies have shown that most people (50-96%) in the U.S.A. have been exposed to the most common serotype (AAV2), probably as a passenger during a productive adenovirus (Ad) infection. Nevertheless, AAV has not been implicated in any human or animal disease.

AAV binds to cells via a heparan sulfate proteoglycan receptor. Once attached, AAV entry is dependent upon the presence of a co-receptor, either the fibroblast growth factor receptor or avP5 integrin molecule. In infected cells, the incoming AAV single-stranded DNA (ssDNA) is converted to double-stranded transcriptional template. Cells infected with AAV and a helper virus will undergo productive replication of AAV prior to cell lysis, which is induced by the helper virus rather than AAV. Helper virus encodes proteins or RNA transcripts which are transcriptional regulators and are involved in DNA replication or modify the cellular environment in order to permit efficient viral production. Human cells infected with AAV alone, however, become persistently infected. This latency pathway of wild-type AAV often results in site-specific integration on chromosome 19, the AAVS1 site. The AAV genome consists of two 145-nucleotide inverted terminal repeat (ITR) sequences, each an identical palindrome at either terminus of the virus, flanking the two AAV open reading frames (ORFs), rep and cap. AAV rep and cap genes encode the four Rep proteins (Rep 78, 68, 52 and 40) involved in viral DNA replication, resolution of replicative intermediates and generation of single-strand genomes and the three structural proteins (VP1, VP2, and VP3) that make up the viral capsid. The two larger rep proteins (Rep 78 and Rep 68) are required for resolution of the AAV termini during productive infections. They are also capable of binding to the human chromosome 19 target sequence for AAV integration and initiating site-specific integration. Thus, rep-deleted recombinant AAV vectors do not integrate site-specifically, but rather persist as a combination of episomal forms and random-site integrants.

B. Adeno-Associated Viral Vectors

Recombinant AAV (rAAV) vectors are typically produced by replacing the viral coding sequences with transgenes of interest. These vectors have been shown to be highly efficient for gene transfer and expression at a number of different sites in vitro and in vivo. They have consistently mediated stable expression and have been safe in studies performed in the respiratory tract, the central nervous system, skeletal muscle, liver, and eye. The efficiency of rAAV-mediated transduction has increased as the titer and purity of rAAV preparations has improved. Skeletal muscle is often chosen as the target tissue because it is accessible, efficiently transduced by rAAV vectors, well vascularized, and is able to express and process secreted proteins.

The ITRs from the AAV genome are the only viral sequences required in cis to generate rAAV vectors. Recombinant constructs containing two ITRs bracketing a gene expression cassette of ~5 kb are converted into a ssDNA vector genome and packaged into AAV particles in the presence of AAV rep and cap gene products and helper functions, usually from an Ad. Methods or production and purification of rAAV are known in the art and are suitable for use with the described rAAVs, compositions, and methods (Zolotukhin et al., Gene Ther. 1999 June; 6(6): 973-85; Thorne et al., Hum Gene Ther. 2009 July; 20(7): 707-14; Ayuso et al., Curr Gene Ther. 2010 December; 10(6): 423-36; Cecchini et al., Hum Gene Ther. 2011 August; 22(8): 1021-30; Shin et al., Methods Mol Biol. 2012; 798: 267-84; Chahal et al., J Virol Methods. 2014 February; 196: 163-73; Grieger et al., Mol Ther. 2016 February; 24(2): 287-297; and Clément and Grieger, Mol Ther Methods Clin Dev. 2016 Mar. 16; 3: 16002, each of which is incorporated herein by reference).

Many serotypes of AAV have been cloned and sequenced. Serotypes 1 and 6 share >99% amino acid homology in their capsid proteins. Of the first six AAV serotypes, serotype 2 is best characterized and therefore predominantly used in gene transfer studies, however according to embodiments disclosed herein, other AAV serotypes are also used, such as AAV9, AAV20, rh74, AAV10, and the like. Comparison of the serotype capsid amino acid sequences suggests that types 1, 2 and 3 share homology across the three capsids in accord with heparan sulfate binding. Direct intramuscular injections of non-rAAV2 vectors, especially rAAV1, transduce skeletal muscle more efficiently and secrete canine factor IX at levels two-to-three logs greater than rAAV2. Because the identical transgene cassette was used in the vector constructs, these results suggest that rAAV1 virions are more efficient for gene delivery to muscle. Furthermore, a humoral response was not detected against the transgene protein secreted by intramuscular injection of the rAAV1 construct, contrasting with the significant humoral response elicited by the transgene protein secreted by myocytes transduced by the rAAV2 construct. The lack of cross-reactivity among neutralizing antibodies of different rAAV serotypes suggests that vector repeat administration using different serotypes of rAAV may be feasible for dose titration.

In general, there are two different approaches for packaging rAAV vectors: "true type" and "pseudotyped" vectors. The former refers to vectors having ITRs, Rep proteins and capsid proteins derived from the same wild-type virus, e.g., AAV2. The latter refers to vectors having ITRs and Rep proteins derived from one serotype virus, and capsid proteins from another, e.g., 2 and 1 (AAV2/1).

In recent years, there have been significant improvements in production and purification of rAAV vectors. The major improvements in production have included enhanced output of the number of particles per cell and the emergence of a number of scalable systems. Several groups have independently found that the use of plasmids to express adenovirus (Ad) helper genes in transient transfection results in greater efficiency of rAAV production than infection with Ad virus, perhaps because of enhanced viability of producer cells or the lack of competition with the helper virus for DNA replication machinery. Another interesting finding is that down-regulation of Rep78/68 relative to Rep52/40 and the capsid proteins results in a greater accumulation of single-stranded DNA genomes and packaged vector DNA. The incorporation of these improvements into transient transfection production protocols has enhanced yields from about 1-10 IU per cell to over 100 IU per cell. Stable producer cell lines and packaging cell lines used in combination with recombinant hybrid AAV-adenoviruses have achieved 100-300 IU per cell. Hybrid AAV-herpes vectors have achieved outputs that approach the 5,000-10,000 IU per cell seen with wtAAV. Overall, these newer methods produce greater vector yields and reduce or eliminate detectable replication competent AAV (rcAAV) contamination.

Early reports comparing the transduction efficiencies and specificities of rAAV vector serotypes relied on CsCl gradients for purification, but this approach can generate vector stocks with large particle:infectious (P:I) ratios. Purification using affinity chromatography, based on identified cellular receptors, is becoming more common and the more physiological conditions result in vector stocks with P:I ratios of <50. An efficient and reproducible protocol based on partial purification of an initial freeze and thaw lysate followed by chromatography for the purification and concentration of rAAV1 vectors has been developed for AAV1 clinical manufacturing.

To date, six rAAV vectors have been tested in humans: rAAV-CFTR, rAAV-factor IX, rAAV-sarcoglycan, rAAV-aspartoacylase, rAAV-alpha-1 antitrypsin and rAAV-micro-dystrophin. Extensive work has been done on the rAAV-factor IX vector by a consortium of investigators from the Children's Hospital of Pennsylvania, Stanford University and Avigen. The rAAV-factor IX vector was shown to be capable of long-term correction of the coagulopathy in both the factor IX-deficient mouse and the hemophilia B dog model. Intramuscular administration and portal vein administration were both efficacious in the dog model. Intramuscular administration in the mouse model was associated with the development of a humoral immune response to factor IX, which appears to have been related to the adherence of factor IX to type IV collagen in the extracellular matrix of the muscle. A clinical trial of intramuscular administration was reported, in which some biological activity of the vector was noted at a low dose, without obvious toxicity. The trial for Canavan's disease (aspartoacyclase deficiency) has been completed without adverse events. Currently, the trial of AAV-1 expressing alph-1 antitrypsin has been completed, with no adverse events reported. Additionally, enrollment is completed for ten subjects in Cohorts I-IV of the "Phase I Trial of Ocular Sub-Retinal Injection of a Recombinant Adeno-Associated Virus (rAAV-RPE65) Gene Vector in Patients with Retinal Disease Due to RPE65 Mutations." There are many similarities in the RPE65 study to the study and technology here, where a surgical route of delivery is used to reach the target tissue. There is evidence of safety at two dose levels as well as indication of restoration of retinal function and improved vision in that study.

III. rAAV-Based Compositions and Methods for Modulating Immune Response

Described are non-limiting embodiments of tolerance inducing rAAVS and methods for use in modulating immune response in a subject, such as to an rAAV vector encoding a therapeutic nucleic acid. In some embodiments, modulating immune response comprises inducing immune tolerance to an rAAV vector. In some embodiments, modulating an immune response comprises inducing an immune response against an antigen. Modulating an immune response can be used to prevent or reduce adverse health impacts due to infection or cancer, or to facilitate gene therapy. In several embodiments, the compositions and methods utilize a tolerance inducing rAAV and optionally a therapeutic rAAV. In some embodiments, the compositions and methods utilize a tolerance inducing rAAV and optionally a therapeutic rAAV.

In some embodiments, therapeutic rAAV encodes an antigen and administration of the therapeutic rAAV to the subject that induces an immune response against an antigen. Inducing an immune response can be used to prevent or reduce adverse health impacts due to infection or cancer. In some embodiments, therapeutic rAAV encodes a therapeutic protein or RNA. Expression of the therapeutic protein or RNA can treat a disease or condition or one or more symptoms associated with a disease or condition.

A. Tolerance Inducing rAAV

A tolerance inducing rAAV has a serotype that, in some embodiments, is different from the serotype of a therapeutic rAAV that has been or is expected to be administered to a subject, and comprises a nucleic acid sequence encoding at least an immunogenic portion of a capsid protein of the therapeutic rAAV. The tolerance inducing rAAV is capable of infecting a liver cell and expressing the immunogenic portion of the capsid protein in the liver thereby inducing immune tolerance to the therapeutic rAAV. The nucleic acid sequence encoding the immunogenic portion of a capsid protein is operably linked to a promoter.

The promoter driving expression of the immunogenic portion of a capsid protein can be, but is not limited to, a constitutive promoter, an inducible promoter, a liver-specific promoter, a hepatocyte-specific promoter, or a synthetic promoter. In some embodiments, the promoter is a liver-specific promoter. A constitutive promoter can be, but is not limited to, a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, or a 3-actin promoter. An inducible promoter can be, but is not limited to, a cytochrome P450 gene promoter, a heat shock protein gene promoter, a metallothionein gene promoter, a hormone-inducible gene promoter, an estrogen gene promoter, or a tetVP16 promoter that is responsive to tetracycline. A liver-specific promoter can be, but is not limited to, an albumin promoter, an alpha-1-antitrypsin promoter, or a hepatitis B virus core protein promoter. A synthetic promoter can comprise the nucleic acid sequence of SEQ ID NO: 3, or a nucleic acid sequence having at least 90% sequence identity to SEQ ID NO: 3.

The immunogenic portion of a capsid protein of a tolerance inducing rAAV comprises all or an immunogenic portion of a capsid protein of the therapeutic rAAV. The immunogenic portion of the capsid protein can comprise at least 10% at least 20%, at least 30%, at least 40%, at least 50%, at least 60%, at least 70%, at least 80%, at least 90% of the capsid protein. In some embodiments, the immunogenic portion of the capsid protein comprises an immunogenic portion of one or more of: a VP1 capsid protein, a VP2 capsid protein, and a VP3 capsid protein. In some embodiments, the immunogenic portion of the capsid protein comprises an immunogenic portion of the VP3 capsid protein. In some embodiments, the immunogenic portion of the capsid protein has at least 90% identical, at least 95% identical, or 100% identical to the amino acid sequence of SEQ ID NO: 1. In some embodiments, the immunogenic portion of the capsid protein is encoded by a nucleic acid sequence having at least 90% identify, at least 95% identity, or 100% identity to SEQ ID NO: 2.

The tolerance inducing rAAV can be serotype 1, serotype 2, serotype 3, serotype 4, serotype 5, serotype 6, serotype 7, serotype 8, serotype 9, serotype 10, serotype 11, serotype 12, rh10, or rh74. The tolerance inducing rAAV can also be a pseudo-type rAAV. For a pseudo-type tolerance inducing rAAV, the serotype of the capsid protein is different from the serotype of the capsid protein of the therapeutic rAAV. In some embodiments, the tolerance inducing rAAV is serotype 2, 7, 8, 9, or rh74. In some embodiments, the tolerance inducing rAAV is serotype 2 or 9.

The tolerance inducing rAAV infects a liver cell and results in production of the immunogenic portion of the capsid protein in the liver. The immunogenic portion of the capsid protein may be secreted or it may remain associated with the cell in which it is expressed. The tolerance inducing rAAV induces specific immune tolerance to the therapeutic rAAV in the subject.

IV. Therapeutic rAAV

A therapeutic rAAV comprises a nucleotide sequence encoding a therapeutic gene (e.g., protein or RNA) and is able to transfect (transduce) a cell in the subject, resulting in expression of the therapeutic gene in the cell of the subject. In some embodiments, the therapeutic rAAV preferentially infects neuronal or skeletal muscle cells.

A therapeutic rAAV has a serotype that, in several embodiments, is different from the serotype of a tolerance inducing rAAV that has been or is expected to be administered to a subject and comprises a therapeutic nucleic acid sequence. In some embodiments, the therapeutic rAAV preferentially infects neuronal or skeletal muscle cells.

The therapeutic nucleic acid can encode an expressible gene. The expressible gene can be, but is not limited to, a therapeutic RNA or a therapeutic polypeptide. A therapeutic RNA can be, but is not limited to, a mRNA, an aptamer, a microRNA, an siRNA, an RNA interference polynucleotide, an antisense RNA, a ribozyme, or an RNA from a CRISPR/Cas system (e.g., a Class 1 or Class 2 Cas, such as Cas3, Cas8a, Cas5, Cas8b, Cas8c, Cas10d, Cse1, Cse2, Csy1, Csy2, Csy3, GSU0054, Cas10, Csm2, Cmr5, Cas10, Csx11, Csx10, Csf1, Cas9, Csn2, Cas4, Cpf1, C2c1, C2c3, Cas13a (previously known as C2c2), Cas13b, Cas13c, CasX, or CasY). The therapeutic polypeptide can be but is not limited to, an antigen, an antibody, and immunoglobulin, an antigen-binding molecule, an antigen binding fragment of an antibody, a functional protein that replaces an abnormal or non-functional protein in the subject (or a functional fragment thereof), or an anti-tumor protein such as a tumor suppressor or an immune activating protein. The antigen may be an antigen of a pathogen and a tumor antigen. The pathogen can be, but is not limited to a viral antigen, a bacterial antigen, a parasite antigen, a fungal antigen. The therapeutic polypeptide can be, but is not limited to, human frataxin, myotubularin, a muscle protein, a neuronal protein, acid alfa glucosidase (GAA), and aspartoacylase.

In some embodiments, the therapeutic rAAV has a sequence sharing at least 85% sequence identity to SEQ ID NO: 6 and/or SEQ ID NO: 8. In some embodiments, the therapeutic rAAV has a sequence sharing at least 95% sequence identity to SEQ ID NO: 6 and/or SEQ ID NO: 8. In some embodiments, the viral antigen is at least a portion of a SARS-CoV-2 polypeptide. In some embodiments, the SARS-CoV-2 polypeptide comprises an S1 subunit of the SARS-CoV-2 spike glycoprotein. In some embodiments, the SARS-Cov-2 polypeptide comprises an N-terminal or C-terminal domain of an S1 subunit of the SARS-Cov-2 spike glycoprotein. In some embodiments, the viral protein is derived from the flu virus, HIV, or other virus.

The promoter driving expression of the therapeutic nucleic acid can be, but is not limited to, a constitutive promoter, an inducible promoter, a tissue-specific promoter, a neuronal-specific promoter, a muscle-specific promoter, or a synthetic promoter. In some embodiments, the promoter is a neuronal-specific promoter or a muscle-specific promoter. A constitutive promoter can be, but is not limited to, a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus ElA promoter, a cytomegalovirus (CMV) promoter, a mammalian housekeeping gene promoter, or a 3-actin promoter. An inducible promoter can be, but is not limited to, a cytochrome P450 gene promoter, a heat shock protein gene promoter, a metallothionein gene promoter, a hormone-inducible gene promoter, an estrogen gene promoter, or a tetVP16 promoter that is responsive to tetracycline. A muscle-specific promoter can be, but is not limited to, desmin promoter, a creatine kinase promoter, a myogenin promoter, an alpha myosin heavy chain promoter, or a natriuretic peptide promoter.

In some embodiments, the tolerance inducing rAAV promoter comprises a liver-specific promoter and the therapeutic rAAV promoter comprises a neuronal- or muscle-specific promoter.

The therapeutic rAAV can be serotype 1, serotype 2, serotype 3, serotype 4, serotype 5, serotype 6, serotype 7, serotype 8, serotype 9, serotype 10, serotype 11, serotype 12, rh10, or rh74. The therapeutic rAAV can also be a pseudo-type rAAV. For a pseudo-type therapeutic rAAV, the serotype of the capsid protein is different from the serotype of the capsid protein of the tolerance inducing rAAV. In some embodiments, the therapeutic rAAV is serotype 1.

In some embodiments, therapeutic rAAV is serotype 1 AAV (AAV1) and the tolerance inducing rAAV is serotype 2 AAV (AAV2). In some embodiments, therapeutic rAAV is serotype 1 AAV (AAV1) and the tolerance inducing rAAV is serotype 9 AAV (AAV9). In some embodiments, therapeutic rAAV is serotype 1 AAV (AAV1) and the tolerance inducing rAAV is rh74.

V. Promoter

In some embodiments, the rAAV vector comprises one or more regions comprising a sequence that facilitates expression of the heterologous nucleic acid, e.g., expression control sequences operatively linked to the heterologous nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer).

To achieve appropriate expression levels of the nucleic acid, protein, or polypeptide of interest, any of a number of promoters suitable for use in the selected host cell may be employed. The promoter may be, for example, a constitutive promoter, tissue-specific promoter, inducible promoter, or a synthetic promoter. For example, constitutive promoters of different strengths can be used. An rAAV vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the 3-actin promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting examples of such promoters that may be used include (1) desmin, creatine kinase, myogenin, alpha myosin heavy chain, and natriuretic peptide, specific for muscle cells, and (2) albumin, alpha-1-antitrypsin, hepatitis B virus core protein promoters, specific for liver cells.

Synthetic promoters are also contemplated herein. A synthetic promoter may comprise, for example, regions of known promoters, regulatory elements, transcription factor binding sites, enhancer elements, repressor elements, and the like.

VI. Modulating Immune Response

It is desirable to reduce or eliminate/prevent immune response to a therapeutic rAAV of a given serotype to facilitate expression of a therapeutic nucleic acid delivered by the therapeutic rAAV. In some embodiments, reducing or eliminating/preventing immune response to a therapeutic rAAV vector provides for repeat administration of the therapeutic rAAV. In some embodiments, reducing or eliminating/preventing immune response to a therapeutic rAAV vector comprises reducing antibodies or T cells specific to the therapeutic AAV in the subject, such as $T_{eff}$ cells.

In some embodiments, reducing, eliminating, or preventing an immune response to a therapeutic rAAV vector provides for repeat administration of the therapeutic rAAV. Reducing, eliminating, or preventing an immune response to the therapeutic rAAV vector facilitates administering the therapeutic rAAV to a subject two or more times. Administration of a therapeutic rAAV to a subject two or more times can be done to deliver the same therapeutic nucleic acid two or more times or to deliver different therapeutic nucleic acids using the same serotype rAAV.

The therapeutic rAAV vector can be administered to a subject two or more times to deliver the same therapeutic nucleic acid each time or to deliver different therapeutic nucleic acids. In some embodiments, first (therapeutic) and second (tolerance inducing) rAAV vectors are produced, each encoding a different transgene, which can then be co-administered or sequentially administered to a subject. The tolerance inducing rAAV is configured to express an immunogenic peptide that is derived from the therapeutic rAAV. In some embodiments, the tolerance inducing rAAV vector is configured to express the immunogenic peptide specifically in the liver of the subject, for example through the use of a liver-specific promoter sequence. Liver-specific expression of an immunogenic portion of a capsid protein of the therapeutic rAAV allows the liver of the subject to process that immunogenic portion of the capsid protein, thereby inducing immune tolerance to that protein, thereby reducing or even eliminating an immune response to the therapeutic rAAV vector. As an example, liver-specific expression of an immunogenic portion of the AAV1 VP3 capsid protein allows the liver of the subject to process that protein thereby inducing immune tolerance to the AAV1 VP3 protein, thereby reducing or even eliminating an immune response to an rAAV serotype 1 vector. This tolerance would allow the subject to receive multiple administrations of a rAAV1 vector. For example, multiple administrations may be useful when the rAAV1 vector is re-designed to express a first and then a second transgene, such as antigen variants from a pathogen that has mutated over time.

The tolerance-inducing rAAV and the therapeutic rAAV can be co-administered to a subject or administered sequentially. In some embodiments, the tolerance-inducing rAAV is administered to a subject prior to administering the therapeutic rAAV. In some embodiments, the tolerance-inducing rAAV is administered to a subject concurrently with administering the therapeutic rAAV. In some embodiments, the tolerance-inducing rAAV is administered to a subject after administering the therapeutic rAAV.

In some embodiments, the tolerance-inducing rAAV is administered to a subject prior to administering a first does of the therapeutic rAAV. In some embodiments, the tolerance-inducing rAAV is administered to a subject concurrently with administering a first does of a the therapeutic rAAV. In some embodiments, the tolerance-inducing rAAV is administered to a subject after administering a first does of the therapeutic rAAV.

In some embodiments, the tolerance-inducing rAAV is administered to a subject prior to administering a second or subsequent dose of a therapeutic rAAV. In some embodiments, the tolerance-inducing rAAV is administered to a subject concurrently with administering a second or subsequent dose of a therapeutic rAAV. In some embodiments, the tolerance-inducing rAAV is administered to a subject after administering a second or subsequent dose of a therapeutic rAAV.

In some embodiments, the tolerance-inducing rAAV is administered to a subject after administering a first dose of a therapeutic rAAV and prior to administering a second or subsequent dose of the therapeutic rAAV.

In some embodiments, the liver-specific promoter has at least 90% sequence identity to the sequence of SEQ ID NO: 3. In some embodiments, the liver-specific promoter comprises the sequence of SEQ ID NO: 3. In some embodiments, the immunogenic viral protein is a viral capsid protein. In some embodiments, the immunogenic viral protein comprises an immunogenic portion of one or more of the VP1, VP2, and/or VP3 capsid proteins. In some embodiments, the immunogenic viral protein is derived from the VP3 capsid protein. In some embodiments, the immunogenic viral protein is derived from an AAV serotype 1 VP3 capsid protein. In some embodiments, the immunogenic viral protein has at least 90% sequence identity to SEQ ID NO: 1. In some embodiments, the liver specific promoter drives expression of SEQ ID NO: 1, which is encoded by SEQ ID NO: 2. In some embodiments, the serotype of the rAAV vector that encodes SEQ ID NO: 2 is serotype 2. In some embodiments, the serotype of the rAAV vector that encodes SEQ ID NO: 2 is serotype 9. In some embodiments, the vector construct has at least 90% sequence identity to SEQ ID NO: 4 or 10.

In some embodiments, the first (therapeutic) rAAV induces an immune response against an antigen in a subject and the second (tolerance inducing) rAAV induces specific immune tolerance to the first rAAV in a subject. The immune response can be, but is not limited to, a humoral immune response.

In some embodiments, the therapeutic rAAV induces an immune response against an tumor antigen in a subject and the tolerance-inducing rAAV is used to induce specific immune tolerance to the therapeutic rAAV in the subject. The immune response can be, but is not limited to, a humoral immune response or a cellular immune response.

In some embodiments, the therapeutic rAAV provides a therapeutic gene for treatment of a disease or condition or for treatment of one or more symptoms associated with a disease or condition in a subject and the tolerance-inducing rAAV is used to induce specific immune tolerance to the therapeutic rAAV in a subject.

Described are methods for inducing an immune response in a host comprising administering to the host an effective amount of a first recombinant adeno-associated virus (therapeutic rAAV) of a first serotype comprising a nucleotide sequence encoding an antigen; and administering a second rAAV (tolerance-inducing rAAV) of a second serotype different from the serotype of the first rAAV comprising a liver-specific promoter and a nucleotide sequence encoding at least a portion of a capsid protein of the first rAAV, wherein the at least a portion of the capsid protein of the first rAAV is immunogenic, and wherein the second rAAV induces specific immune tolerance to the first rAAV in a subject being administered the second rAAV.

In some embodiments, the therapeutic rAAV vector is a serotype 1 rAAV and is designed to express a transgene that is an antigenic peptide from a pathogen that could cause an unwanted infection in the subject. The pathogen can be, but is not limited to, an influenza virus or a coronavirus. In some embodiments, the therapeutic rAAV is configured to express the therapeutic transgene in muscle and/or neuronal tissues. Expression of the antigenic peptide in the muscle or neuronal tissue can result in widespread expression of the antigenic peptide and allow the subject's immune system to develop an immune (e.g., antibody) response against the antigenic peptide. Advantageously, the use of the tolerance inducing vector to induce a tolerance to the therapeutic rAAV vector allows repeat administration of the therapeutic rAAV vector. Repeat administration of the therapeutic rAAV enables vaccination against different pathogens, to provide vaccination to pathogen variants, or to provide booster vaccinations to the same pathogen. In some embodiments, the therapeutic rAAV vector drives expression of a SARS-CoV-2 spike protein. In some embodiments, the spike protein has at least 90% sequence identity to SEQ ID NO: 5 and/or SEQ ID NO: 7. In some embodiments, the vector construct has at least 90% sequence identity to SEQ ID NO: 6 and/or SEQ ID NO: 8. In some embodiments, a cytomegalovirus promoter is used to drive the expression of the viral transgene. In some embodiments, the CMV promoter has at least 90% sequence identity to SEQ ID NO: 9.

The methods of the present disclosure can enhance the humoral immune response to a variety of pathogens or antigens thereof. Pathogens include, without limitation, one or more of the following: viruses (including but not limited to coronavirus, human immunodeficiency virus, herpes simplex virus, papilloma virus, parainfluenza virus, influenza virus, hepatitis virus, Coxsackie Virus, herpes zoster virus, measles virus, mumps virus, rubella, rabies virus, hemorrhagic viral fevers, H1N1, and the like), prions, parasites, fungi, mold, yeast and bacteria (both gram-positive and gram-negative). In some embodiments, pathogens include, without limitation, *Candida albicans, Aspergillus niger,*

*Escherichia coli* (*E. coli*), *Pseudomonas aeruginosa* (*P. aeruginosa*), and *Staphylococcus aureus* (*S. aureus*), Group A *streptococci, S. pneumoniae, Mycobacterium tuberculosis, Campylobacter jejuni, Salmonella, Shigella*, and a variety of drug resistant bacteria.

In some embodiments, the pathogen is a virus, e.g., a DNA or RNA virus. In some embodiments, the virus is an RNA virus, e.g., a single or double-stranded virus. In some embodiments, the RNA virus is a positive sense, single-stranded RNA virus. In some embodiments, the virus belongs to the Nidovirales order. In some embodiments, the virus belongs to the Coronaviridae family. In some embodiments, the virus belongs to the alphacoronavirus, betacoronavirus, gammacoronavirus or deltacoronavirus genus. In some embodiments, the alphacoronavirus is, without limitation, human coronavirus 229E, human coronavirus NL63 or transmissible gastroenteritis virus (TGEV). In some embodiments, the betacoronavirus is, without limitation, Severe Acute Respiratory Syndrome Coronavirus (SARS-CoV), SARS-CoV-2 (COVID-19), Middle Eastern Respiratory Syndrome Coronavirus (MERS-CoV), human coronavirus HKU1, or human coronavirus OC43. In some embodiments, the gammacoronavirus is infectious bronchitis virus (IBV).

In some embodiments, the therapeutic rAAV is designed to express a transgene that is a tumor antigen and is administered to a subject to treat cancer. Expression of the tumor antigen can result the subject mounting an immune response to the tumor. The immune response can be a humoral or cellular immune response. The use of the tolerance-inducing rAAV to induce a tolerance to the therapeutic rAAV vector allows repeat administration of the therapeutic rAAV vector. Repeat administration of the therapeutic rAAV enables repeat administration to delivery the same or different tumor antigens.

In some embodiments, the therapeutic rAAV is designed to express a therapeutic protein or mRNA for treating of a disease or condition or to treat one or more symptoms associated with the disease or condition. In some embodiments, the therapeutic rAAV is configured to express the therapeutic nucleic acid in muscle and/or neuronal tissue. Expression of the therapeutic nucleic acid can result amelioration of a disease or condition or one or more symptoms associated with the disease or condition. Expression of the transgene can provide for a functional protein otherwise missing from the subject. The use of the tolerance-inducing rAAV to induce a tolerance to the therapeutic rAAV vector allows repeat administration of the therapeutic rAAV vector. Repeat administration of the therapeutic rAAV enables repeat dosing to continue to provide the therapeutic nucleic acid.

VII. Compositions and Kits

Any of the described therapeutic rAAVs, tolerance inducing rAAVs, or combinations thereof can be provided in a composition or kit. The compositions can contain one or more carriers or excipients and/or one or more additional therapeutic compounds. The compositions or kits can be used to modulate an immune response in a subject or provide a therapeutic nucleic acid to a subject. The compositions or kits can be used to (a) provide a therapeutic nucleic acid to the subject, (b) induce immune tolerance to a therapeutic rAAV in the subject, (c) induce an immune response, such as a humoral response, to an antigen in the subject, or (d) combinations of (a), (b), and/or (c). Inducing an immune response to an antigen in the subject can be used to vaccinate the subject (e.g., immunize the subject against infection). Providing a therapeutic gene to the subject can be used to treat a disease or condition in the subject.

The therapeutic rAAV and tolerance inducing rAAV can be manufacture together or separately. Methods for production of multiple rAAV vectors simultaneously are provided in PCT Patent Application No. PCT/US2015/036841, the entire contents of which is incorporated by reference herein. For separate manufacture of the therapeutic rAAV and tolerance inducing rAAV, the two rAAV vectors can be provided separately or they may be combined. If provided separately, the two rAAV vectors can be co-administered or administered sequentially.

In some embodiments, the compositions or kits are used to induce a humoral immune response against a virus or other pathogen in a subject. In some embodiments, the compositions or kits are used to induce a humoral immune response against a tumor in a subject. In some embodiments, the compositions or kits are used to provide gene therapy to a subject.

In some embodiments, compositions or kits are provided for modulating an immune response in a subject to immunize the subject against a viral infection. The composition or kit comprises: one or more first rAAVs comprising a first heterologous nucleic acid region and a second heterologous nucleic acid region, wherein the first heterologous nucleic acid region encodes at least a portion of a viral antigen, but does not encode a functional virus, and wherein the second heterologous nucleic acid region encodes a promoter to drive expression of the at least a portion of the viral antigen; and a second rAAV comprising a first heterologous nucleic acid region and a second heterologous nucleic acid region, wherein the first heterologous nucleic acid region encodes at least a portion of a capsid protein of the first rAAV, wherein the at least a portion of the capsid protein is immunogenic, and wherein the second heterologous nucleic acid region encodes a promoter that is configured to yield liver-specific expression of the at least a portion of the capsid protein. In several embodiments, the first and second rAAV are the same serotype. In several embodiments, the first and second rAAV are different serotypes.

In some embodiments, compositions or kits are used to vaccinate a subject against infection by a virus. The virus can be, but is not limited to, coronavirus. The coronavirus can be, but is not limited to SARS-Cov-2. For vaccination against SARS-Cov-2, the therapeutic rAAV encodes an immunogenic polypeptide of SARS-Cov-2. The immunogenic polypeptide of SARS-Cov-2 can be, but is not limited to, at least a portion of a SARS-Cov-2 spike glycoprotein. The at least a portion of the SARS-Cov-2 spike glycoprotein can be, but is not limited to, an S1 subunit of the SARS-Cov-2 spike glycoprotein, or an N-terminal or C-terminal domain of an S1 subunit of the SARS-Cov-2 spike glycoprotein.

In some embodiments, compositions or kits for modulating an immune response in a subject to allow repeat administration of a therapeutic rAAV. The compositions or kits comprising a first (therapeutic) rAAV comprising a first heterologous nucleic acid region and a second heterologous nucleic acid region, wherein the first heterologous nucleic acid region encodes all or a portion of a therapeutic nucleic acid, and wherein the second heterologous nucleic acid region encodes a promoter to drive expression of the all or a portion of the therapeutic nucleic acid; and a second rAAV comprising a first heterologous nucleic acid region and a second heterologous nucleic acid region, wherein the first heterologous nucleic acid region encodes at least a portion of a capsid protein of the first rAAV, wherein the at least a portion of the capsid protein is immunogenic, and wherein the second heterologous nucleic acid region encodes a promoter that is configured to yield liver-specific expression of the at least a portion of the capsid protein. In several embodiments, the first and second rAAV are the same serotype. In several embodiments, the first and second rAAV are different serotypes. The therapeutic nucleic acid can encode a therapeutic RNA or a therapeutic polypeptide. A therapeutic RNA can be, but is not limited to, a mRNA, an aptamer, a microRNA, an siRNA, an RNA interference polynucleotide, an antisense RNA, a ribozyme, or an RNA from one or more parts of a CRISPR/Cas complex (e.g., Cas9, CasX, etc.).

In some exemplary the compositions or kits, the compositions or kits comprise a therapeutic rAAV comprising a therapeutic nucleic acid encoding a viral antigen comprising at least a portion of a SARS-Cov-2 polypeptide. In some embodiments, the SARS-Cov-2 polypeptide comprises an S1 subunit of the SARS-Cov-2 spike glycoprotein. In some embodiments, the SARS-Cov-2 polypeptide comprises an N-terminal or C-terminal domain of an S1 subunit of the SARS-Cov-2 spike glycoprotein. In some embodiments, the kits further comprise instructions for use in treating COVID-19.

In some exemplary the compositions or kits, a composition or kit for vaccinating a subject against SARS-CoV-2 comprises: a first (therapeutic) rAAV vector of a first serotype encoding a SARS-CoV-2 soluble spike protein, the expression of which is driven, for example, by a CMV promoter and a second (tolerance inducing) rAAV vector of a second serotype different than the serotype or the first rAAV encoding all or an immunogenic portion of an rAAV capsid protein of the first serotype, the expression of which is driven, for example by a liver-specific promoter. Administration of the second rAAV results in induction of specific immune tolerance to the capsid protein of the first rAAV, thereby reducing or eliminating immune response to the first rAAV vector.

In some embodiments, one or more pharmaceutically acceptable excipients (including vehicles, carriers, diluents, and/or delivery polymers) are added to the pharmaceutical compositions including a therapeutic and/or tolerance inducing rAAVs, thereby forming a pharmaceutical formulation suitable for in vivo delivery to a subject, such as a human.

A pharmaceutical composition or medicament includes a pharmacologically effective amount of at least one of the therapeutic and/or tolerance inducing rAAV and optionally one or more pharmaceutically acceptable excipients. Pharmaceutically acceptable excipients (excipients) are substances other than the Active Pharmaceutical ingredient (API, therapeutic product) that are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

The pharmaceutical compositions can contain other additional components commonly found in pharmaceutical compositions. Such additional components can include, but are not limited to: anti-pruritics, astringents, local anesthetics, or anti-inflammatory agents (e.g., antihistamine, diphenhydramine, etc.).

The carrier can be, but is not limited to, a solvent or dispersion medium containing, for example, water, ethanol, polyol (for example, glycerol, propylene glycol, and liquid polyethylene glycol), and suitable mixtures thereof. A carrier may also contain adjuvants such as preservatives, wetting agents, emulsifying agents, and dispersing agents. A carrier may also contain isotonic agents, such as sugars, polyalcohols, sodium chloride, and the like into the compositions.

Pharmaceutically acceptable refers to those properties and/or substances which are acceptable to the subject from a pharmacological/toxicological point of view. The phrase pharmaceutically acceptable refers to molecular entities, compositions, and properties that are physiologically tolerable and do not typically produce an allergic or other untoward or toxic reaction when administered to a subject. In some embodiments, a pharmaceutically acceptable compound is approved by a regulatory agency of the Federal or a state government or listed in the U.S. Pharmacopeia or other generally recognized pharmacopeia for use in animals and more particularly in humans.

In some embodiments, the kits comprise one or more containers or receptacles comprising one or more doses of any of the described therapeutic and/or tolerance inducing rAAVs. Such kits may be therapeutic in nature. In certain embodiments, the kit contains a unit dosage, meaning a predetermined amount of a composition comprising, for example, a described therapeutic and/or tolerance inducing rAAV with or without one or more additional agents.

One or more of the components of a kit can be provided in one or more liquid or frozen solvents. The solvent can be aqueous or non-aqueous. The formulation in the kit can also be provided as dried powder(s) or in lyophilized form that can be reconstituted upon addition of an appropriate solvent.

In some embodiments, a kit comprises a label, marker, package insert, bar code and/or reader indicating directions of suitable usage of the kit contents. In some embodiments, the kit may comprise a label, marker, package insert, bar code and/or reader indicating that the kit contents may be administered in accordance with a certain dosage or dosing regimen to treat a subject.

VIII. Administration

The first (therapeutic) rAAV and the second (tolerance inducing) rAAV can be co-administered or sequentially administered. For co-administration, the first and second rAAVs can be combined prior to administration. In some embodiments, a tolerance inducing rAAV can be combined with two or more therapeutic rAAVs, wherein the two or more rAAVs encoded different therapeutic nucleic acids.

The rAAVs can be administered by a variety of routes. Administration routes included, but are not limited to, intravenous, intra-arterial, subcutaneous, intramuscular, intrahepatic, intraperitoneal and/or local delivery to a target tissue. In some embodiments, a plurality of injections, or other administration types, are provided, for example 2, 3, 4, 5, 6, 7, 8, 9, 10 or more injections. Depending on the embodiment, the first and second rAAV need not be administered the same number of times (e.g., the first rAAV may be administered 1 time, and the second vector may be administered three times). In some embodiments, the dosing is intramuscular administration.

In some embodiments, the tolerance inducing rAAV is administered by systemic injection. In some embodiments, the tolerance inducing rAAV is administered by intravenous injection.

The dose of a therapeutic rAAV and/or the tolerance inducing rAAV can be between about $1\times10^{10}$ vector genomes (VG) and about $1\times10^{14}$ VG, including about $5\times10^{10}$ VG, $1\times10^{11}$, $5\times10^{11}$, $1\times10^{12}$, $5\times10^{12}$, $1\times10^{13}$, $5\times10^{13}$, $1\times10^{14}$ and any dose in between or inclusive of the doses listed. The dose of the therapeutic rAAV and the dose of the tolerance inducing rAAV can base on relation to one another, or based on the target tissue for expression. For example the ratio of the therapeutic rAAV to the tolerance inducing rAAV can be about 1:1, 1:2, 1:4, 1:5, 1:7, 1:10, 1:20, 1:50, 1:100, 1:200, 1:500, 500:1, 200:1, 100:1, 50:1, 20:1, 10:1, 7:1, 5:1, 4:1, 2:1, or any ratio in between or inclusive of those ratios listed. In some embodiments, depending on the subject to be treated, the dose is on a vector genome/kilogram (VG/kg) body mass basis.

The therapeutic rAAV may be administered on the same day as the tolerance including rAAV, prior to administration of the tolerance inducing rAAV, or after administration of the tolerance inducing rAAV. The tolerance inducing rAAV may be administered on the same day as the therapeutic rAAV, prior to administration of the therapeutic rAAV, or after administration of the therapeutic rAAV. The tolerance including rAAV may be administered 1 day, 2 days, 3 days, 4 days, 5 days, 6 days, 7 days, 8 days, 9 days, 10 days, 11 days, 12 days, 13 days, 14 days, 1 week, 2 weeks, 3 weeks, 4 weeks, 5 weeks, 6 weeks, 7 weeks, 8 weeks, 1 month 2 months, 3 months, 4 months, 5 months, 6 months or more prior to administration of the therapeutic rAAV. The tolerance including rAAV may be administered 1 day, 2 days, 3 days, 4 days, 5 days, 6 days, 7 days, 8 days, 9 days, 10 days, 11 days, 12 days, 13 days, 14 days, 1 week, 2 weeks, 3 weeks, 4 weeks, 5 weeks, 6 weeks, 7 weeks, 8 weeks, 1 month 2 months, 3 months, 4 months, 5 months, 6 months or more after administration of the therapeutic rAAV.

The subject treated by the present methods can be any suitable subject in need of treatment with the therapeutic nucleic acid delivered by a therapeutic rAAV. In some embodiments, the subject is a mammal. In some embodiments, the subject is a human subject. In some embodiments, the subject treated by the present methods can be any suitable subject in need of treatment or prevention of viral infection or other pathogen infection. In some embodiments, the subject may have already been exposed to a given virus, or variant thereof. In some embodiments, the subject has one or more comorbidities, such as, but not limited to a cardiorespiratory dysfunction, hypertension, diabetes, and/or coronary heart disease. "Subject" and "patient" are used interchangeably herein.

In some embodiments, the rAAV particles described herein are administered to otherwise healthy individuals in order to induce development of a humoral immune response against a transgene encoded by the rAAV vector, such as a pathogen antigen (e.g., the SARS-CoV-2 truncated spike protein (such as an engineered protein with at least about 95% sequence identity to SEQ ID NO: 5 and/or SEQ ID NO: 7).

In certain embodiments, treatment of a subject with a rAAV particles as described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy.

IX. Combination Therapies

The rAAV as disclosed can be administered in combination with one or more additional therapeutic agents.

In some embodiments, the additional therapeutic agent comprises an anti-inflammatory agent. The anti-inflammatory agent can be, but is not limited to, a corticosteroid, cortisone hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, methylprednisolone, betamethasone, typically as betamethasone benzoate or betamethasone diproprionate; fluocinonide; prednisone; and triamcinolone, typically as triamcinolone acetonide. In some embodiments, the anti-inflammatory agent is a mast cell degranulation inhibitor, such as, without limitation, cromolyn (5,5'-(2-hydroxypropane-1,3-diyl)bis(oxy)bis(4-oxo-4H-chromene-2-carboxylic acid) (also known as cromoglycate), and 2-carboxylatochromon-5'-yl-2-hydroxypropane derivatives such as bis (acetoxymethyl), disodium cromoglycate, nedocromil (9-ethyl-4,6-dioxo-10-propyl-6,9-dihydro-4H-pyrano[3,2-g]quinoline-2,8-dicarboxylic acid) and tranilast (2-{[(2E)-3-(3,4-dimethoxyphenyl)prop-2-enoyl]amino}), and lodoxamide (2-[2-chloro-5-cyano-3-(oxaloamino)anilino]-2-oxoacetic acid). In some embodiments, the anti-inflammatory agent is a nonsteroidal anti-inflammatory drugs (NSAIDs), such as, without limitation, aspirin compounds (acetylsalicylates), non-aspirin salicylates, diclofenac, diflunisal, etodolac, fenoprofen, flurbiprofen, ibuprofen, indomethacin, ketoprofen, meclofenamate, naproxen, naproxen sodium, phenylbutazone, sulindac, and tometin.

In some embodiments, the anti-inflammatory agent comprises an antihistamine. The antihistamine can be, but is not limited to, clemastine, clemastine fumarate (2(R)-[2-[1-(4-Chlorophenyl)-1-phenyl-ethoxy]ethyl-1-methylpyrrolidine), dexmedetomidine, doxylamine, loratidine, desloratidine and promethazine, and diphenhydramine, or pharmaceutically acceptable salts, solvates or esters thereof. In some embodiments, the antihistamine includes, without limitation, azatadine, azelastine, burfroline, cetirizine, cyproheptadine, doxantrozole, etodroxizine, forskolin, hydroxyzine, ketotifen, oxatomide, pizotifen, proxicromil, N,N'-substituted piperazines or terfenadine. In some embodiments, the antihistamine is an H1 antagonist, such as, but not limited to, cetirizine, chlorpheniramine, dimenhydrinate, diphenhydramine, fexofenadine, hydroxyzine, orphenadrine, pheniramine, and doxylamine. In some embodiments, the antihistamine is an H2 antagonist, such as, but not limited to, cimetidine, famotidine, lafutidine, nizatidine, ranitidine, and roxatidine.

In some embodiments, the additional therapeutic agent comprises an antiviral agent, including antiretroviral agents. Suitable antiviral agents include, without limitation, remdesivir, acyclovir, famcyclovir, ganciclovir, foscarnet, idoxuridine, sorivudine, trifluorothymidine, valacyclovir, vidarabine, didanosine, dideoxyinosine, stavudine, zalcitabine, zidovudine, amantadine, interferon alpha, ribavirin and rimantadine.

In some embodiments, the additional therapeutic agent comprises an antibiotic. Non-limiting examples of suitable antibiotics include beta-lactams such as penicillins, aminopenicillins (e.g., amoxicillin, ampicillin, hetacillin, etc.), penicillinase resistant antibiotics (e.g., cloxacillin, dicloxacillin, methicillin, nafcillin, oxacillin, etc.), extended spectrum antibiotics (e.g., axlocillin, carbenicillin, mezlocillin, piperacillin, ticarcillin, etc.); cephalosporins (e.g., cefadroxil, cefazolin, cephalixin, cephalothin, cephapirin, cephradine, cefaclor, cefacmandole, cefmetazole, cefonicid, ceforanide, cefotetan, cefoxitin, cefprozil, cefuroxime, loracarbef, cefixime, cefoperazone, cefotaxime, cefpodoxime, ceftazidime, ceftiofur, ceftizoxime, ceftriaxone, moxalactam, etc.); monobactams such as aztreonam; Carbapenems such as imipenem and eropenem; quinolones (e.g., ciprofloxacin, enrofloxacin, difloxacin, orbifloxacin, marbofloxacin, etc.); chloramphenicols (e.g., chloramphenicol, thiamphenicol, florfenicol, etc.); tetracyclines (e.g., chlortetracycline, tetracycline, oxytetracycline, doxycycline, minocycline, etc.); macrolides (e.g., erythromycin, tylosin, tlimicosin, clarithromycin, azithromycin, etc.); lincosamides (e.g., lincomycin, clindamycin, etc.); aminoglycosides (e.g., gentamicin, amikacin, kanamycin, apramycin, tobramycin, neomycin, dihydrostreptomycin, paromomycin, etc.); sulfonamides (e.g., sulfadmethoxine, sfulfamethazine, sulfaquinoxaline, sulfamerazine, sulfathiazole, sulfasalazine, sulfadiazine, sulfabromomethazine, suflaethoxypyridazine, etc.); glycopeptides (e.g., vancomycin, teicoplanin, ramoplanin, and decaplanin; and other antibiotics (e.g., rifampin, nitrofuran, virginiamycin, polymyxins, tobramycin, etc.).

In some embodiments, the additional therapeutic agent comprises an antifungal agent, such as, but not limited to, itraconazole, ketoconazole, fluoconazole, and amphotericin B. In some embodiments, the therapeutic agent is an antiparasitic agents, such as, but not limited to, the broad spectrum antiparasitic medicament nitazoxanide; antimalarial drugs and other antiprotozoal agents (e.g., artemisins, mefloquine, lumefantrine, tinidazole, and miltefosine); anthelminthics such as mebendazole, thiabendazole, and ivennectin; and antiamoebic agents such as rifampin and amphotericin B.

In some embodiments, the additional therapeutic agent comprises an analgesic agent, including, without limitation, opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; and nonopioid analgesics such as apazone, etodolac, diphenpyramide, indomethacin, meclofenamate, mefenamic acid, oxaprozin, phenylbutazone, piroxicam, and tolmetin.

SEQUENCES

| SEQ ID NO: | Sequence |
| --- | --- |
| 1 | VP3 Capsid Protein of AAV1<br>MASGGGAPMADNNEGADGVGNASGNWHCDSTWLGDRVITTSTRTWALPTYNNHLYKQISSA<br>STGASNDNHYFGYSTPWGYFDFNRFHCHFSPRDWQRLINNNWGFRPKRLNFKLFNIQVKEVTT<br>NDGVTTIANNLTSTVQVFSDSEYQLPYVLGSAHQGCLPPFPADVFMIPQYGYLTLNNGSQAVGR<br>SSFYCLEYFPSQMLRTGNNFTFSYTFEEVPFHSSYAHSQSLDRLMNPLIDQYLYYLNRTQNQSGS<br>AQNKDLLFSRGSPAGMSVQPKNWLPGPCYRQQRVSKTKTDNNNSNFTWTGASKYNLNGRESII<br>NPGTAMASHKDDEDKFFPMSGVMIFGKESAGASNTALDNVMITDEEEIKATNPVATERFGTVA<br>VNFQSSSTDPATGDVHAMGALPGMVWQDRDVYLQGPIWAKIPHTDGHFHPSPLMGGFGLKNP<br>PPQILIKNTPVPANPPAEFSATKFASFITQYSTGQVSVEIEWELQKENSKRWNPEVQYTSNYAKS<br>ANVDFTVDNNGLYTEPRPIGTRYLTRPL |
| 2 | AAV VP3 Capsid DNA:<br>atggcttcaggcggtggcgcaccaatggcagacaataacgaaggcgccgacggagtgggtaatgcctcaggaaattggcattgcgattccac<br>atggctgggcgacagagtcatcaccaccagcacccgcacctgggccttgcccacctacaataaccacctctacaagcaaatctccagtgctt<br>caacgggggccagcaacgacaaccactacttcggctacagcaccccctgggggtattttgatttcaacagattccactgccacttttcacca<br>cgtgactggcagcgactcatcaacaacaattggggattccggcccaagagactcaacttcaaactcttcaacatccaagtcaaggaggtcac<br>gacgaatgatggcgtcacaaccatcgctaataaccttaccagcacggttcaagtcttctcggactcggagtaccagcttccgtacgtcctcg<br>gctctgcgcaccagggctgcctccctccgttcccggcggacgtgttcatgattccgcaatacggctacctgacgctcaacaatggcagccaa<br>gccgtgggacgttcatcctttttactgcctggaatatttcccttctcagatgctgagaacgggcaacaactttaccttcagctacacctttga<br>ggaagtgcctttccacagcagctacgcgcacagccagagcctggaccggctgatgaatcctctcatcgaccaatacctgtattacctgaaca<br>gaactcaaaatcagtccggaagtgcccaaaacaaggacttgctgtttagccgtgggtctccagctggcatgtctgttcagcccaaaaactgg<br>ctacctggaccctgttatcggcagcagcgcgtttctaaaacaaaaacagacaacaacaacagcaattttacctggactggtgcttcaaaata<br>taacctcaatgggcgtgaatccatcatcaaccctggcactgctatggcctcacacaaagacgacgaagacaagttctttcccatgagcggtg<br>tcatgatttttggaaaagagagcgccggagcttcaaacactgcattggacaatgtcatgattacagacgaagaggaaattaaagccactaac<br>cctgtggccaccgaaagatttgggaccgtggcagtcaatttccagagcagcagcacagaccctgcgaccggagatgtgcatgctatgggagc<br>attacctggcatggtgtggcaagatagagacgtgtacctgcagggtcccatttgggccaaaattcctcacacagatggacactttcacccgt<br>ctcctcttatgggcggctttggactcaagaacccgcctcctcagatcctcatcaaaaacacgcctgttcctgcgaatcctccggcggagttt<br>tcagctacaaagtttgcttcattcatcacccaatactccacaggacaagtgagtgtggaaattgaatgggagctgcagaaagaaaacagcaa<br>gcgctggaatcccgaagtgcagtacacatccaattatgcaaaatctgccaacgttgattttactgtggacaacaatggactttatactgagc<br>ctcgccccattggcacccgttaccttacccgtcccctgtaa |
| 3 | Liver specific GAA promoter<br>ccctaaaatgggcaaacattgcaagcagcaaacagcaaacacacagccctccctgcctgctgaccttggagctggggcagaggtcagagacc<br>tctctggggactgtcccaggtcagtggtggtgcctgaagctgaggagacagggccctgtcctcgtccgtatttaagcagtggatccagaggg |

-continued

SEQUENCES

| SEQ ID NO: | Sequence |
|---|---|
| | gcaacgggggaggctgctggtgaatattaaccaaggtcaccccagttatcggaggagcaaacaggggctaagtccactggctgggatctgag<br>tcgcccgcctacgctgcccggacgctttgcctgggcagtgtacagcttccactgcacttaccgaaaggagtcattgtagggccctgtctcct<br>cagcttcaggcaccaccactgacctgggacagtgaatccgga |
| 4 | pTR-LSP-AAV1-VP3<br>ctgcaggggggggggggggggggttggccactccctctctgcgcgctcgctcgctcactgaggccgggcgaccaaaggtcgcccgacgcccg<br>ggctttgcccgggcggcctcagtgagcgagcgagcgcgcagagagggagtggccaactccatcactaggggttcctagatctccctaaaatg<br>ggcaaacattgcaagcagcaaacagcaaacacacagccctccctgcctgctgaccttggagctggggcagaggtcagagacctctctggga<br>ctgtcccaggtcagtggtggtgcctgaagctgaggagacagggccctgtcctcgtccgtatttaagcagtggatccagaggggcaacggggg<br>aggctgctggtgaatattaaccaaggtcaccccagttatcggaggagcaaacaggggctaagtccactggctgggatctgagtcgcccgcct<br>acgctgcccggacgctttgcctgggcagtgtacagcttccactgcacttaccgaaaggagtcattgtagggccctgtctcctcagcttcagg<br>caccaccactgacctgggacagtgaatccggaaagtatcaaggttacaagacaggtttaaggagaccaatagaaactgggcttgtcgagaca<br>gagaagactcttgcgtttctgataggcacctattggtcttactgacatccactttgcctttctctccacagacgcgtggtaccgtcgacccg<br>ccaccatggcttcaggcggtggcgcaccaatggcagacaataacgaaggcgccgacggagtgggtaatgcctcaggaaattggcattgcgat<br>tccacatggctgggcgacagagtcatcaccaccagcacccgcacctgggccttgcccacctacaataaccacctctacaagcaaatctccag<br>tgcttcaacgggggccagcaacgacaaccactacttcggctacagcaccccctgggggtattttgatttcaacagattccactgccactttt<br>caccacgtgactggcagcgactcatcaacaacaattggggattccggcccaagagactcaacttcaaactcttcaacatccaagtcaaggag<br>gtcacgacgaatgatggcgtcacaaccatcgctaataaccttaccagcacggttcaagtcttctcggactcggagtaccagcttccgtacgt<br>cctcggctctgcgcaccagggctgcctccctccgttcccggcggacgtgttcatgattccgcaatacggctacctgacgctcaacaatggca<br>gccaagccgtgggacgttcatccttttactgcctggaatatttcccttctcagatgctgagaacgggcaacaactttaccttcagctacacc<br>tttgaggaagtgcctttccacagcagctacgcgcacagccagagcctggaccggctgatgaatcctctcatcgaccaatacctgtattacct<br>gaacagaactcaaaatcagtccggaagtgcccaaaacaaggacttgctgtttagccgtgggtctccagctggcatgtctgttcagcccaaaa<br>actggctacctggaccctgttatcggcagcagcgcgtttctaaaacaaaaacagacaacaacaacagcaattttacctggactggtgcttca<br>aaatataacctcaatgggcgtgaatccatcatcaaccctggcactgctatggcctcacacaaagacgacgaagacaagttctttcccatgag<br>cggtgtcatgatttttggaaaagagagcgccggagcttcaaacactgcattggacaatgtcatgattacagacgaagaggaaattaaagcca<br>ctaaccctgtggccaccgaaagatttgggaccgtggcagtcaatttccagagcagcagcacagaccctgcgaccggagatgtgcatgctatg<br>ggagcattacctggcatggtgtggcaagatagagacgtgtacctgcagggtcccatttgggccaaaattcctcacacagatggacactttca<br>cccgtctcctcttatgggcggctttggactcaagaacccgcctcctcagatcctcatcaaaaacacgcctgttcctgcgaatcctccggcgg<br>agttttcagctacaaagtttgcttcattcatcacccaatactccacaggacaagtgagtgtggaaattgaatgggagctgcagaaagaaaac<br>agcaagcgctggaatcccgaagtgcagtacacatccaattatgcaaaatctgccaacgttgattttactgtggacaacaatggactttatac<br>tgagcctcgccccattggcacccgttaccttacccgtcccctgtaatctagagatatcgcggccgcttcgagcagacatgataagatacatt<br>gatgagtttggacaaaccacaactagaatgcagtgaaaaaaatgctttatttgtgaaatttgtgatgctattgctttatttgtaaccattat<br>aagctgcaataaacaagttaacaacaacaattgcattcattttatgtttcaggttcagggggagatgtgggaggttttttaaagcaagtaaa<br>acctctacaaatgtggtaaaatcgataaggatctaggaacccctagtgatggagttggccactccctctctgcgcgctcgctcgctcactga<br>ggccgcccgggcaaagcccgggcgtcgggcgacctttggtcgcccggcctcagtgagcgagcgagcgcgcagagagggagtggccaacccccc<br>cccccccccccctgcagcctggcgtaatagcgaagaggcccgcaccgatcgcccttcccaacagttgcgtagcctgaatggcgaatggcgc<br>gacgcgccctgtagcggcgcattaagcgcggcgggtgtggtggttacgcgcagcgtgaccgctacacttgccagcgccctagcgcccgctcc<br>tttcgctttcttcccttcctttctcgccacgttcgccggctttccccgtcaagctctaaatcgggggctccctttagggttccgatttagtg<br>ctttacggcacctcgaccccaaaaaacttgattagggtgatggttcacgtagtgggccatcgccctgatagacggtttttcgccctttgacg<br>ttggagtccacgttctttaatagtggactcttgttccaaactggaacaacactcaaccctatctcggtctattcttttgatttataagggat<br>tttgccgatttcggcctattggttaaaaaatgagctgatttaacaaaaatttaacgcgaattttaacaaaatattaacgtttacaatttcct<br>gatgcggtattttctccttacgcatctgtgcggtatttcacaccgcatatggtgcactctcagtacaatctgctctgatgccgcatagttaa<br>gccagccccgacacccgccaacacccgctgacgcgccctgacgggcttgtctgctcccggcatccgcttacagacaagctgtgaccgtctcc<br>gggagctgcatgtgtcagaggttttcaccgtcatcaccgaaacgcgcgagacgaaagggcctcgtgatacgcctatttttataggttaatgt<br>catgataataatggtttcttagacgtcaggtggcacttttcggggaaatgtgcgcggaacccctatttgtttatttttctaaatacattcaa<br>atatgtatccgctcatgagacaataaccctgataaatgcttcaataatattgaaaaaggaagagtatgagtattcaacatttccgtgtcgcc<br>cttattcccttttttgcggcattttgccttcctgtttttgctcacccagaaacgctggtgaaagtaaaagatgctgaagatcagttgggtgc<br>acgagtgggttacatcgaactggatctcaacagcggtaagatccttgagagttttcgccccgaagaacgttttccaatgatgagcactttta<br>aagttctgctatgtggcgcggtattatcccgtattgacgccgggcaagagcaactcggtcgccgcatacactattctcagaatgacttggtt<br>gagtactcaccagtcacagaaaagcatcttacggatggcatgacagtaagagaattatgcagtgctgccataaccatgagtgataacactgc<br>ggccaacttacttctgacaacgatcggaggaccgaaggagctaaccgcttttttgcacaacatgggggatcatgtaactcgccttgatcgtt<br>gggaaccggagctgaatgaagccataccaaacgacgagcgtgacaccacgatgcctgtagcaatggcaacaacgttgcgcaaactattaact<br>ggcgaactacttactctagcttcccggcaacaattaatagactggatggaggcggataaagttgcaggaccacttctgcgctcggcccttcc<br>ggctggctggtttattgctgataaatctggagccggtgagcgtgggtctcgcggtatcattgcagcactggggccagatggtaagccctccc<br>gtatcgtagttatctacacgacggggagtcaggcaactatggatgaacgaaatagacagatcgctgagataggtgcctcactgattaagcat<br>tggtaactgtcagaccaagtttactcatatatactttagattgatttaaaacttcatttttaatttaaaaggatctaggtgaagatcctttt<br>tgataatctcatgaccaaaatcccttaacgtgagttttcgttccactgagcgtcagaccccgtagaaaagatcaaaggatcttcttgagatc<br>ctttttttctgcgcgtaatctgctgcttgcaaacaaaaaaaccaccgctaccagcggtggtttgtttgccggatcaagagctaccaactctt<br>tttccgaaggtaactggcttcagcagagcgcagataccaaatactgtccttctagtgtagccgtagttaggccaccacttcaagaactctgt<br>agcaccgcctacatacctcgctctgctaatcctgttaccagtggctgctgccagtggcgataagtcgtgtcttaccgggttggactcaagac<br>gatagttaccggataaggcgcagcggtcgggctgaacggggggttcgtgcacacagcccagcttggagcgaacgacctacaccgaactgaga<br>tacctacagcgtgagcattgagaaagcgccacgcttcccgaagggagaaaggcggacaggtatccggtaagcggcagggtcggaacaggaga<br>gcgcacgagggagcttccagggggaaacgcctggtatctttatagtcctgtcgggtttcgccacctctgacttgagcgtcgatttttgtgat<br>gctcgtcaggggggcggagcctatggaaaaacgccagcaacgcggcctttttacggttcctggccttttgctggccttttgctcacatgttc<br>tttcctgcgttatcccctgattctgtggataaccgtattaccgcctttgagtgagctgataccgctcgccgcagccgaacgaccgagcgcag<br>cgagtcagtgagcgaggaagcggaagagcgcccaatacgcaaaccgcctctccccgcgcgttggccgattcattaatgcaggg |
| 5 | SARS-COV-2 Spike Protein 2P<br>agcttgaattcgccaccatgttcgtgtttctggtgctgctgcctctggtgtccagccagtgtgtgaacctgaccaccagaacacagctgcct<br>ccagcctacaccaacagctttaccagaggcgtgtactaccccgacaaggtgttcagatccagcgtgctgcactctacccaggacctgttcct<br>gcctttcttcagcaacgtgacctggttccacgccatccacgtgtccggcaccaatggcaccaagagattcgacaaccccgtgctgcccttca<br>acgacggggtgtactttgccagcaccgagaagtccaacatcatcagaggctggatcttcggcaccacactggacagcaagacccagagcctg<br>ctgatcgtgaacaacgccaccaacgtggtcatcaaagtgtgcgagttccagttctgcaacgaccccttcctgggcgtctactaccacaagaa |

-continued

SEQUENCES

| SEQ ID NO: | Sequence |
|---|---|
| | caacaagagctggatggaaagcgagttccgggtgtacagcagcgccaacaactgcaccttcgagtacgtgtcccagcctttcctgatggacc<br>tggaaggcaagcagggcaacttcaagaacctgcgcgagttcgtgttcaagaacatcgacggctacttcaagatctacagcaagcacacccct<br>atcaacctcgtgcgggatctgcctcagggcttctctgctctggaacccctggtggatctgcccatcggcatcaacatcacccggtttcagac<br>actgctggccctgcacagaagctacctgacacctggcgatagcagcagcggatggacagctggtgccgccgcttactatgtgggctacctgc<br>agcctagaaccttcctgctgaagtacaacgagaacggcaccatcaccgacgccgtggattgtgctctggatcctctgagcgagacaaagtgc<br>accctgaagtccttcaccgtggaaaagggcatctaccagaccagcaacttccgggtgcagcccaccgaatccatcgtgcggttccccaatat<br>caccaatctgtgccccttcggcgaggtgttcaatgccaccagattcgcctctgtgtacgcctggaaccggaagcggatcagcaattgcgtgg<br>ccgactactccgtgctgtacaactccgccagcttcagcaccttcaagtgctacggcgtgtcccctaccaagctgaacgacctgtgcttcaca<br>aacgtgtacgccgacagcttcgtgatccggggagatgaagtgcggcagattgcccctggacagacaggcaagatcgccgactacaactacaa<br>gctgcccgacgacttcaccggctgtgtgattgcctggaacagcaacaacctggactccaaagtcggcggcaactacaattacctgtaccggc<br>tgttccggaagtccaatctgaagcccttcgagcgggacatctccaccgagatctatcaggccggcagcaccccttgtaacggcgtggaaggc<br>ttcaactgctacttcccactgcagtcctacggctttcagcccacaaatggcgtgggctatcagccctacagagtggtggtgctgagcttcga<br>actgctgcatgcccctgccacagtgtgcggccctaagaaaagcaccaatctcgtgaagaacaaatgcgtgaacttcaacttcaacggcctga<br>ccggcaccggcgtgctgacagagagcaacaagaagttcctgccattccagcagtttggccgggatatcgccgataccacagacgccgttaga<br>gatccccagacactggaaatcctggacatcaccccttgcagcttcggcggagtgtctgtgatcacccctggcaccaacaccagcaatcaggt<br>ggcagtgctgtaccaggacgtgaactgtaccgaagtgcccgtggccattcacgccgatcagctgacacctacatggcgggtgtactccaccg<br>gcagcaatgtgtttcagaccagagccggctgtctgatcggagccgagcacgtgaacaatagctacgagtgcgacatccccatcggcgctggc<br>atctgtgccagctaccagacacagacaaacagccccagacgggccagatctgtggccagccagagcatcattgcctacacaatgtctctggg<br>cgccgagaacagcgtggcctactccaacaactctatcgctatccccaccaacttcaccatcagcgtgaccacagagatcctgcctgtgtcca<br>tgaccaagaccagcgtggactgcaccatgtacatctgcggcgattccaccgagtgctccaacctgctgctgcagtacggcagcttctgcacc<br>cagctgaatagagccctgacagggatcgccgtggaacaggacaagaacacccaagaggtgttcgcccaagtgaagcagatctacaagacccc<br>tcctatcaaggacttcggcggcttcaatttcagccagattctgcccgatcctagcaagcccagcaagcggagcttcatcgaggacctgctgt<br>tcaacaaagtgacactggccgacgccggcttcatcaagcagtatggcgattgtctgggcgacattgccgccagggatctgatttgcgcccag<br>aagtttaacggactgacagtgctgcctcctctgctgaccgatgagatgatcgcccagtacacatctgccctgctggccggcacaatcacaag<br>cggctggacatttggagctggcgccgctctgcagatcccctttgctatgcagatggcctaccggttcaacggcatcggagtgacccagaatg<br>tgctgtacgagaaccagaagctgatcgccaaccagttcaacagcgccatcggcaagatccaggacagcctgagcagcacagcaagcgccctg<br>ggaaagctgcaggacgtggtcaaccagaatgcccaggcactgaacaccctggtcaagcagctgtcctccaacttcggcgccatcagctctgt<br>gctgaacgatatcctgagcagactggaccctcctgaggccgaggtgcagatcgacagactgatcacaggcagactgcagagcctccagacat<br>acgtgacccagcagctgatcagagccgccgagattagagcctctgccaatctggccgccaccaagatgtctgagtgtgtgctgggccagagc<br>aagagagtggacttttgcggcaagggctaccacctgatgagcttccctcagtctgcccctcacggcgtggtgtttctgcacgtgacatatgt<br>gcccgctcaagagaagaatttcaccaccgctccagccatctgccacgacggcaaagcccactttcctagagaaggcgtgttcgtgtccaacg<br>gcacccattggttcgtgacacagcggaacttctacgagccccagatcatcaccaccgacaacaccttcgtgtctggcaactgcgacgtcgtg<br>atcggcattgtgaacaataccgtgtacgaccctctgcagcccgagctggacagcttcaaagaggaactggacaagtactttaagaaccacac<br>aagccccgacgtggacctgggcgatatcagcggaatcaatgccagcgtcgtgaacatccagaaagagatcgaccggctgaacgaggtggcca<br>agaatctgaacgagagcctgatcgacctgcaagaactggggaagtacgagcagtacatcaagtggccctggtacatctggctgggctttatc<br>gccggactgattgccatcgtgatggtcacaatcatgctgtgttgcatgaccagctgctgtagctgcctgaagggctgttgtagctgtggcag<br>ctgctgcaagttcgacgaggacgattctgagcccgtgctgaagggcgtgaaactgcactacacctgagc |
| 6 | pTR-SARS2S-2P<br>gggggggggggggggggttggccactccctctctgcgcgctcgctcgctcactgaggccgggcgaccaaaggtcgcccgacgcccgggcttt<br>gcccgggcggcctcagtgagcgagcgagcgcgcagagagggagtggccaactccatcactaggggttcctagatcttcaatattggccatta<br>gccatattattcattggttatatagcataaatcaatattggctattggccattgcatacgttgtatctatatcataatatgtacatttatat<br>tggctcatgtccaatatgaccgccatgttggcattgattattgactagttattaatagtaatcaattacggggtcattagttcatagcccat<br>atatggagttccgcgttacataacttacggtaaatggcccgcctggctgaccgcccaacgacccccgcccattgacgtcaataatgacgtat<br>gttcccatagtaacgccaatagggactttccattgacgtcaatgggtggagtatttacggtaaactgcccacttggcagtacatcaagtgta<br>tcatatgccaagtccgccccctattgacgtcaatgacggtaaatggcccgcctggcattatgcccagtacatgaccttacgggactttccta<br>cttggcagtacatctacgtattagtcatcgctattaccatggtgatgcggttttggcagtacaccaatgggcgtggatagcggtttgactca<br>cggggatttccaagtctccaccccattgacgtcaatgggagtttgttttggcaccaaaatcaacgggactttccaaaatgtcgtaataaccc<br>cgccccgttgacgcaaatgggcggtaggcgtgtacggtgggaggtctatataagcagagctcgtttagtgaaccgtcagatcactagaagct<br>tgaattcgccaccatgttcgtgtttctggtgctgctgcctctggtgtccagccagtgtgtgaacctgaccaccagaacacagctgcctccag<br>cctacaccaacagctttaccagaggcgtgtactaccccgacaaggtgttcagatccagcgtgctgcactctacccaggacctgttcctgcct<br>ttcttcagcaacgtgacctggttccacgccatccacgtgtccggcaccaatggcaccaagagattcgacaaccccgtgctgcccttcaacga<br>cggggtgtactttgccagcaccgagaagtccaacatcatcagaggctggatcttcggcaccacactggacagcaagacccagagcctgctga<br>tcgtgaacaacgccaccaacgtggtcatcaaagtgtgcgagttccagttctgcaacgaccccttcctgggcgtctactaccacaagaacaac<br>aagagctggatggaaagcgagttccgggtgtacagcagcgccaacaactgcaccttcgagtacgtgtcccagcctttcctgatggacctgga<br>aggcaagcagggcaacttcaagaacctgcgcgagttcgtgttcaagaacatcgacggctacttcaagatctacagcaagcacacccctatca<br>acctcgtgcgggatctgcctcagggcttctctgctctggaacccctggtggatctgcccatcggcatcaacatcacccggtttcagacactg<br>ctggccctgcacagaagctacctgacacctggcgatagcagcagcggatggacagctggtgccgccgcttactatgtgggctacctgcagcc<br>tagaaccttcctgctgaagtacaacgagaacggcaccatcaccgacgccgtggattgtgctctggatcctctgagcgagacaaagtgcaccc<br>tgaagtccttcaccgtggaaaagggcatctaccagaccagcaacttccgggtgcagcccaccgaatccatcgtgcggttccccaatatcacc<br>aatctgtgccccttcggcgaggtgttcaatgccaccagattcgcctctgtgtacgcctggaaccggaagcggatcagcaattgcgtggccga<br>ctactccgtgctgtacaactccgccagcttcagcaccttcaagtgctacggcgtgtcccctaccaagctgaacgacctgtgcttcacaaacg<br>tgtacgccgacagcttcgtgatccggggagatgaagtgcggcagattgcccctggacagacaggcaagategccgactacaactacaagctg<br>cccgacgacttcaccggctgtgtgattgcctggaacagcaacaacctggactccaaagteggcggcaactacaattacctgtaccggctgtt<br>ccggaagtccaatctgaagcccttcgagcgggacatctccaccgagatctatcaggccggcagcaccccttgtaacggcgtggaaggcttca<br>actgctacttcccactgcagtcctacggctttcagcccacaaatggcgtgggctatcagccctacagagtggtggtgctgagcttcgaactg<br>ctgcatgcccctgccacagtgtgcggccctaagaaaagcaccaatctcgtgaagaacaaatgcgtgaacttcaacttcaacggcctgaccgg<br>caccggcgtgctgacagagagcaacaagaagttcctgccattccagcagtttggccgggatatcgccgataccacagacgccgttagagatc<br>cccagacactggaaatcctggacatcaccccttgcagcttcggcggagtgtctgtgatcacccctggcaccaacaccagcaatcaggtggca<br>gtgctgtaccaggacgtgaactgtaccgaagtgcccgtggccattcacgccgatcagctgacacctacatggcgggtgtactccaccggcag<br>caatgtgtttcagaccagagccggctgtctgatcggagccgagcacgtgaacaatagctacgagtgcgacatccccatcggcgctggcatct<br>gtgccagctaccagacacagacaaacagccccagacgggccagatctgtggccagccagagcatcattgcctacacaatgtctctgggcgcc<br>gagaacagegtggcctactccaacaactctatcgctatccccaccaacttcaccatcagcgtgaccacagagatcctgcctgtgtccatgac |

-continued

SEQUENCES

| SEQ ID NO: | Sequence |
|---|---|
| | caagaccagcgtggactgcaccatgtacatctgcggcgattccaccgagtgctccaacctgctgctgcagtacggcagcttctgcacccagc |
| | tgaatagagccctgacagggatcgccgtggaacaggacaagaacacccaagaggtgttcgcccaagtgaagcagattacaagacccctccta |
| | tcaaggacttcggcggcttcaatttcagccagattctgcccgatcctagcaagcccagcaagcggagcttcatcgaggacctgctgttcaac |
| | aaagtgacactggccgacgccggcttcatcaagcagtatggcgattgtctgggcgacattgccgccagggatctgatttgcgcccagaagtt |
| | taacggactgacagtgctgcctcctctgctgaccgatgagatgatcgcccagtacacatctgccctgctggccggcacaatcacaagcggct |
| | ggacatttggagctggcgccgctctgcagatcccctttgctatgcagatggcctaccggttcaacggcatcggagtgacccagaatgtgctg |
| | tacgagaaccagaagctgatcgccaaccagttcaacagcgccatcggcaagatccaggacagcctgagcagcacagcaagcgccctgggaaa |
| | gctgcaggacgtggtcaaccagaatgcccaggcactgaacaccctggtcaagcagctgtcctccaacttcggcgccatcagctctgtgctga |
| | acgatatcctgagcagactggaccctcctgaggccgaggtgcagatcgacagactgatcacaggcagactgcagagcctccagacatacgtg |
| | acccagcagctgatcagagccgccgagattagagcctctgccaatctggccgccaccaagatgtctgagtgtgtgctgggccagagcaagag |
| | agtggacttttgcggcaagggctaccacctgatgagcttccctcagtctgcccctcacggcgtggtgtttctgcacgtgacatatgtgcccg |
| | ctcaagagaagaatttcaccaccgctccagccatctgccacgacggcaaagcccactttcctagagaaggcgtgttcgtgtccaacggcacc |
| | cattggttcgtgacacagcggaacttctacgagccccagatcatcaccaccgacaacaccttcgtgtctggcaactgcgacgtcgtgatcgg |
| | cattgtgaacaataccgtgtacgaccctctgcagcccgagctggacagcttcaaagaggaactggacaagtactttaagaaccacacaagcc |
| | ccgacgtggacctgggcgatatcagcggaatcaatgccagcgtcgtgaacatccagaaagagatcgaccggctgaacgaggtggccaagaat |
| | ctgaacgagagcctgatcgacctgcaagaactggggaagtacgagcagtacatcaagtggccctggtacatctggctgggctttatcgccgg |
| | actgattgccatcgtgatggtcacaatcatgctgtgttgcatgaccagctgctgtagctgcctgaagggctgttgtagctgtggcagctgct |
| | gcaagttcgacgaggacgattctgagcccgtgctgaagggcgtgaaactgcactacacctgagcggccgcttcgagcagacatgataagata |
| | cattgatgagtttggacaaaccacaactagaatgcagtgaaaaaaatgctttatttgtgaaatttgtgatgctattgctttatttgtaacca |
| | ttataagctgcaataaacaagttaacaacaacaattgcattcattttatgtttcaggttcagggggagatgtgggaggttttttaaagcaag |
| | taaaacctctacaaatgtggtaaaatcgataaggatctaggaacccctagtgatggagttggccactccctctctgcgcgctcgctcgctca |
| | ctgaggccgcccgggcaaagcccgggcgtcgggcgacctttggtcgcccggcctcagtgagcgagcgagcgcgcagagagggagtggccaac |
| | ccccccccccccccccctgcagcctggcgtaatagcgaagaggcccgcaccgatcgcccttcccaacagttgcgtagcctgaatggcgaatg |
| | gcgcgacgcgccctgtagcggcgcattaagcgcggcgggtgtggtggttacgcgcagcgtgaccgctacacttgccagcgccctagcgcccg |
| | ctcctttcgctttcttcccttcctttctcgccacgttcgccggctttccccgtcaagctctaaatcgggggctccctttagggttccgattt |
| | agtgctttacggcacctcgaccccaaaaaacttgattagggtgatggttcacgtagtgggccatcgccctgatagacggtttttcgcccttt |
| | gacgttggagtccacgttctttaatagtggactcttgttccaaactggaacaacactcaaccctatctcggtctattcttttgatttataag |
| | ggattttgccgatttcggcctattggttaaaaaatgagctgatttaacaaaaatttaacgcgaattttaacaaaatattaacgtttacaatt |
| | tcctgatgcggtattttctccttacgcatctgtgcggtatttcacaccgcatatggtgcactctcagtacaatctgctctgatgccgcatag |
| | ttaagccagccccgacacccgccaacacccgctgacgcgccctgacgggcttgtctgctcccggcatccgcttacagacaagctgtgaccgt |
| | ctccgggagctgcatgtgtcagaggttttcaccgtcatcaccgaaacgcgcgagacgaaagggcctcgtgatacgcctatttttataggtta |
| | atgtcatgataataatggtttcttagacgtcaggtggcacttttcggggaaatgtgcgcggaacccctatttgtttatttttctaaatacat |
| | tcaaatatgtatccgctcatgagacaataaccctgataaatgcttcaataatattgaaaaaggaagagtatgagtattcaacatttccgtgt |
| | cgcccttattcccttttttgcggcattttgccttcctgtttttgctcacccagaaacgctggtgaaagtaaaagatgctgaagatcagttgg |
| | gtgcacgagtgggttacatcgaactggatctcaacagcggtaagatccttgagagttttcgccccgaagaacgttttccaatgatgagcact |
| | tttaaagttctgctatgtggcgcggtattatcccgtattgacgccgggcaagagcaactcggtcgccgcatacactattctcagaatgactt |
| | ggttgagtactcaccagtcacagaaaagcatcttacggatggcatgacagtaagagaattatgcagtgctgccataaccatgagtgataaca |
| | ctgcggccaacttacttctgacaacgatcggaggaccgaaggagctaaccgcttttttgcacaacatgggggatcatgtaactcgccttgat |
| | cgttgggaaccggagctgaatgaagccataccaaacgacgagcgtgacaccacgatgcctgtagcaatggcaacaacgttgcgcaaactatt |
| | aactggcgaactacttactctagcttcccggcaacaattaatagactggatggaggcggataaagttgcaggaccacttctgcgctcggccc |
| | ttccggctggctggtttattgctgataaatctggagccggtgagcgtgggtctcgcggtatcattgcagcactggggccagatggtaagccc |
| | tcccgtatcgtagttatctacacgacggggagtcaggcaactatggatgaacgaaatagacagatcgctgagataggtgcctcactgattaa |
| | gcattggtaactgtcagaccaagtttactcatatatactttagattgatttaaaacttcatttttaatttaaaaggatctaggtgaagatcc |
| | tttttgataatctcatgaccaaaatcccttaacgtgagttttcgttccactgagcgtcagaccccgtagaaaagatcaaaggatcttcttga |
| | gatcctttttttctgcgcgtaatctgctgcttgcaaacaaaaaaaccaccgctaccagcggtggtttgtttgccggatcaagagctaccaac |
| | tctttttccgaaggtaactggcttcagcagagcgcagataccaaatactgtccttctagtgtagccgtagttaggccaccacttcaagaact |
| | ctgtagcaccgcctacatacctcgctctgctaatcctgttaccagtggctgctgccagtggcgataagtcgtgtcttaccgggttggactca |
| | agacgatagttaccggataaggcgcagcggtcgggctgaacggggggttcgtgcacacagcccagcttggagcgaacgacctacaccgaact |
| | gagatacctacagcgtgagcattgagaaagcgccacgcttcccgaagggagaaaggcggacaggtatccggtaagcggcagggtcggaacag |
| | gagagcgcacgagggagcttccagggggaaacgcctggtatctttatagtcctgtcgggtttcgccacctctgacttgagcgtcgatttttg |
| | tgatgctcgtcaggggggcggagcctatggaaaaacgccagcaacgcggcctttttacggttcctggccttttgctggccttttgctcacat |
| | gttctttcctgcgttatcccctgattctgtggataaccgtattaccgcctttgagtgagctgataccgctcgccgcagccgaacgaccgagc |
| | gcagcgagtcagtgagcgaggaagcggaagagcgcccaatacgcaaaccgcctctccccgcgcgttggccgattcattaatgcagggctgca |
| | g |
| 7 | SARS-COV-2 Spike protein deleted TM domain |
| | agcttgaattcgccaccatgttcgtgtttctggtgctgctgcctctggtgtccagccagtgtgtgaacctgaccaccagaacacagctgcct |
| | ccagcctacaccaacagctttaccagaggcgtgtactaccccgacaaggtgttcagatccagcgtgctgcactctacccaggacctgttcct |
| | gcctttcttcagcaacgtgacctggttccacgccatccacgtgtccggcaccaatggcaccaagagattcgacaaccccgtgctgcccttca |
| | acgacggggtgtactttgccagcaccgagaagtccaacatcatcagaggctggatcttcggcaccacactggacagcaagacccagagcctg |
| | ctgatcgtgaacaacgccaccaacgtggtcatcaaagtgtgcgagttccagttctgcaacgaccccttcctgggcgtctactaccacaagaa |
| | caacaagagctggatggaaagcgagttccgggtgtacagcagcgccaacaactgcaccttcgagtacgtgtcccagcctttcctgatggacc |
| | tggaaggcaagcagggcaacttcaagaacctgcgcgagttcgtgttcaagaacatcgacggctacttcaagatctacagcaagcacacccct |
| | atcaacctcgtgcgggatctgcctcagggcttctctgctctggaacccctggtggatctgcccatcggcatcaacatcacccggtttcagac |
| | actgctggccctgcacagaagctacctgacacctggcgatagcagcagcggatggacagctggtgccgccgcttactatgtgggctacctgc |
| | agcctagaaccttcctgctgaagtacaacgagaacggcaccatcaccgacgccgtggattgtgctctggatcctctgagcgagacaaagtgc |
| | accctgaagtccttcaccgtggaaaagggcatctaccagaccagcaacttccgggtgcagcccaccgaatccatcgtgcggttccccaatat |
| | caccaatctgtgccccttcggcgaggtgttcaatgccaccagattcgcctctgtgtacgcctggaaccggaagcggatcagcaattgcgtgg |
| | ccgactactccgtgctgtacaactccgccagcttcagcaccttcaagtgctacggcgtgtcccctaccaagctgaacgacctgtgcttcaca |
| | aacgtgtacgccgacagcttcgtgatccggggagatgaagtgcggcagattgcccctggacagacaggcaagatcgccgactacaactacaa |
| | gctgcccgacgacttcaccggctgtgtgattgcctggaacagcaacaacctggactccaaagtcggcggcaactacaattacctgtaccggc |
| | tgttccggaagtccaatctgaagcccttcgagcgggacatctccaccgagatctatcaggccggcagcaccccttgtaacggcgtggaaggc |
| | ttcaactgctacttcccactgcagtcctacggctttcagcccacaaatggcgtgggctatcagccctacagagtggtggtgctgagcttcga |

-continued

SEQUENCES

| SEQ ID NO: | Sequence |
|---|---|
| | actgctgcatgcccctgccacagtgtgcggccctaagaaaagcaccaatctcgtgaagaacaaatgcgtgaacttcaacttcaacggcctga<br>ccggcaccggcgtgctgacagagagcaacaagaagttcctgccattccagcagtttggccgggatatcgccgataccacagacgccgttaga<br>gatccccagacactggaaatcctggacatcaccccttgcagcttcggcggagtgtctgtgatcacccctggcaccaacaccagcaatcaggt<br>ggcagtgctgtaccaggacgtgaactgtaccgaagtgcccgtggccattcacgccgatcagctgacacctacatggcgggtgtactccaccg<br>gcagcaatgtgtttcagaccagagccggctgtctgatcggagccgagcacgtgaacaatagctacgagtgcgacatccccatcggcgctggc<br>atctgtgccagctaccagacacagacaaacagccccagacgggccagatctgtggccagccagagcatcattgcctacacaatgtctctggg<br>cgccgagaacagcgtggcctactccaacaactctatcgctatccccaccaacttcaccatcagcgtgaccacagagatcctgcctgtgtcca<br>tgaccaagaccagcgtggactgcaccatgtacatctgcggcgattccaccgagtgctccaacctgctgctgcagtacggcagcttctgcacc<br>cagctgaatagagccctgacagggatcgccgtggaacaggacaagaacacccaagaggtgttcgcccaagtgaagcagatctacaagacccc<br>tcctatcaaggacttcggcggcttcaatttcagccagattctgcccgatcctagcaagcccagcaagcggagcttcatcgaggacctgctgt<br>tcaacaaagtgacactggccgacgccggcttcatcaagcagtatggcgattgtctgggcgacattgccgccagggatctgatttgcgcccag<br>aagtttaacggactgacagtgctgcctcctctgctgaccgatgagatgatcgcccagtacacatctgccctgctggccggcacaatcacaag<br>cggctggacatttggagctggcgccgctctgcagatcccctttgctatgcagatggcctaccggttcaacggcatcggagtgacccagaatg<br>tgctgtacgagaaccagaagctgatcgccaaccagttcaacagcgccatcggcaagatccaggacagcctgagcagcacagcaagcgccctg<br>ggaaagctgcaggacgtggtcaaccagaatgcccaggcactgaacaccctggtcaagcagctgtcctccaacttcggcgccatcagctctgt<br>gctgaacgatatcctgagcagactggaccctcctgaggccgaggtgcagatcgacagactgatcacaggcagactgcagagcctccagacat<br>acgtgacccagcagctgatcagagccgccgagattagagcctctgccaatctggccgccaccaagatgtctgagtgtgtgctgggccagagc<br>aagagagtggacttttgcggcaagggctaccacctgatgagcttccctcagtctgcccctcacggcgtggtgtttctgcacgtgacatatgt<br>gcccgctcaagagaagaatttcaccaccgctccagccatctgccacgacggcaaagcccactttcctagagaaggcgtgttcgtgtccaacg<br>gcacccattggttcgtgacacagcggaacttctacgagccccagatcatcaccaccgacaacaccttcgtgtctggcaactgcgacgtcgtg<br>atcggcattgtgaacaataccgtgtacgaccctctgcagcccgagctggacagcttcaaagaggaactggacaagtactttaagaaccacac<br>aagccccgacgtggacctgggcgatatcagcggaatcaatgccagcgtcgtgaacatccagaaagagatcgaccggctgaacgaggtggcca<br>agaatctgaacgagagcctgatcgacctgcaagaactggggaagtacgagggctacatccctgaggctcctagagatggccaggcctacgtc<br>agaaaggatggcgagtgggtcctgctgagcaccttcctgtaatctagagc |
| 8 | p-TR-SARS2-2P-dTM<br>gggggggggggggggggttggccactccctctctgcgcgctcgctcgctcactgaggccgggcgaccaaaggtcgcccgacgcccgggcttt<br>gcccgggcggcctcagtgagcgagcgagcgcgcagagagggagtggccaactccatcactaggggttcctagatcttcaatattggccatta<br>gccatattattcattggttatatagcataaatcaatattggctattggccattgcatacgttgtatctatatcataatatgtacatttatat<br>tggctcatgtccaatatgaccgccatgttggcattgattattgactagttattaatagtaatcaattacggggtcattagttcatagcccat<br>atatggagttccgcgttacataacttacggtaaatggcccgcctggctgaccgcccaacgacccccgcccattgacgtcaataatgacgtat<br>gttcccatagtaacgccaatagggactttccattgacgtcaatgggtggagtatttacggtaaactgcccacttggcagtacatcaagtgta<br>tcatatgccaagtccgcccccctattgacgtcaatgacggtaaatggcccgcctggcattatgcccagtacatgaccttacgggactttccta<br>cttggcagtacatctacgtattagtcatcgctattaccatggtgatgcggttttggcagtacaccaatgggcgtggatagcggtttgactca<br>cggggatttccaagtctccaccccattgacgtcaatgggagtttgttttggcaccaaaatcaacgggactttccaaaatgtcgtaataaccc<br>cgccccgttgacgcaaatgggcggtaggcgtgtacggtgggaggtctatataagcagagctcgtttagtgaaccgtcagatcactagaagct<br>tgaattcgccaccatgttcgtgtttctggtgctgctgcctctggtgtccagccagtgtgtgaacctgaccaccagaacacagctgcctccag<br>cctacaccaacagctttaccagaggcgtgtactaccccgacaaggtgttcagatccagcgtgctgcactctacccaggacctgttcctgcct<br>ttcttcagcaacgtgacctggttccacgccatccacgtgtccggcaccaatggcaccaagagattcgacaaccccgtgctgcccttcaacga<br>cggggtgtactttgccagcaccgagaagtccaacatcatcagaggctggatcttcggcaccacactggacagcaagacccagagcctgctga<br>tcgtgaacaacgccaccaacgtggtcatcaaagtgtgcgagttccagttctgcaacgaccccttcctgggcgtctactaccacaagaacaac<br>aagagctggatggaaagcgagttccgggtgtacagcagcgccaacaactgcaccttcgagtacgtgtcccagcctttcctgatggacctgga<br>aggcaagcagggcaacttcaagaacctgcgcgagttcgtgttcaagaacatcgacggctacttcaagatctacagcaagcacacccctatca<br>acctcgtgcgggatctgcctcagggcttctctgctctggaaccccctggtggatctgcccatcggcatcaacatcacccggtttcagacactg<br>ctggccctgcacagaagctacctgacacctggcgatagcagcagcggatggacagctggtgccgccgcttactatgtgggctacctgcagcc<br>tagaaccttcctgctgaagtacaacgagaacggcaccatcaccgacgccgtggattgtgctctggatcctctgagcgagacaaagtgcaccc<br>tgaagtccttcaccgtggaaaagggcatctaccagaccagcaacttccgggtgcagcccaccgaatccatcgtgcggttccccaatatcacc<br>aatctgtgccccttcggcgaggtgttcaatgccaccagattcgcctctgtgtacgcctggaaccggaagcggatcagcaattgcgtggccga<br>ctactccgtgctgtacaactccgccagcttcagcaccttcaagtgctacggcgtgtcccctaccaagctgaacgacctgtgcttcacaaacg<br>tgtacgccgacagcttcgtgatccggggagatgaagtgcggcagattgcccctggacagacaggcaagatcgccgactacaactacaagctg<br>cccgacgacttcaccggctgtgtgattgcctggaacagcaacaacctggactccaaagtcggcggcaactacaattacctgtaccggctgtt<br>ccggaagtccaatctgaagcccttcgagcgggacatctccaccgagatctatcaggccggcagcaccccttgtaacggcgtggaaggcttca<br>actgctacttcccactgcagtcctacggctttcagcccacaaatggcgtgggctatcagccctacagagtggtggtgctgagcttcgaactg<br>ctgcatgc+51ccctgccacagtgtgcggccctaagaaaagcaccaatctcgtgaagaacaaatgcgtgaacttcaacttcaacggcctgac<br>cggcaccggcgtgctgacagagagcaacaagaagttcctgccattccagcagtttggccgggatatcgccgataccacagacgccgttagag<br>atccccagacactggaaatcctggacatcaccccttgcagcttcggcggagtgtctgtgatcacccctggcaccaacaccagcaatcaggtg<br>gcagtgctgtaccaggacgtgaactgtaccgaagtgcccgtggccattcacgccgatcagctgacacctacatggcgggtgtactccaccgg<br>cagcaatgtgtttcagaccagagccggctgtctgatcggagccgagcacgtgaacaatagctacgagtgcgacatccccatcggcgctggca<br>tctgtgccagctaccagacacagacaaacagccccagacgggccagatctgtggccagccagagcatcattgcctacacaatgtctctgggc<br>gccgagaacagcgtggcctactccaacaactctatcgctatccccaccaacttcaccatcagcgtgaccacagagatcctgcctgtgtccat<br>gaccaagaccagcgtggactgcaccatgtacatctgcggcgattccaccgagtgctccaacctgctgctgcagtacggcagcttctgcaccc<br>agctgaatagagccctgacagggatcgccgtggaacaggacaagaacacccaagaggtgttcgcccaagtgaagcagatctacaagacccct<br>cctatcaaggacttcggcggcttcaatttcagccagattctgcccgatcctagcaagcccagcaagcggagcttcatcgaggacctgctgtt<br>caacaaagtgacactggccgacgccggcttcatcaagcagtatggcgattgtctgggcgacattgccgccagggatctgatttgcgcccaga<br>agtttaacggactgacagtgctgcctcctctgctgaccgatgagatgatcgcccagtacacatctgccctgctggccggcacaatcacaagc<br>ggctggacatttggagctggcgccgctctgcagatcccctttgctatgcagatggcctaccggttcaacggcatcggagtgacccagaatgt<br>gctgtacgagaaccagaagctgatcgccaaccagttcaacagcgccatcggcaagatccaggacagcctgagcagcacagcaagcgccctgg<br>gaaagctgcaggacgtggtcaaccagaatgcccaggcactgaacaccctggtcaagcagctgtcctccaacttcggcgccatcagctctgtg<br>ctgaacgatatcctgagcagactggaccctcctgaggccgaggtgcagatcgacagactgatcacaggcagactgcagagcctccagacata<br>cgtgacccagcagctgatcagagccgccgagattagagcctctgccaatctggccgccaccaagatgtctgagtgtgtgctgggccagagca<br>agagagtggacttttgcggcaagggctaccacctgatgagcttccctcagtctgcccctcacggcgtggtgtttctgcacgtgacatatgtg<br>cccgctcaagagaagaatttcaccaccgctccagccatctgccacgacggcaaagcccactttcctagagaaggcgtgttcgtgtccaacgg<br>cacccattggttcgtgacacagcggaacttctacgagccccagatcatcaccaccgacaacaccttcgtgtctggcaactgcgacgtcgtga |

-continued

SEQUENCES

| SEQ ID NO: | Sequence |
|---|---|
| | tcggcattgtgaacaataccgtgtacgaccctctgcagcccgagctggacagcttcaaagaggaactggacaagtactttaagaaccacaca<br>agccccgacgtggacctgggcgatatcagcggaatcaatgccagcgtcgtgaacatccagaaagagatcgaccggctgaacgaggtggccaa<br>gaatctgaacgagagcctgatcgacctgcaagaactggggaagtacgagggctacatccctgaggctcctagagatggccaggcctacgtca<br>gaaaggatggcgagtgggtcctgctgagcaccttcctgtaatctagagcggccgcttcgagcagacatgataagatacattgatgagtttgg<br>acaaaccacaactagaatgcagtgaaaaaaatgctttatttgtgaaatttgtgatgctattgctttatttgtaaccattataagctgcaata<br>aacaagttaacaacaacaattgcattcattttatgtttcaggttcagggggagatgtgggaggttttttaaagcaagtaaaacctctacaaa<br>tgtggtaaaatcgataaggatctaggaacccctagtgatggagttggccactccctctctgcgcgctcgctcgctcactgaggccgcccggg<br>caaagcccgggcgtcgggcgacctttggtcgcccggcctcagtgagcgagcgagcgcgcagagagggagtggccaacccccccccccccccc<br>cctgcagcctggcgtaatagcgaagaggcccgcaccgatcgcccttcccaacagttgcgtagcctgaatggcgaatggcgcgacgcgccctg<br>tagcggcgcattaagcgcggcgggtgtggtggttacgcgcagcgtgaccgctacacttgccagcgccctagcgcccgctcctttcgctttct<br>tcccttcctttctcgccacgttcgccggctttccccgtcaagctctaaatcgggggctccctttagggttccgatttagtgctttacggcac<br>ctcgaccccaaaaaacttgattagggtgatggttcacgtagtgggccatcgccctgatagacggtttttcgccctttgacgttggagtccac<br>gttctttaatagtggactcttgttccaaactggaacaacactcaaccctatctcggtctattcttttgatttataagggattttgccgattt<br>cggcctattggttaaaaaatgagctgatttaacaaaaatttaacgcgaattttaacaaaatattaacgtttacaatttcctgatgcggtatt<br>ttctccttacgcatctgtgcggtatttcacaccgcatatggtgcactctcagtacaatctgctctgatgccgcatagttaagccagccccga<br>cacccgccaacacccgctgacgcgccctgacgggcttgtctgctcccggcatccgcttacagacaagctgtgaccgtctccgggagctgcat<br>gtgtcagaggttttcaccgtcatcaccgaaacgcgcgagacgaaagggcctcgtgatacgcctatttttataggttaatgtcatgataataa<br>tggtttcttagacgtcaggtggcacttttcggggaaatgtgcgcggaacccctatttgtttatttttctaaatacattcaaatatgtatccg<br>ctcatgagacaataaccctgataaatgcttcaataatattgaaaaaggaagagtatgagtattcaacatttccgtgtcgcccttattccctt<br>ttttgcggcattttgccttcctgtttttgctcacccagaaacgctggtgaaagtaaaagatgctgaagatcagttgggtgcacgagtgggtt<br>acatcgaactggatctcaacagcggtaagatccttgagagttttcgccccgaagaacgttttccaatgatgagcacttttaaagttctgcta<br>tgtggcgcggtattatcccgtattgacgccgggcaagagcaactcggtcgccgcatacactattctcagaatgacttggttgagtactcacc<br>agtcacagaaaagcatcttacggatggcatgacagtaagagaattatgcagtgctgccataaccatgagtgataacactgcggccaacttac<br>ttctgacaacgatcggaggaccgaaggagctaaccgcttttttgcacaacatgggggatcatgtaactcgccttgatcgttgggaaccggag<br>ctgaatgaagccataccaaacgacgagcgtgacaccacgatgcctgtagcaatggcaacaacgttgcgcaaactattaactggcgaactact<br>tactctagcttcccggcaacaattaatagactggatggaggcggataaagttgcaggaccacttctgcgctcggcccttccggctggctggt<br>ttattgctgataaatctggagccggtgagcgtgggtctcgcggtatcattgcagcactggggccagatggtaagccctcccgtatcgtagtt<br>atctacacgacggggagtcaggcaactatggatgaacgaaatagacagatcgctgagataggtgcctcactgattaagcattggtaactgtc<br>agaccaagtttactcatatatactttagattgatttaaaacttcatttttaatttaaaaggatctaggtgaagatcctttttgataatctca<br>tgaccaaaatcccttaacgtgagttttcgttccactgagcgtcagaccccgtagaaaagatcaaaggatcttcttgagatcctttttttctg<br>cgcgtaatctgctgcttgcaaacaaaaaaaccaccgctaccagcggtggtttgtttgccggatcaagagctaccaactctttttccgaaggt<br>aactggcttcagcagagcgcagataccaaatactgtccttctagtgtagccgtagttaggccaccacttcaagaactctgtagcaccgccta<br>catacctcgctctgctaatcctgttaccagtggctgctgccagtggcgataagtcgtgtcttaccgggttggactcaagacgatagttaccg<br>gataaggcgcagcggtcgggctgaacggggggttcgtgcacacagcccagcttggagcgaacgacctacaccgaactgagatacctacagcg<br>tgagcattgagaaagcgccacgcttcccgaagggagaaaggcggacaggtatccggtaagcggcagggtcggaacaggagagcgcacgaggg<br>agcttccagggggaaacgcctggtatctttatagtcctgtcgggtttcgccacctctgacttgagcgtcgatttttgtgatgctcgtcaggg<br>gggcggagcctatggaaaaacgccagcaacgcggcctttttacggttcctggccttttgctggccttttgctcacatgttctttcctgcgtt<br>atcccctgattctgtggataaccgtattaccgcctttgagtgagctgataccgctcgccgcagccgaacgaccgagcgcagcgagtcagtga<br>gcgaggaagcggaagagcgcccaatacgcaaaccgcctctccccgcgcgttggccgattcattaatgcagggctgcag |
| 9 | CMV promoter<br>tcaatattggccattagccatattattcattggttatatagcataaatcaatattggctattggccattgcatacgttgtatctatatcata<br>atatgtacatttatattggctcatgtccaatatgaccgccatgttggcattgattattgactagttattaatagtaatcaattacggggtca<br>ttagttcatagcccatatatggagttccgcgttacataacttacggtaaatggcccgcctggctgaccgcccaacgacccccgcccattgac<br>gtcaataatgacgtatgttcccatagtaacgccaatagggactttccattgacgtcaatgggtggagtatttacggtaaactgcccacttgg<br>cagtacatcaagtgtatcatatgccaagtccgcccccctattgacgtcaatgacggtaaatggcccgcctggcattatgcccagtacatgacc<br>ttacgggactttcctacttggcagtacatctacgtattagtcatcgctattaccatggtgatgcggttttggcagtacaccaatgggcgtgg<br>atagcggtttgactcacggggatttccaagtctccaccccattgacgtcaatgggagtttgttttggcaccaaaatcaacgggactttccaa<br>aatgtcgtaataaccccgccccgttgacgcaaatgggcggtaggcgtgtacggtgggaggtctatataagcagagctcgtttagtgaaccgt<br>cagatcactaga |
| 10 | pTR2-LSP-Cap9_Dual4<br>ttaattaactgcagacgccagctgttggccactccctctctgcgcgctcgctcgctcactgaggccgggcgaccaaaggtcgcccgacgccc<br>gggctttgcccgggggcctcagtgagcgagcgagcgcgcagagagggagtggccaactccatcactaggggttccttctagaggcgcgccaa<br>gcttccctaaaatgggcaaacattgcaagcagcaaacagcaaacacacagccctccctgcctgctgaccttggagctggggcagaggtcaga<br>gacctctctggggactgtcccaggtcagtggtggtgcctgaagctgaggagacagggccctgtcctcgtccgtatttaagcagtggatccag<br>aggggcaacgggggaggctgctggtgaatattaaccaaggtcaccccagttatcggaggagcaaacaggggctaagtccactggctgggatc<br>tgagtcgcccgcctacgctgcccggacgctttgcctgggcagtgtacagcttccactgcacttaccgaaaggagtcattgtagggccctgtc<br>tcctcagcttcaggcaccaccactgacctgggacagtgaatccggaactagtaagtatcaaggttacaagacaggtttaaggagaccaatag<br>aaactgggcttgtcgagacagagaagactcttgcgtttctgataggcacctattggtcttactgacatccactttgcctttctctccacagg<br>ctagcatttaaatcaggtatggctgccgatggttatcttccagattggctcgaggacaaccttagtgaaggaattcgcgagtggtgggcttt<br>gaaacctggagcccctcaacccaaggcaaatcaacaacatcaagacaacgctcgaggtcttgtgcttccgggttacaaataccttggacccg<br>gcaacggactcgacaagggggagccggtcaacgcagcagacgcggcggccctcgagcacgacaaggcctacgaccagcagctcaaggccgga<br>gacaacccgtacctcaagtacaaccacgccgacgccgagttccaggagcggctcaaagaagatacgtcttttgggggcaacctcgggcgagc<br>agtcttccaggccaaaaagaggcttcttgaacctcttggtctggttgaggaagcggctaagacggctcctggaaagaagaggcctgtagagc<br>agtctcctcaggaaccggactcctccgcgggtattggcaaatcgggtgcacagcccgctaaaaagagactcaatttcggtcagactggcgac<br>acagagtcagtcccagaccctcaaccaatcggagaacctcccgcagccccctcaggtgtgggatctcttacaatggcttcaggtggtggcgc<br>accagtggcagacaataacgaaggtgccgatggagtgggtagttcctcgggaaattggcattgcgattcccaatggctgggggacagagtca<br>tcaccaccagcacccgaacctgggccctgcccacctacaacaatcacctctacaagcaaatctccaacagcacatctggaggatcttcaaat<br>gacaacgcctacttcggctacagcaccccctgggggtattttgacttcaacagattccactgccacttctcaccacgtgactggcagcgact<br>catcaacaacaactggggattccggcctaagcgactcaacttcaagctcttcaacattcaggtcaaagaggttacggacaacaatggagtca<br>agaccatcgccaataaccttaccagcacggtccaggtcttcacggactcagactatcagctcccgtacgtgctcgggtcggctcacgagggc<br>tgcctcccgccgttcccagcggacgttttcatgattcctcagtacgggtatctgacgcttaatgatggaagccaggccgtgggtcgttcgtc |

-continued

| SEQUENCES | |
|---|---|
| SEQ ID NO: | Sequence |
| | cttttactgcctggaatatttcccgtcgcaaatgctaagaacgggtaacaacttccagttcagctacgagtttgagaacgtacctttccata<br>gcagctacgctcacagccaaagcctggaccgactaatgaatccactcatcgaccaatacttgtactatctctcaaagactattaacggttct<br>ggacagaatcaacaaacgctaaaattcagtgtggccggacccagcaacatggctgtccagggaagaaactacatacctggacccagctaccg<br>acaacaacgtgtctcaaccactgtgactcaaaacaacaacagcgaatttgcttggcctggagcttcttcttgggctctcaatggacgtaata<br>gcttgatgaatcctggacctgctatggccagccacaaagaaggagaggaccgtttctttcctttgtctggatctttaattttggcaaacaa<br>ggaactggaagagacaacgtggatgcggacaaagtcatgataaccaacgaagaagaaattaaaactactaacccggtagcaacggagtccta<br>tggacaagtggccacaaaccaccagagtgcccaagcacaggcgcagaccggctgggttcaaaaccaaggaatacttccgggtatggtttggc<br>aggacagagatgtgtacctgcaaggacccatttgggccaaaattcctcacacggacggcaactttcacccttctccgctgatgggagggttt<br>ggaatgaagcacccgcctcctcagatcctcatcaaaaacacacctgtacctgcggatcctccaacggccttcaacaaggacaagctgaactc<br>tttcatcacccagtattctactggccaagtcagcgtggagatcgagtgggagctgcagaaggaaaacagcaagcgctggaacccggagatcc<br>agtacacttccaactattacaagtctaataatgttgaatttgctgttaatactgaaggtgtatatagtgaaccccgccccattggcaccaga<br>tacctgactcgtaatctgtaattgcttgttaatcaataaaccgtttaattcgtttcagttgaactttggtctctgcgtatttctttcttatc<br>tagtttccatgctctaggcggccgcctcgagctgtgccttctagttgccagccatctgttgtttgcccctcccccgtgccttccttgaccct<br>ggaaggtgccactcccactgtcctttcctaataaaatgaggaaattgcatcgcattgtctgagtaggtgtcattctattctggggggggggt<br>ggggcaggacagcaagggggaggattgggaagacaatagcaggcatgctggggagtcgacgcgccggcgtctagaaggaacccctagtgatg<br>gagttggccactccctctctgcgcgctcgctcgctcactgaggccgggcgaccaaaggtcgcccgacgcccgggctttgcccgggcggcctc<br>agtgagcgagcgagcgcgcagagagggagtggccaacagctgcattaatgaatcctgcaggcggccaacgcgcggggagaggcggtttgcgt<br>attgggcgctcttccgcttcctcgctcactgactcgctgcgctcggtcgttcggctgcggcgagcggtatcagctcactcaaaggcggtaat<br>acggttatccacagaatcaggggataacgcaggaaagaacatgtgagcaaaaggccagcaaaaggccaggaaccgtaaaaaggccgcgttgc<br>tggcgtttttccataggctccgcccccctgacgagcatcacaaaaatcgacgctcaagtcagaggtggcgaaacccgacaggactataaaga<br>taccaggcgtttccccctggaagctccctcgtgcgctctcctgttccgaccctgccgcttaccggatacctgtccgcctttctcccttcggg<br>aagcgtggcgctttctcatagctcacgctgtaggtatctcagttcggtgtaggtcgttcgctccaagctgggctgtgtgcacgaaccccccg<br>ttcagcccgaccgctgcgccttatccggtaactatcgtcttgagtccaacccggtaagacacgacttatcgccactggcagcagccactggt<br>aacaggattagcagagcgaggtatgtaggcggtgctacagagttcttgaagtggtggcctaactacggctacactagaagaacagtatttgg<br>tatctgcgctctgctgaagccagttaccttcggaaaaagagttggtagctcttgatccggcaaacaaaccaccgctggtagcggtggttttt<br>ttgtttgcaagcagcagattacgcgcagaaaaaaaggatctcaagaagatcctttgatcttttctacggggtctgacgctcagtggaacgaa<br>aactcacgttaagggattttggtcatgacactacgtgttaccaatgcttaatcagtgaggcacctatctcagcgatctgtctatttcgttca<br>tccatagttgcctgactccccgtcgtgtagataactacgatacgggagggcttaccatctggccccagtgctgcaatgataccgcgagaccc<br>acgctcaccggctccagatttatcagcaataaaccagccagccggaagggccgagcgcagaagtggtcctgcaactttatccgcctccatcc<br>agtctattaattgttgccgggaagctagagtaagtagttcgccagttaatagtttgcgcaacgttgttgccattgctacaggcatcgtggtg<br>tcacgctcgtcgtttggtatggcttcattcagctccggttcccaacgatcaaggcgagttacatgatcccccatgttgtgcaaaaaagcggt<br>tagctccttcggtcctccgatcgttgtcagaagtaagttggccgcagtgttatcactcatggttatggcagcactgcataattctcttactg<br>tcatgccatccgtaagatgcttttctgtgactggtgagtactcaaccaagtcattctgagaatagtgtatgcggcgaccgagttgctcttgc<br>ccggcgtcaatacgggataataccgcgccacatagcagaactttaaaagtgctcatcattggaaaacgttcttcggggcgaaaactctcaag<br>gatcttaccgctgttgagatccagttcgatgtaacccactcgtgcacccaactgatcttcagcatcttttactttcaccagcgtttctgggt<br>gagcaaaaacaggaaggcaaaatgccgcaaaaaagggaataagggcgacacggaaatgttgaatactcatactcttcctttttcaatattat<br>tgaagcatttatcagggttattgtctcatgagcggatacatatttgaatgtatttagaaaaataaacaaataggggttccgcgcactacgt<br>gggatcctcatgagattatcaaaaaggatcttcacctagatccttttcacgtagaaagccagtccgcagaaacggtgctgaccccctgaggc<br>ggaaagaaccagctgtggaatgtgtgtcagttagggtgtggaaagtccccaggctccccagcaggcagaagtatgcaaagcatgcatctcaa<br>ttagtcagcaaccaggtgtggaaagtccccaggctccccagcaggcagaagtatgcaaagcatgcatctcaattagtcagcaaccatagtcc<br>cgcccctaactccgcccatcccgcccctaactccgcccagttccgcccattctccgccccatggctgactaattttttttatttatgcagag<br>gccgaggccgcctcggcctctgagctattccagaagtagtgaggaggcttttttggaggcctaggcttttgcaaaggatgaatgtcagctac<br>tgggctatctggacaagggaaaacgcaagcgcaaagagaaagcaggtagcttgcagtgggcttacatggcgatagctagactgggcggtttt<br>atggacagcaagcgaaccggaattgccagctggggcgccctctggtaaggttgggaagccctgcaaagtaaactggatggctttcttgccgc<br>caaggatctgatggcgcaggggatcaagctctgatcaagagacaggatgaggatcgtttcgcatgattgaacaagatggattgcacgcaggt<br>tctccggccgcttgggtggagaggctattcggctatgactgggcacaacagacaatcggctgctctgatgccgccgtgttccggctgtcagc<br>gcaggggcgcccggttctttttgtcaagaccgacctgtccggtgccctgaatgaactgcaagacgaggcagcgcggctatcgtggctggcca<br>cgacgggcgttccttgcgcagctgtgctcgacgttgtcactgaagcgggaagggactggctgctattgggcgaagtgccggggcaggatctc<br>ctgtcatctcaccttgctcctgccgagaaagtatccatcatggctgatgcaatgcggcggctgcatacgcttgatccggctacctgcccatt<br>cgaccaccaagcgaaacatcgcatcgagcgagcacgtactcggatggaagccggtcttgtcgatcaggatgatctggacgaagagcatcagg<br>ggctcgcgccagccgaactgttcgccaggctcaaggcgagcatgcccgacggcgaggatctcgtcgtgacccatggcgatgcctgcttgccg<br>aatatcatggtggaaaatggccgcttttctggattcatcgactgtggccggctgggtgtggcggaccgctatcaggacatagcgttggctac<br>ccgtgatattgctgaagagcttggcggcgaatgggctgaccgcttcctcgtgctttacggtatcgccgctcccgattcgcagcgcatcgcct<br>tctatcgccttcttgacgagttcttctgaattttcacacaaaaaaccaacacacagatgtaatgaaaataaagatattttattgttaaaatt<br>tttgttaaatcagctcattttttaaccaataggccgaaatcggcaaaatcccttataaatcaaaagaatagaccgagatagggttgagtgtt<br>gttccagtttggaacaagagtccactattaaagaacgtggactccaacgtcaaagggcgaaaaaccgtctatcagggcgatggcccctcgag<br>gaaccatcaccctaatcaagttttttggggtcgaggtgccgtaaagcactaaatcggaaccctaaagggagcccccgatttagagcttgacg<br>gggaaagccggcgaacgtggcgagaaaggaagggaagaaagcgaaaggagcgggcgctagggcgctggcaagtgtagcggtcacgctgcgcg<br>taaccaccacacccgccgcgcttaatgcgccgctacagggcgcgtcgcgtccattcgccattcaggctgcgcaactgttgggaagggctg<br>cag |

LISTING OF EMBODIMENTS

1. A method of inducing immune tolerance to a first recombinant adeno-associated virus (rAAV) in a subject comprising: administering to the subject an effective amount of a second rAAV,
   - wherein the second rAAV is optionally of a different serotype than the serotype of the first rAAV and comprises a nucleic acid sequence encoding at least a portion of a capsid protein that is serotype-matched to the first rAAV, wherein the nucleic acid sequence is operably linked to a promoter; and
   - wherein the second rAAV is capable of infecting a liver cell and expressing the at least a portion of the capsid protein of the first rAAV in the liver thereby inducing immune tolerance to the first rAAV.
2. The method of embodiment 1, wherein the promoter is a constitutive promoter.
3. The method of embodiment 2, wherein the promoter comprises a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, or a j-actin promoter.

4. The method of embodiment 1, wherein the promoter comprises an inducible promoter.

5. The method of embodiment 4, wherein the inducible promoter comprises a cytochrome P450 gene promoter, a heat shock protein gene promoter, a metallothionein gene promoter, a hormone-inducible gene promoter, an estrogen gene promoter, or a tetVP16 promoter that is responsive to tetracycline.

6. The method of embodiment 1 or 2, wherein the promoter comprises a liver-specific promoter or a hepatocyte-specific promoter.

7. The method of embodiment 6, wherein the liver-specific promoter comprises an albumin promoter, an alpha-1-antitrypsin promoter, or a hepatitis B virus core protein promoter.

8. The method of any one of embodiments 1-7, wherein the promoter comprises a synthetic promoter.

9. The method of embodiment 1, wherein the promoter comprises the nucleic acid sequence of SEQ ID NO: 3, or a nucleic acid sequence having at least 90% sequence identity to SEQ ID NO: 3.

10. The method of any one of embodiments 1-9, wherein the at least a portion of the capsid protein of the first rAAV comprises an immunogenic fragment of the capsid protein.

11. The method of embodiment 10, wherein the at least a portion of the capsid protein of the first rAAV comprises at least 10% at least 20%, at least 30%, at least 40%, at least 50%, at least 60%, at least 70%, at least 80%, at least 90%, or 100% of the capsid protein.

12. The method of embodiment 10, wherein the immunogenic fragment of the capsid protein comprises an immunogenic portion of one or more of: a VP1 capsid protein, a VP2 capsid protein, and a VP3 capsid protein.

13. The method of embodiment 12, wherein the immunogenic fragment of the capsid protein comprises an immunogenic portion of the VP3 capsid protein.

14. The method of embodiment 13, wherein the immunogenic fragment of the capsid protein has at least 90% identity to the amino acid sequence of SEQ ID NO: 1.

15. The method of embodiment 14, wherein the immunogenic fragment of the capsid protein is encoded by a nucleic acid sequence having at least 90% identify to SEQ ID NO: 2.

16. The method of any one of embodiments 1-15, wherein the first rAAV is an AAV of serotype 1, serotype 2, serotype 3, serotype 4, serotype 5, serotype 6, serotype 7, serotype 8, serotype 9, serotype 10, serotype 11, rh10, or rh74.

17. The method of any one of embodiments 1-16, wherein the second rAAV is an AAV of serotype 1, serotype 2, serotype 3, serotype 4, serotype 5, serotype 6, serotype 7, serotype 8, serotype 9, serotype 10, serotype 11, rh10 or rh74.

18. The method of any one of embodiments 1-17, wherein the second rAAV is administered systemically.

19. The method of any one of embodiments 1-18, wherein the subject has previously been administered the first rAAV or the subject has not been previously administered the first rAAV.

20. The method of any one of embodiments 1-19, wherein inducing immune tolerance comprises one or more of:

(a) inducing first rAAV-specific regulatory T cells (Tregs), (b) reducing cytotoxic CD8+ T cell response to the first rAAV, (c) reducing the level of pre-existing antibodies to the first rAAV, and (d) reduce production of antibodies against the first rAAV.

21. The method of anyone of Embodiments 1-20, wherein the first and the second rAAV are the same serotype.

22. A method for inducing an immune response to an antigen in a subject comprising (a) administering to the subject an effective amount of a first recombinant adeno-associated virus (rAAV) comprising a first nucleotide sequence encoding the antigen, wherein the first nucleotide sequence is operably linked to a first promoter; and (b) administering to the subject an effective amount of a second rAAV, wherein the second rAAV is of a different serotype than the first rAAV and comprises a second nucleic acid sequence encoding at least a portion of a capsid protein of the first rAAV, wherein the second nucleic acid sequence is operably linked to a second promoter; and wherein the second rAAV is capable of infecting a liver cell and expressing the at least a portion of the capsid protein of the first rAAV in the liver thereby inducing immune tolerance to the first rAAV.

23. The method of embodiment 22, wherein the first promoter and/or the second promoter are constitutive promoters.

24. The method of embodiment 23, wherein the first promoter and/or the second promoter independently comprise a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, or a j-actin promoter.

25. The method of embodiment 22, wherein the first promoter and/or the second promoter comprise an inducible promoter.

26. The method of embodiment 25, wherein the inducible promoter comprises a cytochrome P450 gene promoter, a heat shock protein gene promoter, a metallothionein gene promoter, a hormone-inducible gene promoter, an estrogen gene promoter, or a tetVP16 promoter that is responsive to tetracycline.

27. The method of embodiment 22, wherein the first promoter and/or the second promoter comprise tissue-specific promoters.

28. The method of embodiment 27, wherein the promoter comprises a neuronal- or muscle-specific promoter.

29. The method of embodiment 28, wherein the first promoter comprises a muscle-specific promoter selected from the group consisting of: a desmin promoter, a creatine kinase promoter, a myogenin promoter, an alpha myosin heavy chain promoter and a natriuretic peptide promoter.

30. The method of embodiment 27, wherein the second promoter comprises a liver-specific promoter or a hepatocyte-specific promoter.

31. The method of embodiment 30, wherein the liver-specific promoter comprises an albumin promoter, an alpha-1-antitrypsin promoter, or a hepatitis B virus core protein promoter.

32. The method of any one of embodiments 23-31, wherein the first promoter and/or the second promoter comprise synthetic promoters.

33. The method of embodiment 32, wherein the second promoter comprises the nucleic acid sequence pf SEQ ID NO: 3, or a nucleic acid sequence having at least 90% sequence identity to SEQ ID NO: 3.

34. The method of any one of embodiments 22-33, wherein the at least a portion of the capsid protein of the first rAAV comprises an immunogenic fragment of the capsid protein.

35. The method of embodiment 34, wherein the at least a portion of the capsid protein of the first rAAV comprises at least 10% at least 20%, at least 30%, at least 40%, at least 50%, at least 60%, at least 70%, at least 80%, at least 90%, or 100% of the capsid protein.

36. The method of embodiment 34, wherein the immunogenic fragment of the capsid protein comprises an immunogenic portion of one or more of: a VP1 capsid protein, a VP2 capsid protein, and a VP3 capsid protein.

37. The method of embodiment 36, wherein the immunogenic fragment of the capsid protein comprises an immunogenic portion of the VP3 capsid protein.

38. The method of embodiment 37, wherein the immunogenic fragment of the capsid protein has at least 90% identity to the amino acid sequence of SEQ ID NO: 1.

39. The method of embodiment 38, wherein the immunogenic fragment of the capsid protein is encoded by a nucleic acid sequence having at least 90% identify to SEQ ID NO: 2.

40. The method of any one of embodiments 3-33, wherein the first rAAV is an AAV serotype selected from the group consisting of: serotype 1, serotype 2, serotype 3, serotype 4, serotype 5, serotype 6, serotype 7, serotype 8, serotype 9, serotype 10, serotype 11, rh10 and rh74.

41. The method of any one of embodiments 22-34, wherein the second rAAV is an AAV serotype selected from the group consisting of: serotype 1, serotype 2, serotype 3, serotype 4, serotype 5, serotype 6, serotype 7, serotype 8, serotype 9, serotype 10, serotype 11, rh10 and rh74.

42. The method of any one of embodiments 22-33, wherein the first rAAV is serotype 1 or 2 and the second rAAV is serotype 9 or rh74.

43. The method of any one of embodiments 22-42, wherein (a) the first rAAV and the second rAAV are co-administered;

(b) the first rAAV is administered before the second rAAV; or (c) the first rAAV is administered after the second rAAV.

44. The method of any one of embodiments 22-43, wherein the second rAAV is administered by intravenous injection.

45. The method of any one of embodiments 22-44, wherein the antigen comprises a viral antigen, a bacterial antigen, a parasite antigen, a fungal antigen, or a tumor antigen.

46. The method according to any one of embodiments 22-45, wherein (a) the first rAAV contains a nucleic acid sequence sharing at least 85% sequence identity to SEQ ID NO: 6 and/or SEQ ID NO: 8; (b) the first rAAV contains a nucleic acid sequence sharing at least 95% sequence identity to SEQ ID NO: 6 and/or SEQ ID NO: 8; or (c) the first rAAV contains a nucleic acid sequence comprising SEQ ID NO: 6 and/or SEQ ID NO: 8.

47. The method of embodiment 46, wherein antigen comprises at least a portion of a SARS-CoV-2 polypeptide.

48. The method of embodiment 47, wherein the SARS-CoV-2 polypeptide comprises an S1 subunit of the SARS-CoV-2 spike glycoprotein.

50. The method of embodiment 47, wherein the SARS-Cov-2 polypeptide comprises an N-terminal or C-terminal domain of an S1 subunit of the SARS-Cov-2 spike glycoprotein.

51. The method of any one of embodiments 22-49, further comprising administering to the subject a second effective amount of the first rAAV, wherein the second effective dose is administered after the first effective dose.

52. The method of any one of embodiment 22-50, wherein inducing an immune response comprises one or more of:

(a) eliciting a cellular immune response to the antigen;

(b) elicit a humoral immune response to the antigen;

(c) enhancing proliferation of antigen-specific cytotoxic T lymphocytes;

(d) eliciting generation of anti-antigen antibodies;

(e) reduce the likelihood of infection by pathogen containing the antigen;

(f) vaccinating the subject against the pathogen containing the antigen; and (g) treating cancer.

53. A method for providing a therapeutic nucleic acid to a subject comprising:

administering to the subject an effective amount of a first recombinant adeno-associated virus (rAAV) having a first serotype, wherein the first rAAV comprises the therapeutic nucleic acid; and administering to the subject a second rAAV having a second serotype that is optionally different from the first serotype, wherein the second rAAV comprises a second nucleic acid sequence encoding at least a portion of a capsid protein that is serotype-matched to the first rAAV, wherein the second nucleic acid sequence is operably linked to a second promoter; and wherein the second rAAV is capable of infecting a liver cell and expressing the at least a portion of the capsid protein of the first rAAV in the liver thereby inducing immune tolerance to the first rAAV.

54. The method of embodiment 52, wherein the therapeutic nucleic acid comprises a coding sequence operably linked to a first promoter.

55. The method of embodiment 53, wherein the first promoter and/or the second promoter are constitutive promoters.

56. The method of embodiment 53, wherein the first promoter and/or the second promoter independently comprise a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, or a j-actin promoter.

57. The method of embodiment 53, wherein the first promoter and/or the second promoter comprise an inducible promoter.

58. The method of embodiment 56, wherein the inducible promoter comprises a cytochrome P450 gene promoter, a heat shock protein gene promoter, a metallothionein gene promoter, a hormone-inducible gene promoter, an estrogen gene promoter, or a tetVP16 promoter that is responsive to tetracycline.

59. The method of embodiment 53, wherein the first promoter and/or the second promoter comprise tissue-specific promoters.

60. The method of embodiment 58, wherein the promoter comprises a neuronal- or muscle-specific promoter.

61. The method of embodiment 59, wherein the first promoter comprises a muscle-specific promoter selected from the group consisting of: a desmin promoter, a creatine kinase promoter, a myogenin promoter, an alpha myosin heavy chain promoter and a natriuretic peptide promoter.

62. The method of embodiment 59 or 60, wherein the second promoter comprises a liver-specific promoter or a hepatocyte-specific promoter.

63. The method of embodiment 61, wherein the liver-specific promoter comprises an albumin promoter, an alpha-1-antitrypsin promoter, or a hepatitis B virus core protein promoter.

64. The method of any one of embodiments 53-62, wherein the first promoter and/or the second promoter comprise synthetic promoters.

65. The method of embodiment 61, wherein the second promoter comprises the nucleic acid sequence pf SEQ ID NO: 3, or a nucleic acid sequence having at least 90% sequence identity to SEQ ID NO: 3.

66. The method of any one of embodiments 52-64, wherein the at least a portion of the capsid protein of the first rAAV comprises an immunogenic fragment of the capsid protein.

67. The method of embodiment 65, wherein the at least a portion of the capsid protein of the first rAAV comprises at least 10% at least 20%, at least 30%, at least 40%, at least 50%, at least 60%, at least 70%, at least 80%, at least 90%, or 100% of the capsid protein.

68. The method of embodiment 65, wherein the immunogenic fragment of the capsid protein comprises an immunogenic portion of one or more of: a VP1 capsid protein, a VP2 capsid protein, and a VP3 capsid protein.

69. The method of embodiment 67, wherein the immunogenic fragment of the capsid protein comprises an immunogenic portion of the VP3 capsid protein.

70. The method of embodiment 68, wherein the immunogenic fragment of the capsid protein has at least 90% identity to the amino acid sequence of SEQ ID NO: 1.

71. The method of embodiment 68, wherein the immunogenic fragment of the capsid protein is encoded by a nucleic acid sequence having at least 90% identify to SEQ ID NO: 2.

72. The method of any one of embodiments 52-70, wherein the first rAAV is an AAV serotype selected from the group consisting of: serotype 1, serotype 2, serotype 3, serotype 4, serotype 5, serotype 6, serotype 7, serotype 8, serotype 9, serotype 10, serotype 11, rh10 and rh74.

73. The method of any one of embodiments 52-71, wherein the second rAAV is an AAV serotype selected from the group consisting of: serotype 1, serotype 2, serotype 3, serotype 4, serotype 5, serotype 6, serotype 7, serotype 8, serotype 9, serotype 10, serotype 11, rh10 and rh74.

74. The method of any one of embodiments 52-70, wherein the first rAAV is serotype 1 or 2 and the second rAAV is serotype 9 or rh74.

The method of any one of embodiments 52-73, wherein (a) the first rAAV and the second rAAV are co-administered;

(b) the first rAAV is administered before the second rAAV; or (c) the first rAAV is administered after the second rAAV.

75. The method of any one of embodiments 52-74, wherein the second rAAV is administered by intravenous injection.

76. The method of any one of embodiments 52-75, further comprising administering to the subject a second effective amount of the first rAAV, wherein the second effective dose is administered after the first effective dose.

77. The method of any one of embodiment 52-76, wherein inducing immune tolerance comprises:

(a) inducing first rAAV-specific regulatory T cells (Tregs), (b) reducing cytotoxic CD8+ T cell response to the first rAAV, (c) reducing the level of pre-existing antibodies to the first rAAV, and (d) reduce production of antibodies against the first rAAV.

78. The method according to any one of embodiments 52-77, wherein the therapeutic nucleic acid coding sequence encodes a therapeutic RNA, mRNA, an aptamer, a microRNA, an siRNA, an RNA interference polynucleotide, an antisense RNA, a ribozyme, a Cas endonuclease RNA, or a therapeutic polypeptide.

79. The method of embodiment 78, wherein the therapeutic protein is selected from the group consisting of: human frataxin, myotubularin, a muscle protein, a neuronal protein, acid alfa glucosidase (GAA), and aspartoacylase.

80. An rAAV comprising a nucleic acid sequence encoding an immunogenic portion of a capsid protein of a second rAAV having a serotype that is optionally different from the rAAV; wherein the nucleic acid sequence is operably linked to a promoter, and wherein the rAAV is capable of infecting a liver cell and expressing the immunogenic portion of the capsid protein in the liver thereby inducing immune tolerance to the second rAAV.

81. The rAAV of embodiment 80, wherein the promoter is a constitutive promoter.

82. The rAAV of embodiment 81, wherein the promoter comprises a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, or a 3-actin promoter.

83. The rAAV of embodiment 80, wherein the promoter comprises an inducible promoter.

84. The rAAV of embodiment 83, wherein the inducible promoter comprises a cytochrome P450 gene promoter, a heat shock protein gene promoter, a metallothionein gene promoter, a hormone-inducible gene promoter, an estrogen gene promoter, or a tetVP16 promoter that is responsive to tetracycline.

85. The rAAV of embodiment 80 or 81, wherein the promoter comprises a liver-specific promoter or a hepatocyte-specific promoter.

86. The rAAV of embodiment 85, wherein the liver-specific promoter comprises an albumin promoter, an alpha-1-antitrypsin promoter, or a hepatitis B virus core protein promoter.

87. The rAAV of any one of embodiments 80-86, wherein the promoter comprises a synthetic promoter.

88. The rAAV of embodiment 80, wherein the promoter comprises the nucleic acid sequence of SEQ ID NO: 3, or a nucleic acid sequence having at least 90% sequence identity to SEQ ID NO: 3.

89. The rAAV of any one of embodiments 80-88, wherein the immunogenic portion of a capsid protein of a second rAAV comprises the capsid protein.

90. The rAAV of any one of embodiments 80-88, wherein the immunogenic portion of the capsid protein of the second rAAV comprises at least 10% at least 20%, at least 30%, at least 40%, at least 50%, at least 60%, at least 70%, at least 80%, at least 90% of the capsid protein.

91. The rAAV of embodiment 90, wherein the immunogenic portion of the capsid protein comprises an immunogenic portion of one or more of: a VP1 capsid protein, a VP2 capsid protein, and a VP3 capsid protein.

92. The rAAV of embodiment 91, wherein the immunogenic portion of the capsid protein comprises an immunogenic portion of the VP3 capsid protein.

93. The rAAV of embodiment 92, wherein the immunogenic portion of the capsid protein has at least 90% identity to the amino acid sequence of SEQ ID NO: 1.

94. The rAAV of embodiment 92, wherein the immunogenic portion of the capsid protein is encoded by a nucleic acid sequence having at least 90% identify to SEQ ID NO: 2.

95. The rAAV of any one of embodiments 80-94, wherein the rAAV has an AAV serotype selected from the group consisting of: serotype 1, serotype 2, serotype 3, serotype 4, serotype 5, serotype 6, serotype 7, serotype 8, serotype 9, serotype 10, and serotype 11.

96. A composition comprising the rAAV of any one of embodiments 80-95.

97. The composition of embodiment 96, further comprising the second AAV having a serotype optionally different from the serotype of the rAAV, wherein the second rAAV comprises a therapeutic nucleic acid sequence.

98. The composition of embodiment 97, wherein the therapeutic nucleic acid sequence is operably linked to a second promoter and encodes a therapeutic RNA, mRNA, an aptamer, a microRNA, an siRNA, an RNA interference polynucleotide, an antisense RNA, a ribozyme, a CRISPR RNA, a therapeutic polypeptide, or an antigenic polypeptide.

99. The composition of embodiment 98, wherein the second promoter is a constitutive promoter, an inducible promoter, or a tissue-specific promoter, or a synthetic promoter.

100. The composition of embodiment 99, wherein the second promoter comprises: a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, a 3-actin promoter, a cytochrome P450 gene promoter, a heat shock protein gene promoter, a metallothionein gene promoter, a hormone-inducible gene promoter, an estrogen gene promoter, a tetVP16 promoter that is responsive to tetracycline, a neuronal-specific promoter, a muscle-specific promoter, a desmin promoter, a creatine kinase promoter, a myogenin promoter, an alpha myosin heavy chain promoter, or a natriuretic peptide promoter.

101. The composition of embodiment 100, wherein (a) the second rAAV contains a nucleic acid sequence sharing at least 85% sequence identity to SEQ ID NO: 6 and/or SEQ ID NO: 8; (b) the second rAAV contains a nucleic acid sequence sharing at least 95% sequence identity to SEQ ID NO: 6 and/or SEQ ID NO: 8; or (c) the second rAAV contains a nucleic acid sequence comprising SEQ ID NO: 6 and/or SEQ ID NO: 8.

102. The composition of embodiment 98, wherein antigenic polypeptide comprises at least a portion of a SARS-CoV-2 polypeptide.

103. The composition of embodiment 102, wherein the SARS-CoV-2 polypeptide comprises an S1 subunit of the SARS-CoV-2 spike glycoprotein.

104. The composition of embodiment 102, wherein the SARS-Cov-2 polypeptide comprises an N-terminal or C-terminal domain of an S1 subunit of the SARS-Cov-2 spike glycoprotein.

105. The composition of any one of embodiments 97-104, wherein the second rAAV is an AAV serotype selected from the group consisting of: serotype 1, serotype 2, serotype 3, serotype 4, serotype 5, serotype 6, serotype 7, serotype 8, serotype 9, serotype 10, and serotype 11.

106. The composition embodiment 105, wherein the rAAV is serotype 2 or serotype 9 and the second rAAV is serotype 1.

107. A nucleic acid encoding the rAAV of any one of embodiments 80-95.

108. A host cell comprising the rAAV of any one of embodiments 80-95 or the nucleic acid or embodiment 107.

109. A kit comprising the composition of any one of embodiments 96-105.

EXAMPLES

Example 1. Assessment of Safety of Vaccination of an Individual with a rAAV2-LSP(GAA)-AAV1-VP3 vector in order to induce immune tolerance to subsequent intramuscular administration of a recombinant adeno-associated virus vector, rAAV1-CMV-SARS-COV-2, in healthy adult volunteers.

Two dose levels ($1.0\times10^{13}$ and $5.0\times10^{12}$ VG) will be studied. One goal is to determine the degree of immune tolerance induced to rAAV1 vectors, through the liver-specific expression of an immunogenic portion of AAV1 VP3 capsid protein.

The study population will be made up of 6 subjects, male or female, 18-75 years of age, three with an anti-AAV1 titer of <100 U/ml and three with an anti-AAV1 titer of 100-500 U/ml. All subjects will be healthy volunteers who test negative for SARS-CoV-2 at screening. An intravenous injection of the requisite dose will be administered to three subjects at each dose level. One week later, each subject will be administered a corresponding dose (low to low and high to high) rAAV1-CMV-SARS-COV-2 vector delivered intramuscularly (either $1.0\times10^{13}$ and $5.0\times10^{12}$ VG). One goal is to determine the safety of in healthy adults as well as to determine the efficacy of rAAV1-CMV-SARS-COV-2 vector in producing the anti-SARS-COV-2 antibody.

Following screening visit and vaccine administration at day 0, subjects will be evaluated at a clinical site on days 3, 7, 14, 28 and 90, of the trial. Following day 90, subjects will be evaluated by the study nurse by telephone, or video conference when available. Subjects may be provided with a sample collection kit if they are experiencing any long-term side-effects. Blood samples will be collected at an outpatient facility and shipped to the clinical site for analysis. At each visit to the clinical site, subjects will have a physical examination and laboratory evaluation of chemistry and hematology.

In addition, at days 3, 7, 14, 28 and 90 the presence of vector in peripheral blood will be evaluated. Testing for the presence of anti-AAV1 and anti-SARS-CoV-2 antibodies will occur at screening, day 0 (pre-injection), and days 3, 7, 14, 28 and 90.

Safety will be assessed by measurement of changes in serum chemistries, coagulation and hematology, urinalysis, and immunologic response to SARS-CoV-2 and AAV1 as well as reported subject history of any symptoms.

Impact of the vaccine in promoting the production of anti-SARS-CoV-2 antibodies will be assessed by measurement of IgG and IgM for SARS-COV-2 in the blood. Testing will be done at screening, baseline and 3, 7, 14, 28, and 90 days following vaccine administration.

Example 2. A clinical study will be performed to verify the safety and efficacy of certain embodiments disclosed herein. The study will be conducted in healthy control adult subjects at two dosing levels, $5\times10^{12}$ VG and $1\times10^{13}$ VG delivered intramuscularly in the quadriceps muscle. This study will test several important concepts leading to immediate immunization of susceptible individuals. The critical advantage of an AAV-based vaccine is that single administration in a 1.0 ml IM injection will lead to ongoing expression of the modified soluble coronavirus spike protein (or other viral protein) and elicit a potent anti-spike polyclonal response. Based on non-clinical studies, the level of antibody should exceed the threshold for effective neutralization of SARS-CoV-2.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. In addition, where features or aspects of the disclosure are described in terms of Markush groups, those skilled in the art will recognize that the disclosure is also thereby described in terms of any individual member or subgroup of members of the Markush group.

Sequences

In some embodiments, there are provided amino acid sequences that correspond to any of the nucleic acids disclosed herein (and/or included in the accompanying sequence listing), while accounting for degeneracy of the nucleic acid code. Furthermore, those sequences (whether nucleic acid or amino acid) that vary from those expressly disclosed herein (and/or included in the accompanying sequence listing), but have functional similarity or equivalency are also contemplated within the scope of the present disclosure. The foregoing includes mutants, truncations, substitutions, or other types of modifications.

In accordance with some embodiments described herein, any of the sequences may be used, or a truncated or mutated form of any of the sequences disclosed herein (and/or included in the accompanying sequence listing) may be used and in any combination.

Any titles or subheadings used herein are for organization purposes and should not be used to limit the scope of embodiments disclosed herein.

What is claimed is:

1. A method of inducing immune tolerance to a first recombinant adeno-associated virus (rAAV) in a subject comprising: administering to the subject an effective amount of a second rAAV, wherein the second rAAV is optionally of a different serotype than the serotype of the first rAAV and comprises a nucleic acid sequence encoding at least a portion of a capsid protein that is serotype-matched to the first rAAV, wherein the nucleic acid sequence is operably linked to a promoter; and wherein the second rAAV is capable of infecting a liver cell and expressing the at least a portion of the capsid protein of the first rAAV in the liver thereby inducing immune tolerance to the first rAAV.

2. The method of claim 1, wherein the promoter is a constitutive promoter, an inducible promoter, a liver-specific or hepatocyte-specific promoter, or a synthetic promoter.

3. The method of claim 2, wherein the promoter is (a) a constitutive promoter selected from the group consisting of: a Herpes Simplex virus (HSV) promoter, a thymidine kinase (TK) promoter, a Rous Sarcoma Virus (RSV) promoter, a Simian Virus 40 (SV40) promoter, a Mouse Mammary Tumor Virus (MMTV) promoter, an Adenovirus E1A promoter, a cytomegalovirus (CMV) promoter, a mammalian housekeeping gene promoter, or a β-actin promote;

(b) an inducible promoter selected from the group consisting of: a cytochrome P450 gene promoter, a heat shock protein gene promoter, a metallothionein gene promoter, a hormone-inducible gene promoter, an estrogen gene promoter, or a tetVP16 promoter that is responsive to tetracycline;

(c) a liver-specific or hepatocyte-specific promoter selected from the group consisting of: an albumin promoter, an alpha-1-antitrypsin promoter, or a hepatitis B virus core protein promoter; or (d) a synthetic promoter comprising the nucleic acid sequence of SEQ ID NO: 3, or a nucleic acid sequence having at least 90% sequence identity to SEQ ID NO: 3.

4. The method of claim 1, wherein at least a portion of a capsid protein comprises an immunogenic portion of one or more of: a VP1 capsid protein, a VP2 capsid protein, and a VP3 capsid protein.

5. The method of claim 4, wherein the immunogenic fragment of the capsid protein has at least 90% identity to the amino acid sequence of SEQ ID NO: 1 or is encoded by a nucleic acid sequence having at least 90% identify to SEQ ID NO: 2.

6. The method of claim 1, wherein (a) the first rAAV is an AAV of serotype 1, serotype 2, serotype 3, serotype 4, serotype 5, serotype 6, serotype 7, serotype 8, serotype 9, serotype 10, serotype 11, rh10, or rh74; and (b) the second rAAV is an AAV of serotype 1, serotype 2, serotype 3, serotype 4, serotype 5, serotype 6, serotype 7, serotype 8, serotype 9, serotype 10, serotype 11, rh10 or rh74.

7. The method of claim 1, wherein inducing immune tolerance comprises one or more of:

(a) inducing first rAAV-specific regulatory T cells (Tregs), (b) reducing cytotoxic CD8+ T cell response to the first rAAV, (c) reducing the level of pre-existing antibodies to the first rAAV, and (d) reducing production of antibodies against the first rAAV.

8. A method for providing a therapeutic nucleic acid to a subject comprising:

(a) administering to the subject an effective amount of a first recombinant adeno-associated virus (rAAV) having a first serotype, wherein the first rAAV comprises the therapeutic nucleic acid; and (b) administering to the subject a second rAAV having a second serotype that is optionally different from the first serotype, wherein the second rAAV comprises a second nucleic acid sequence encoding at least a portion of a capsid protein that is serotype-matched to the first rAAV, wherein the second nucleic acid sequence is operably linked to a second promoter; and wherein the second rAAV is capable of infecting a liver cell and expressing the at least a portion of the capsid protein of the first rAAV in the liver thereby inducing immune tolerance to the first rAAV.

9. The method of claim 8, wherein the therapeutic nucleic acid comprises a coding sequence operably linked to a first promoter, wherein the promoter is a constitutive promoter, an inducible promoter, s tissue-specific promoter; and wherein the second promoter comprises a liver-specific promoter or a synthetic promoter comprising the nucleic acid sequence pf SEQ ID NO: 3 or a nucleic acid sequence having at least 90% sequence identity to SEQ ID NO: 3.

10. The method of claim 8, wherein the first rAAV is serotype 1 or 2 and the second rAAV is serotype 9 or rh74.

11. The method of claim 8, wherein the method further comprises administering to the subject a second effective amount of the first rAAV, wherein the second effective dose is administered after the first effective dose.

12. The method of claim 9, wherein the therapeutic nucleic acid encodes a therapeutic protein.

13. The method of claim 12, wherein the therapeutic protein is selected from the group consisting of: human frataxin, myotubularin, a muscle protein, a neuronal protein, acid alpha glucosidase (GAA), and aspartoacylase.

14. The method of claim 9, wherein the therapeutic nucleic acid encodes an antigen.

15. The method of claim 14, wherein the first promoter comprises a neuronal- or muscle-specific promoter and the second promoter comprises a liver-specific promoter or a synthetic promoter comprising the nucleic acid sequence pf SEQ ID NO: 3 or a nucleic acid sequence having at least 90% sequence identity to SEQ ID NO: 3.

16. The method of claim 15, wherein the antigen comprises a viral antigen, a SARS-CoV-2 polypeptide, a bacterial antigen, a parasite antigen, a fungal antigen, or a tumor antigen.

17. The method of claim 16, wherein providing the therapeutic nucleic acid to a subject results in one or more of:

(a) eliciting a cellular immune response to the antigen;

(b) eliciting a humoral immune response to the antigen;

(c) enhancing proliferation of antigen-specific cytotoxic T lymphocytes;

(d) eliciting generation of anti-antigen antibodies;

(e) reducing the likelihood of infection by pathogen containing the antigen;

(f) vaccinating the subject against the pathogen containing the antigen; and (g) treating cancer.

18. An rAAV comprising a nucleic acid sequence encoding an immunogenic portion of a capsid protein of a second rAAV having a serotype that is different from the rAAV; wherein the nucleic acid sequence is operably linked to a promoter, and wherein the rAAV is capable of infecting a liver cell and expressing the immunogenic portion of the capsid protein in the liver thereby inducing immune tolerance to the second rAAV.

19. The rAAV of claim 18, wherein the promoter is a constitutive promoter, an inducible promoter, a liver-specific promoter, a hepatocyte-specific promoter, a synthetic promoter comprising a nucleic acid sequence of SEQ ID NO: 3, or a nucleic acid sequence having at least 90% sequence identity to SEQ ID NO: 3.

20. A nucleic acid encoding the rAAV of claim 19.

* * * * *